(12) United States Patent
Gonzalez Blohm et al.

(10) Patent No.: US 12,178,486 B2
(45) Date of Patent: Dec. 31, 2024

(54) TRANSDISCAL SCREW

(71) Applicant: H. LEE MOFFITT CANCER CENTER AND RESEARCH INSTITUTE, INC., Tampa, FL (US)

(72) Inventors: Sabrina A. Gonzalez Blohm, Tampa, FL (US); James J. Doulgeris, Oldsmar, FL (US); Kamran Aghayev, Tampa, FL (US); Frank D. Vrionis, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 141 days.

(21) Appl. No.: 17/712,781

(22) Filed: Apr. 4, 2022

(65) Prior Publication Data

US 2022/0370109 A1 Nov. 24, 2022

Related U.S. Application Data

(63) Continuation of application No. 16/435,886, filed on Jun. 10, 2019, now Pat. No. 11,291,489, which is a continuation of application No. 15/105,210, filed as application No. PCT/US2014/070899 on Dec. 17, 2014, now Pat. No. 10,314,631.

(60) Provisional application No. 61/917,183, filed on Dec. 17, 2013.

(51) Int. Cl.
*A61B 17/86* (2006.01)
*A61B 17/70* (2006.01)

(52) U.S. Cl.
CPC .......... *A61B 17/8685* (2013.01); *A61B 17/70* (2013.01); *A61B 17/864* (2013.01); *A61B 17/7037* (2013.01)

(58) Field of Classification Search
CPC ................. A61B 17/7037; A61B 17/8685
See application file for complete search history.

(56) References Cited

U.S. PATENT DOCUMENTS

| | | | |
|---|---|---|---|
| 6,517,543 B1 | 2/2003 | Berrevoets et al. | |
| 6,921,403 B2 | 7/2005 | Cragg | |
| 7,799,057 B2 | 9/2010 | Hudgins et al. | |
| 8,043,334 B2 | 10/2011 | Fisher et al. | |
| 9,445,848 B2 | 9/2016 | Anderson | |

(Continued)

FOREIGN PATENT DOCUMENTS

WO 2013/052807 4/2013

OTHER PUBLICATIONS

International Preliminary Report on Patentability and Written Opinion, dated Jun. 21, 2016, received in connection with International Patent Application No. PCT/US2014/070899.

(Continued)

*Primary Examiner* — Olivia C Chang
(74) *Attorney, Agent, or Firm* — Meunier Carlin & Curfman LLC

(57) ABSTRACT

This invention relates to a transdiscal screw capable of following a non-linear trajectory. The screw assembly includes a first screw and second screw coupled at a poly-axial joint. The first screw and the second screw capable of rotating independently of each other. The screw can also include a third screw coupled to the second screw at a poly-axial joint such that the first screw, second screw and third screw can rotate independently of each other.

18 Claims, 61 Drawing Sheets

(56) References Cited

U.S. PATENT DOCUMENTS

| | | | |
|---|---|---|---|
| 9,482,260 | B1 | 11/2016 | Krause |
| 10,322,009 | B2 | 6/2019 | Aghayev et al. |
| 10,687,876 | B2 | 6/2020 | Vrionis et al. |
| 10,792,083 | B2 | 10/2020 | Vrionis et al. |
| 10,799,367 | B2 | 10/2020 | Vrionis et al. |
| 11,134,997 | B2 | 10/2021 | Vrionis et al. |
| 2002/0195827 | A1 | 12/2002 | Jackson et al. |
| 2004/0122431 | A1 | 6/2004 | Biedermann et al. |
| 2004/0210227 | A1 | 10/2004 | Trail et al. |
| 2005/0143735 | A1 | 6/2005 | Kyle |
| 2005/0197660 | A1 | 9/2005 | Haid et al. |
| 2005/0261695 | A1 | 11/2005 | Cragg et al. |
| 2005/0277923 | A1 | 12/2005 | Sweeney |
| 2006/0036322 | A1 | 2/2006 | Reiley |
| 2006/0155297 | A1 | 7/2006 | Ainsworth |
| 2007/0167951 | A1 | 7/2007 | Ainsworth et al. |
| 2007/0270855 | A1 | 11/2007 | Partin |
| 2009/0076607 | A1 | 3/2009 | Aalsma et al. |
| 2009/0118771 | A1 | 5/2009 | Gonzalez-Hernandez |
| 2009/0254129 | A1 | 10/2009 | Tipirneni et al. |
| 2009/0281628 | A1 | 11/2009 | Oglaza et al. |
| 2010/0003638 | A1 | 1/2010 | Collins et al. |
| 2010/0049244 | A1 | 2/2010 | Cohen et al. |
| 2010/0082109 | A1 | 4/2010 | Greenhalgh |
| 2010/0292695 | A1 | 11/2010 | May et al. |
| 2011/0040329 | A1 | 2/2011 | Ainsworth et al. |
| 2011/0054545 | A1* | 3/2011 | Champagne ....... A61B 17/7225 606/301 |
| 2011/0087294 | A1 | 4/2011 | Reiley |
| 2011/0106172 | A1 | 5/2011 | Wallenstein |
| 2011/0144703 | A1 | 6/2011 | Krause et al. |
| 2011/0224738 | A1 | 9/2011 | Sucec et al. |
| 2011/0282378 | A1 | 11/2011 | Murphy |
| 2011/0319946 | A1 | 12/2011 | Levy et al. |
| 2013/0006361 | A1 | 1/2013 | Glerum |
| 2013/0053902 | A1 | 2/2013 | Trudeau |
| 2013/0211526 | A1 | 8/2013 | Alheidt et al. |
| 2013/0231747 | A1 | 9/2013 | Olmos et al. |
| 2013/0325075 | A1 | 12/2013 | Jackson |
| 2014/0114312 | A1 | 4/2014 | Krause |
| 2014/0142639 | A1 | 5/2014 | Vennard |
| 2014/0172027 | A1 | 6/2014 | Bidermann |
| 2014/0188180 | A1 | 7/2014 | Bidermann |
| 2014/0277139 | A1 | 9/2014 | Vrionis et al. |
| 2015/0012048 | A1 | 1/2015 | Huebner et al. |
| 2018/0092677 | A1 | 4/2018 | Peterson et al. |
| 2018/0206897 | A1 | 7/2018 | Palmer |

OTHER PUBLICATIONS

International Search Report and Written Opinion, dated May 14, 2015, received in connection with International Patent Application No. PCT/US2014/070899.

International Preliminary Report on Patentability and Written Opinion, dated Apr. 8, 2014, received in connection with International Patent Application No. PCT/US2012/058968.

International Search Report and Written Opinion, dated Mar. 28, 2013, received in connection with International Patent Application No. PCT/US2012/058968.

International Search Report and Written Opinion, dated Nov. 2, 2015, received in connection with International Patent Application No. PCT/US2015/043109.

International Preliminary Report on Patentability and Written Opinion, dated Feb. 16, 2017, received in connection with International Patent Application No. PCT/US2015/043109.

* cited by examiner

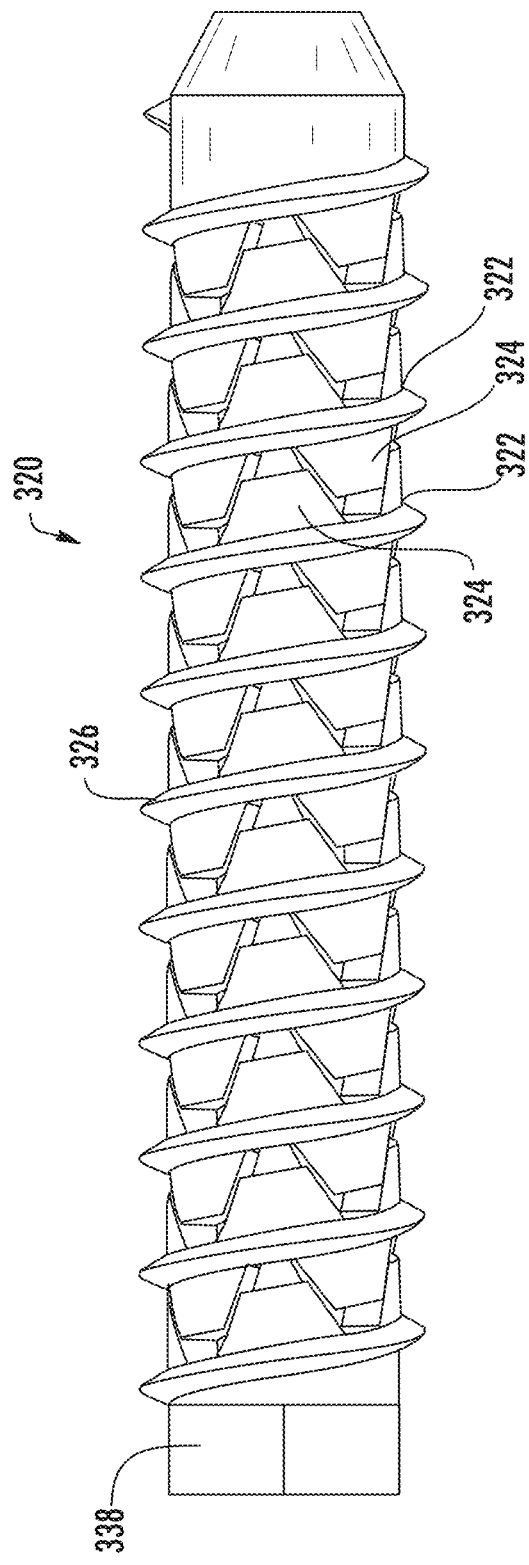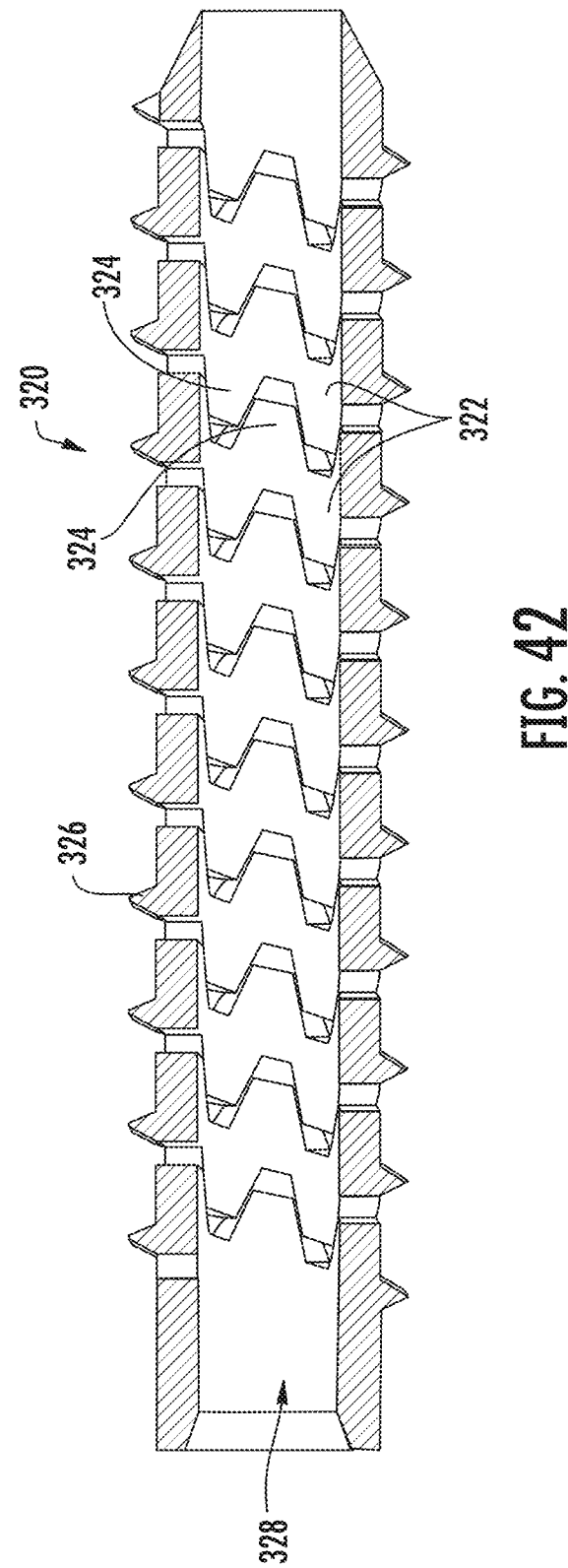

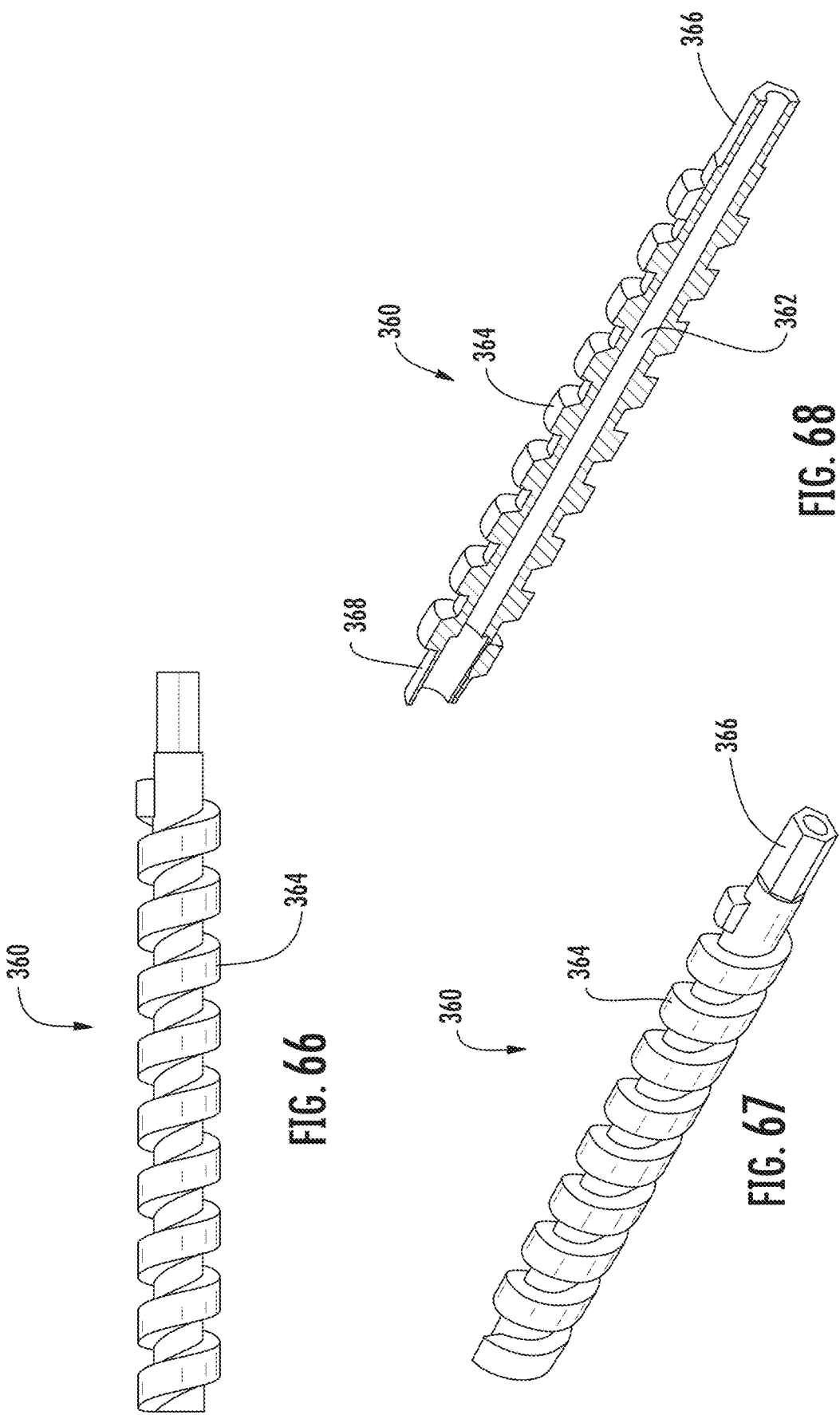

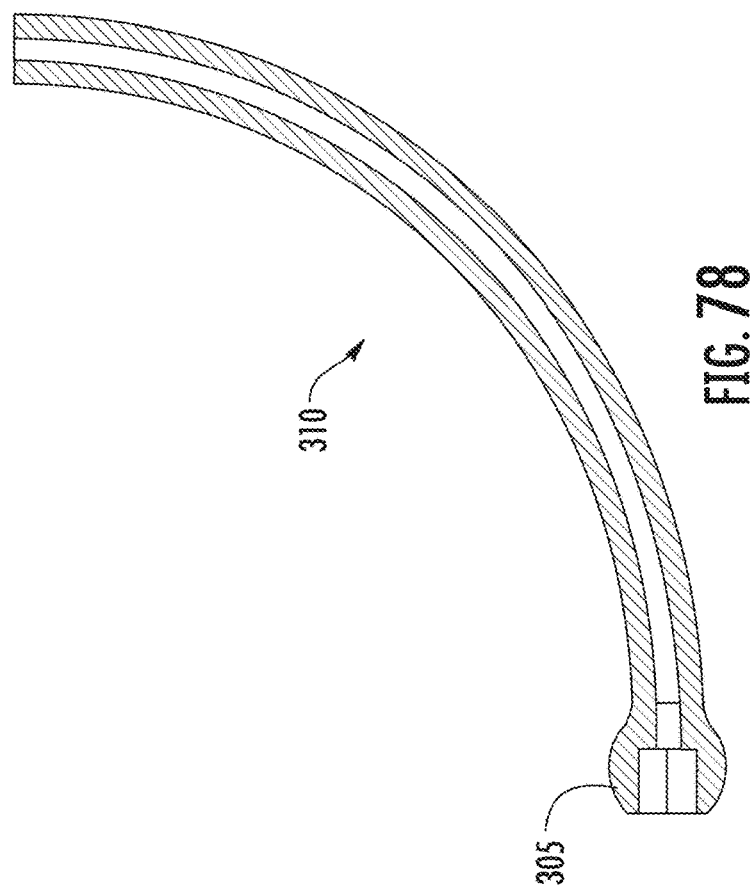
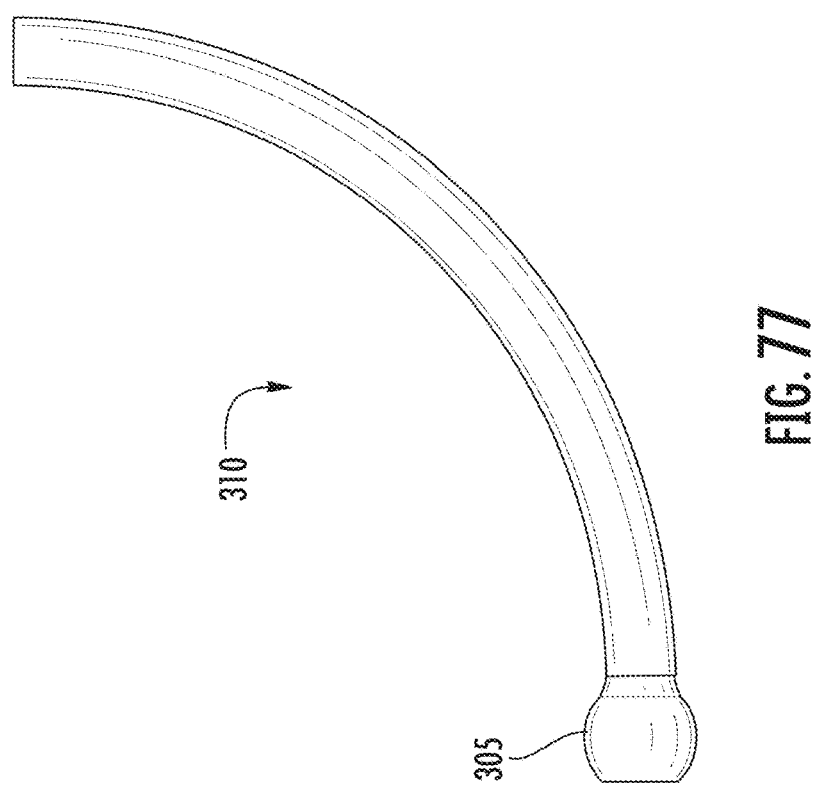

TRANSDISCAL SCREW

CROSS-REFERENCE TO RELATED APPLICATIONS

This application is a continuation of U.S. patent application Ser. No. 16/435,886, filed Jun. 10, 2019, now granted as U.S. Pat. No. 11,291,489, which is a continuation of U.S. patent application Ser. No. 15/105,210, filed Jun. 16, 2016, now granted as U.S. Pat. No. 10,314,631, which is a 371 national phase application of PCT App. No. PCT/US2014/070899, filed Dec. 17, 2014, which claims priority to the benefit of U.S. Prov. Pat App. No. 61/917,183, filed Dec. 17, 2013, all of which are incorporated herein by reference in their entireties.

TECHNICAL FIELD

This invention relates to systems and methods for treating bone within a skeletal structure, and more particularly transdiscal fixation of vertebral bodies.

BACKGROUND

A screw is defined as a composite device is placed into a medium in order hold two or more objects together. One of the most important parameters in describing a screw's overall performance is the pull-out resistance. It is defined as the minimal force required to pull-out the screw from the material, or to separate a screw from a nut. Usually, the screw's pull-out resistance per centimeter depends on parameters such as diameter of the screw and thread depth and pitch. Friction between the screw and medium is also important. In order to achieve higher pull-out resistance manufacturers typically modify the aforementioned parameters, such as increasing screw's diameter or thread depth and shape. However, a high installation torque is a trade-off for increased pull-out resistance. Also, increasing the screw size may not be an optimal solution since it requires more material to manufacture and a larger opening within target medium.

BRIEF DESCRIPTION OF THE DRAWINGS

Like reference numerals in the drawings designate corresponding parts throughout several views.

FIG. 41 is a plan view of an example flexible sleeve.
FIG. 42 is a cross-sectional view of the example flexible sleeve of FIG. 41.

FIG. 66 is a side view of an example core extension.

FIG. 67 is a perspective view of the example core extension of FIG. 66.

FIG. 68 is a perspective cross-sectional view of the example core extension of FIG. 66.

FIG. 77 is a side view of an example core.

FIG. 78 is a side cross-sectional view of the example core of FIG. 77.

DETAILED DESCRIPTION

The present invention is directed to a transdiscal screw capable of following a non-linear configuration. By following a non-linear trajectory, the pull-out resistance of the screw is significantly increased. A non-linear screw trajectory can generate several advantages over linear screw trajectories. For example, a non-linear screw can be used to hold two or more offset objects where the screw follows an arc-shaped path. In contrast, a linear screw's optimal approach is orthogonal to the contact surface of the screw. However, in some cases, especially in surgical situations, an orthogonal approach is prevented by outside or anatomical constraints. On the other hand, the non-linear trajectory of a curved screw can be placed orthogonal to the contact surface and still arrived at the intended final destination by alteration of the radius of the curve. In a particular example, a non-linear trajectory can be used to hold two adjacent vertebrae by using a transpedicular path. Systems and methods for providing a screw capable of following a non-linear configuration are described in more detail below.

Figure 1:
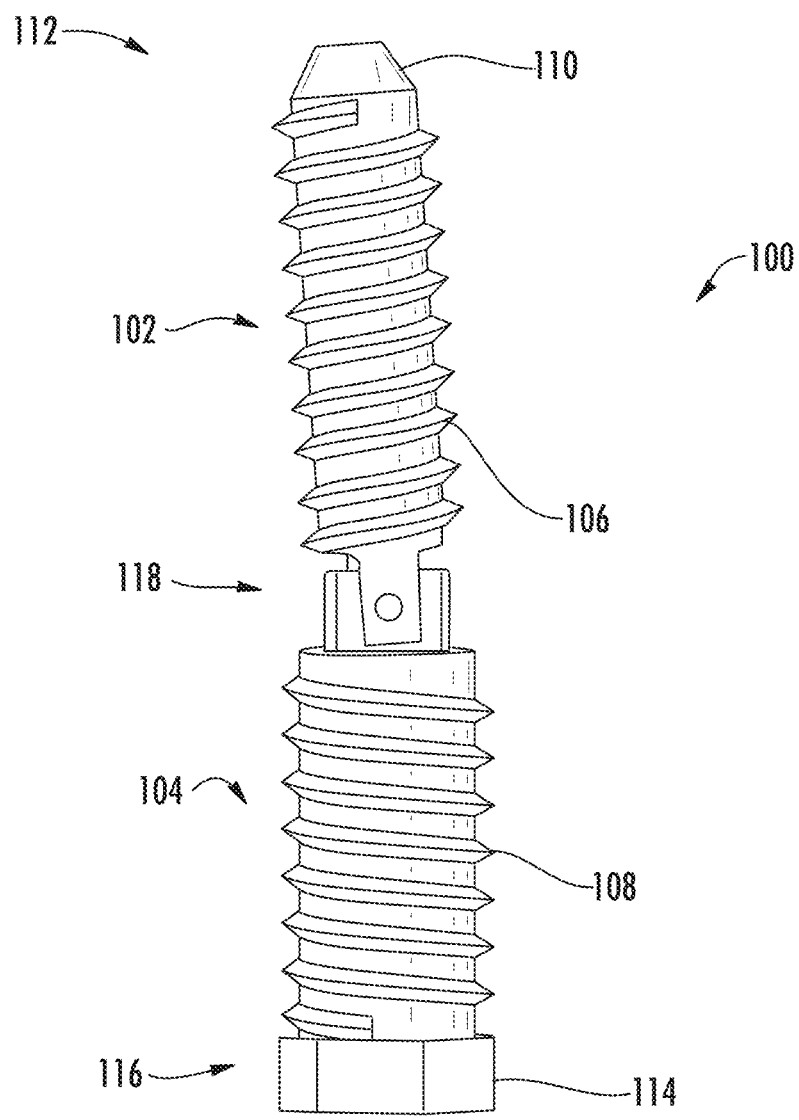
FIG. 1 is a plan view of an example screw assembly.
Figure 1A:
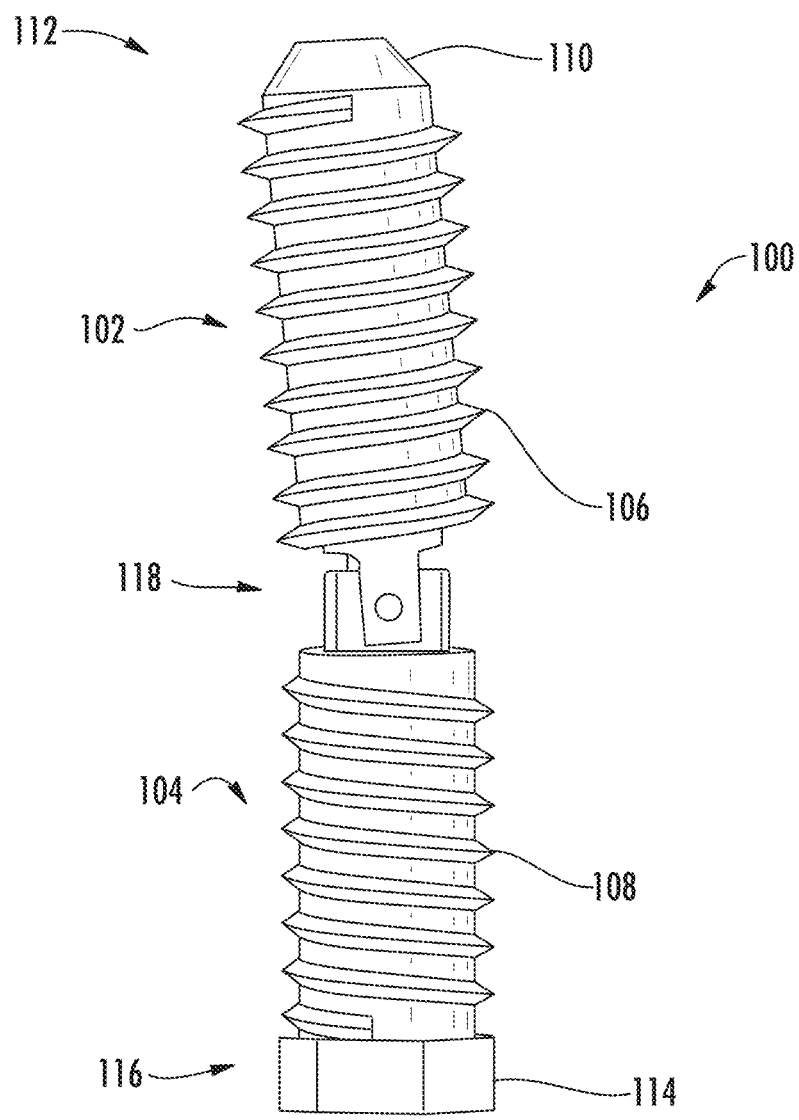
FIG. 1A is a plan view of an example screw assembly.
Figure 2:
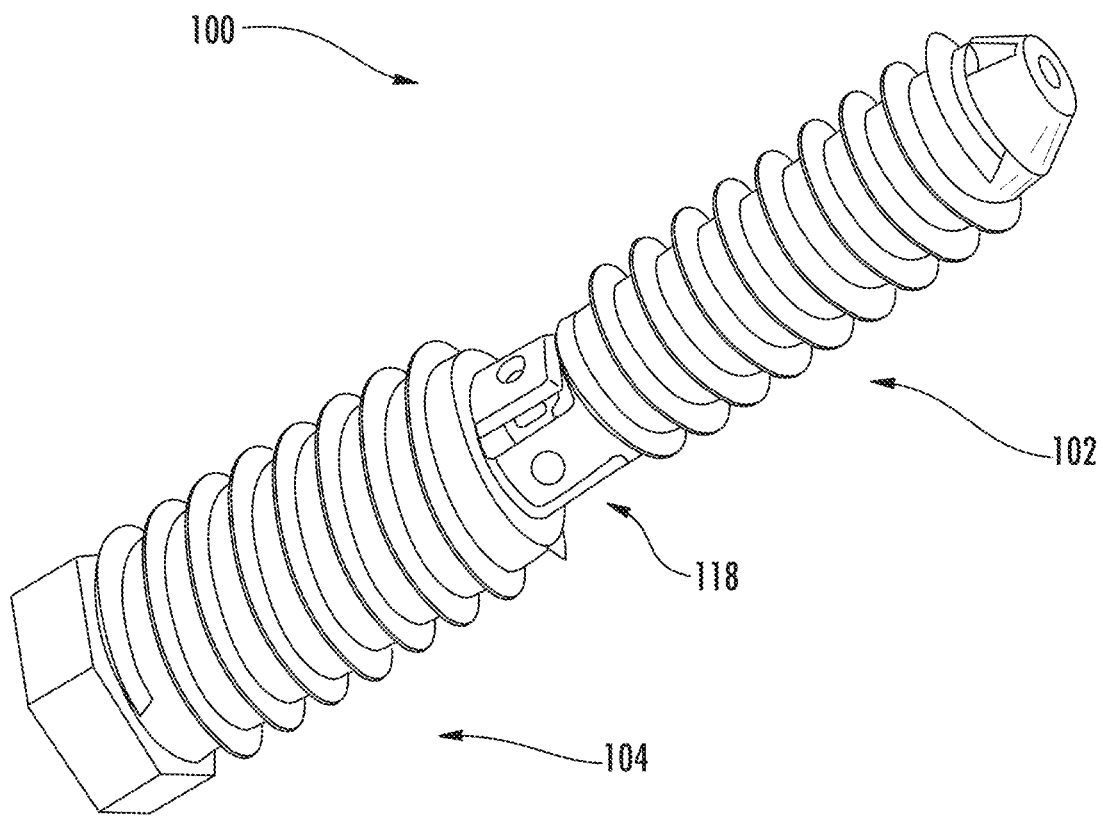
FIG. 2 is a perspective view of the example screw assembly of FIG. 1.

FIG. 1 provides a plan view of an example transdiscal screw assembly 100. The screw assembly 100 includes a first screw 102 and a second screw 104. Each of the screws include threads (106 and 108) for engaging a vertebral body. In general, the diameter of the first screw 102 will be equal to or less than the diameter of the second screw 104 to aid in positioning the screw assembly within a patient's body. For example, FIG. 1A provides a plan view of an example transdiscal screw assembly 100 with a first screw 102 and second screw 104, where the diameter of the first screw 102 is equal to the diameter of the second screw 104. Referring again to FIG. 1, the screw assembly 100 includes a tip 110 at the distal end 112 of the assembly and a connector 114 at the proximal end 116 of the assembly 100. FIG. 2 provides a perspective view of an example screw assembly 100.

Figure 3:
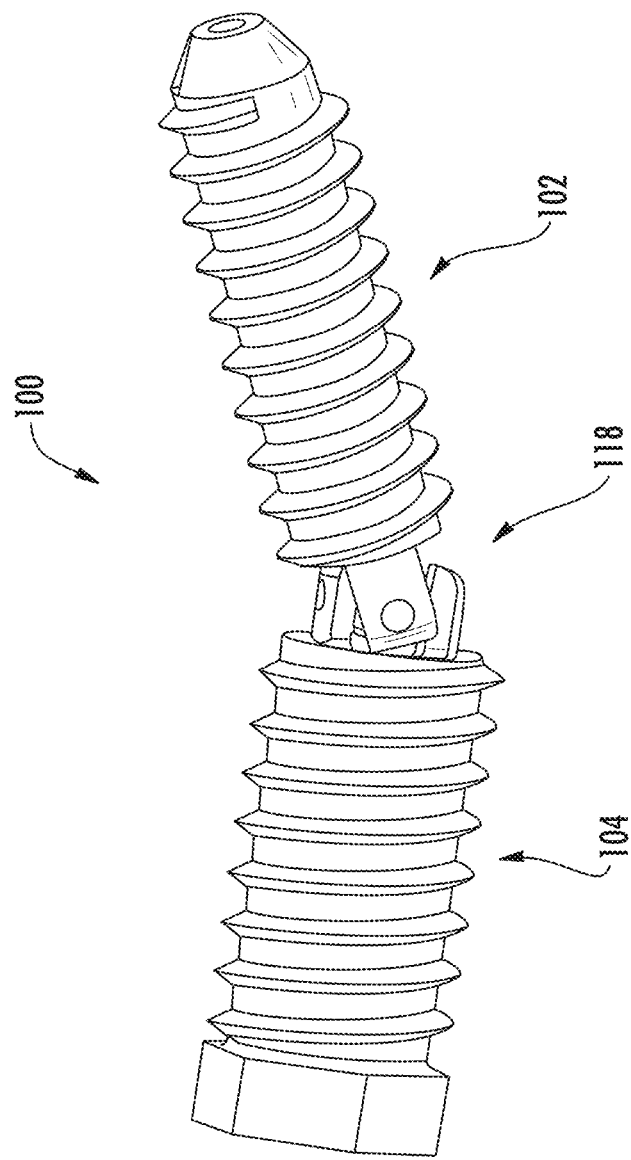
FIG. 3 is a perspective view of the example screw assembly of FIG. 1.
Figure 4:
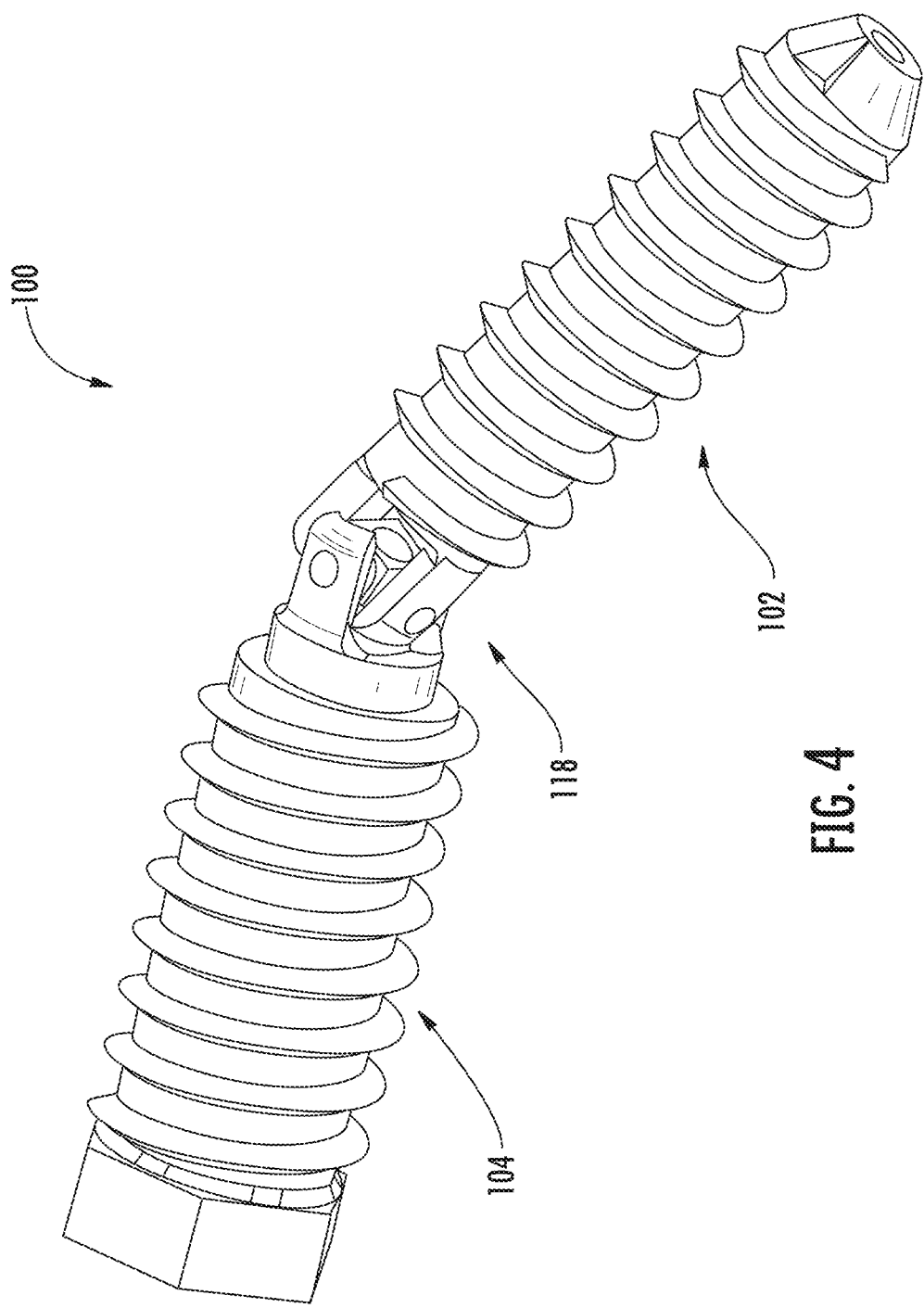
FIG. 4 is a perspective view of the example screw assembly of FIG. 1.
Figure 5:
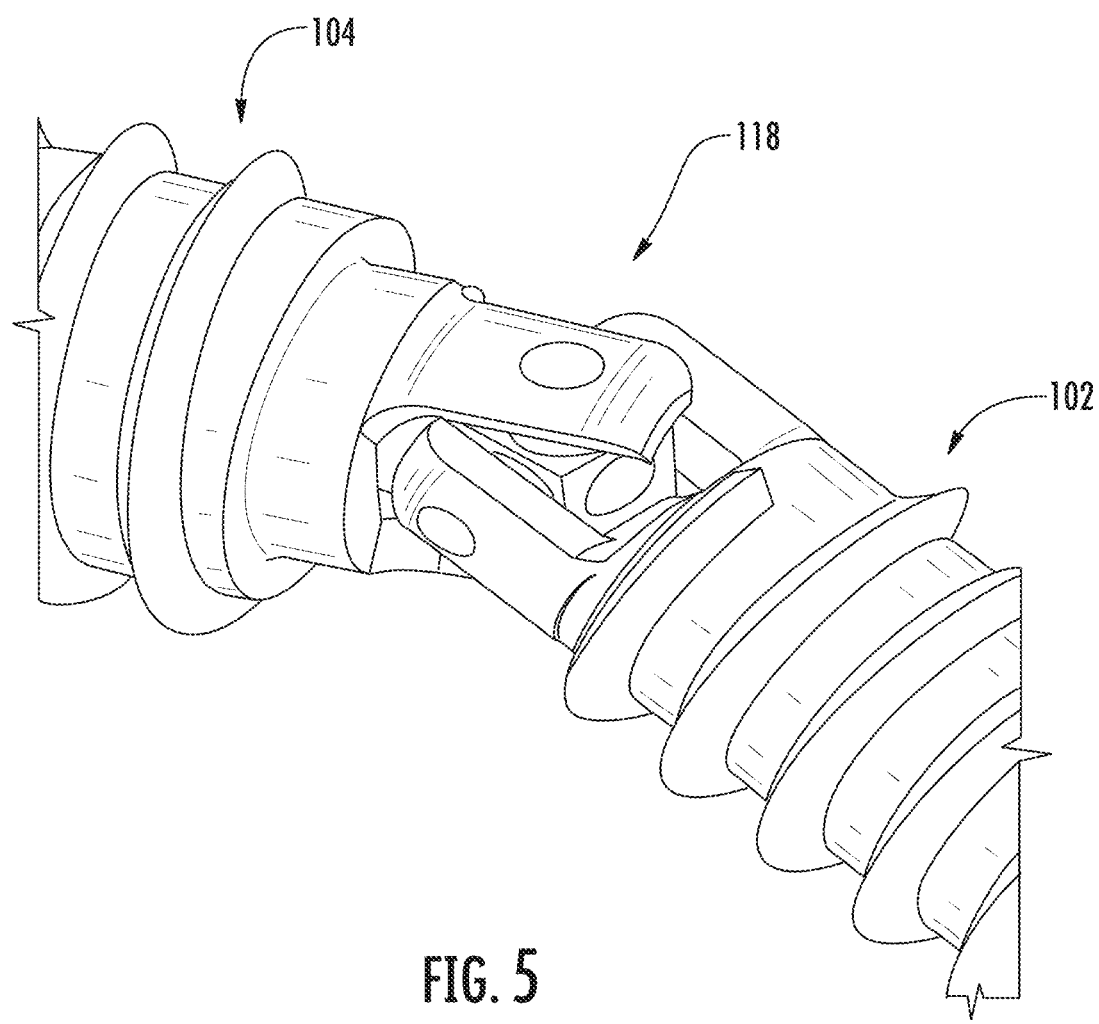
FIG. 5 is a partial perspective view of the example screw assembly of FIG. 1.

The first screw 102 and the second screw 104 are coupled at a joint 118 that provides an articulated coupling between the first screw 102 and the second screw 104. The joint 118 also allows for the transmission of torque to the (distal) first screw 102. FIGS. 3 and 4 provide perspective views of an example screw assembly 100 in various bent positions facilitated by movement of the joint 118. FIG. 5 provides a perspective view of joint 118 as assembled with the first screw 102 and the second screw 104. The joint 118 is configured to permit the first screw 102 and the second screw 104 to rotate independently of one another. Independent rotation of the first screw 102 and the second screw 104 allows for better purchase (engagement) of the respective screws within the vertebral body. An example joint 118 can include a poly-axial joint/coupling. An example joint 118 can include an ellipsoid joint. An example joint 118 can provide "universal joint" type movement of the first screw 102 with respect to the second screw 104. That is, the joint 118 provides the first screw 102 and the second screw 104 a freedom of movement in any direction while facilitating the transmission of motion.

Figure 6:
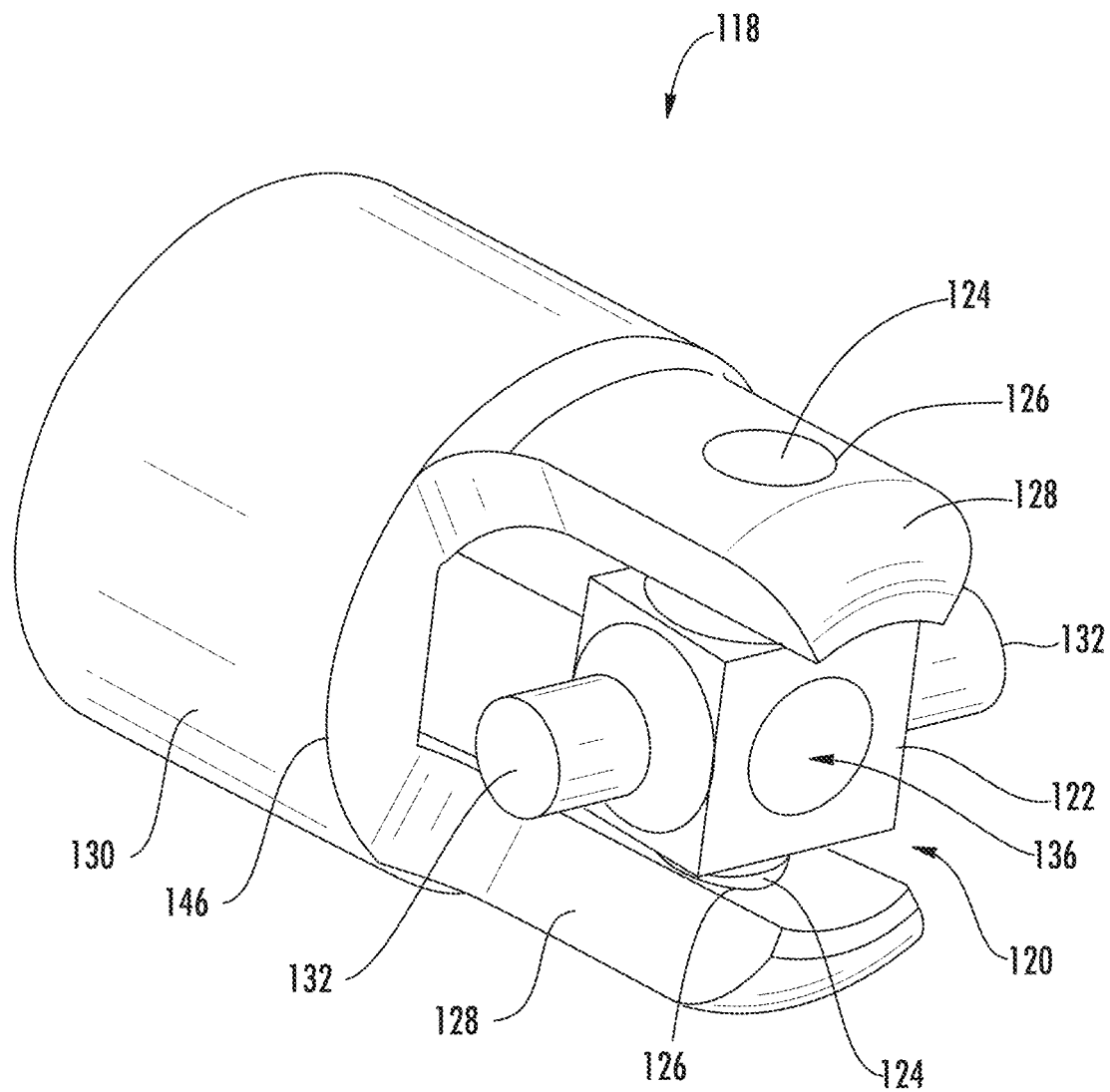
FIG. 6 is a perspective view of an example joint.
Figure 7:
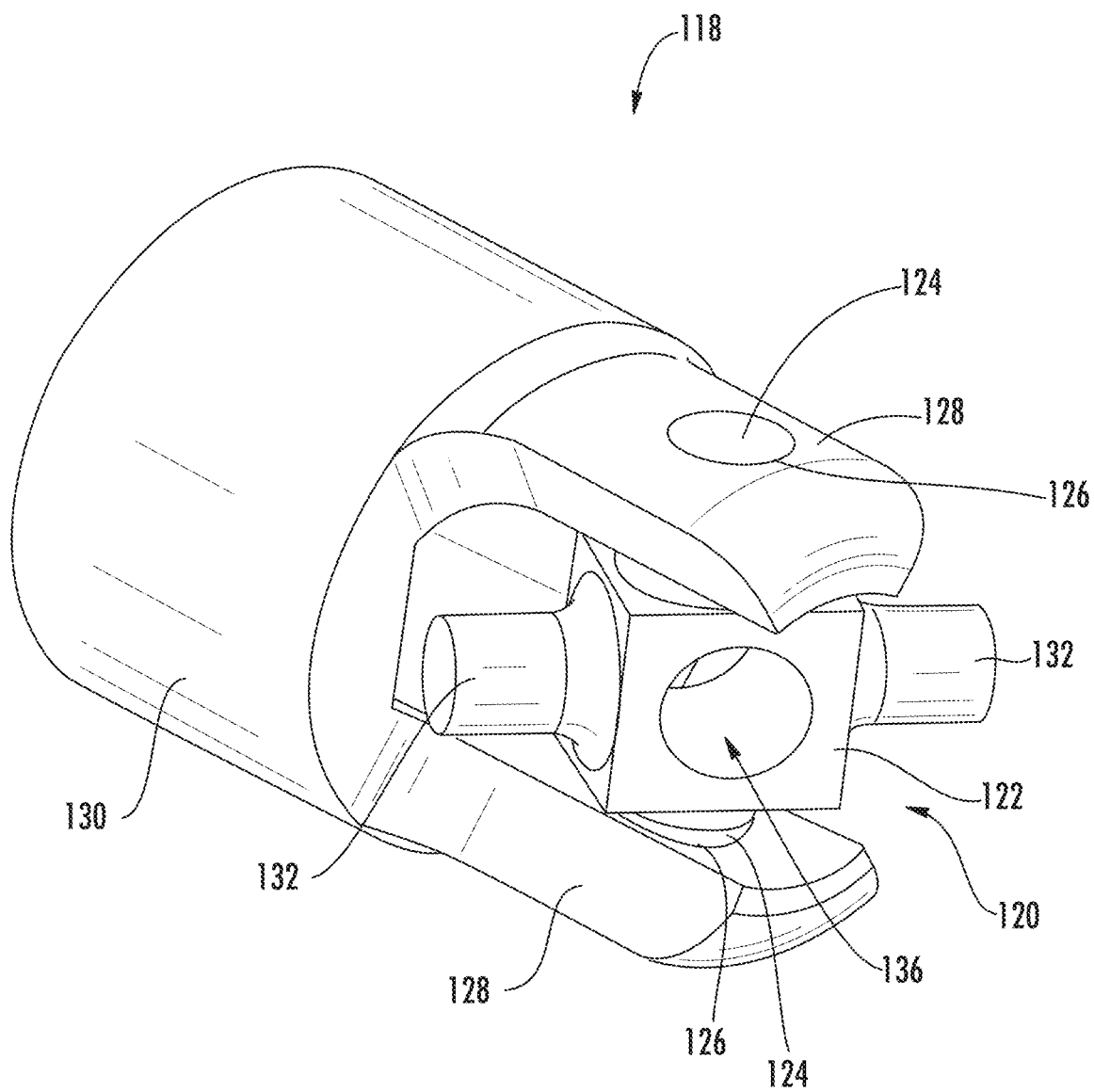
FIG. 7 is a perspective view of the example joint of FIG. 6.

FIGS. 6 and 7 provide perspective views of joint 118. The joint 118 includes a coupling 120 for attaching to the first screw 102. The coupling 120 is configured to provide freedom of movement between the first screw 102 and the joint 118. The coupling 120 includes a center element 122 rotatably coupled via projections 124 to openings 126 in the arms 128 extending from the base 130 of the joint 118. The center element 122 can also include a second set of projections 132 that are rotatably coupled to corresponding openings 134 in the first screw 102. The center element 122 can also include a central passage 136 extending through the center element 122. The central passage 136 can be sized and configured to accommodate a guide wire and/or tool.

Figure 8:
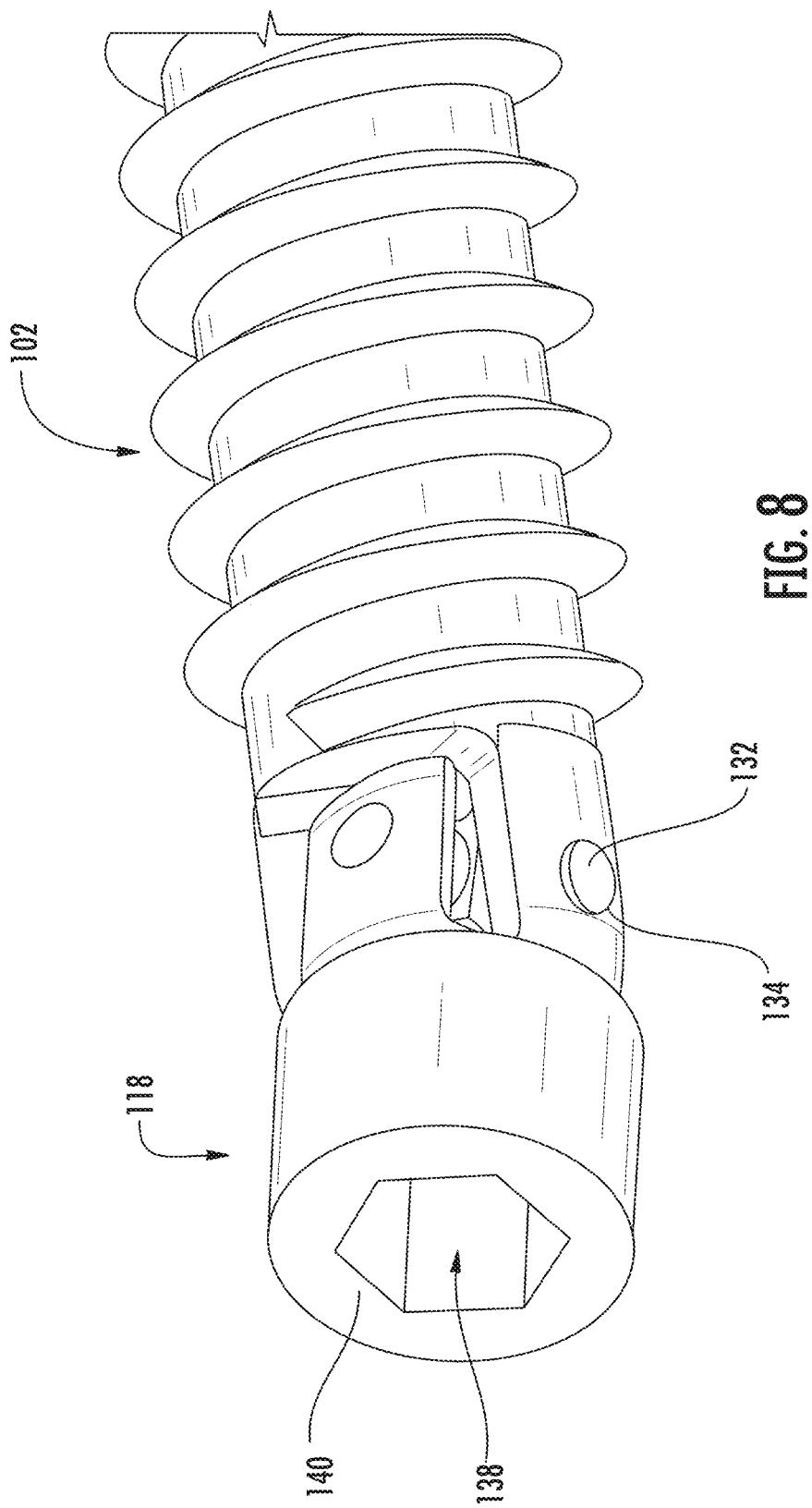
FIG. 8 is a partial perspective view of the example joint of FIG. 6 coupled to a screw.
Figure 9:
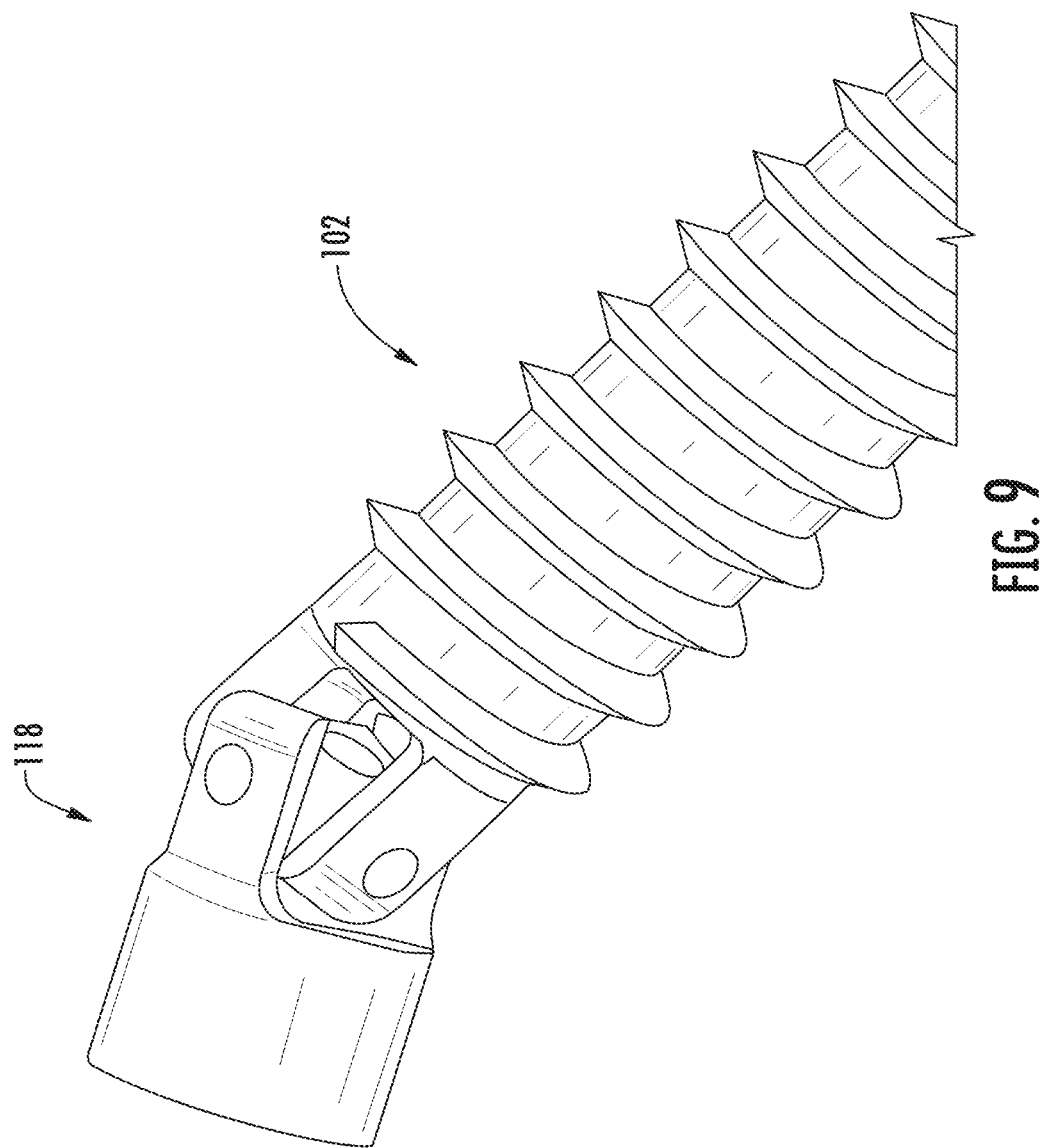
FIG. 9 is a partial perspective view of the example joint of FIG. 6 coupled to a screw.

FIGS. 8 and 9 provide perspective views of the joint 118 coupled to the first screw 102. The base 130 can include a central passage 138 extending through the base 130. The central passage 138 can be sized and configured to accommodate a guide wire and/or tool. The central passage 138 can also include a socket 140 sized and configured to receive a corresponding driver. The socket 140 permits rotational torque of a driver inserted through a central passage 142 of the second screw 104 to be transmitted into corresponding rotational movement of the socket 140 and first screw 102.

Figure 10:
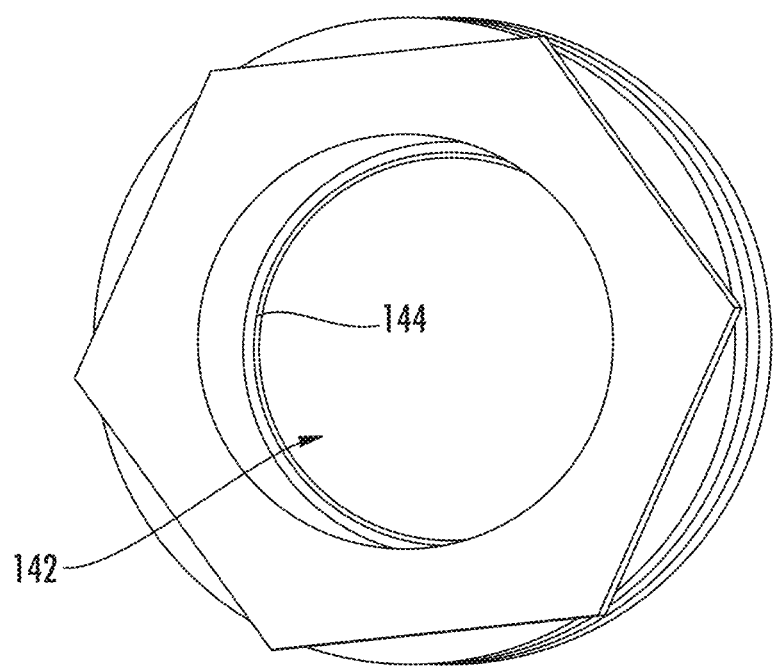
FIG. 10 is a partial perspective view of an example first screw.

To accommodate the independent rotation of the first screw 102 and the second screw 104, the joint 118 is configured to rotate within the central passage 142 of the second screw 104. For example, the outer diameter of the base 130 can be sized and configured to rotate freely within the central passage 142 of the second screw 104. As illustrated in FIG. 10, the second screw 104 can include a lip 144 extending from the internal surface of the central passage 142 at the distal end of the second screw 104. The lip 144 is sized and configured to engage a corresponding edge 146 of the joint 118 to maintain the base 130) within the central passage 142 of the second screw 104.

Figure 11:
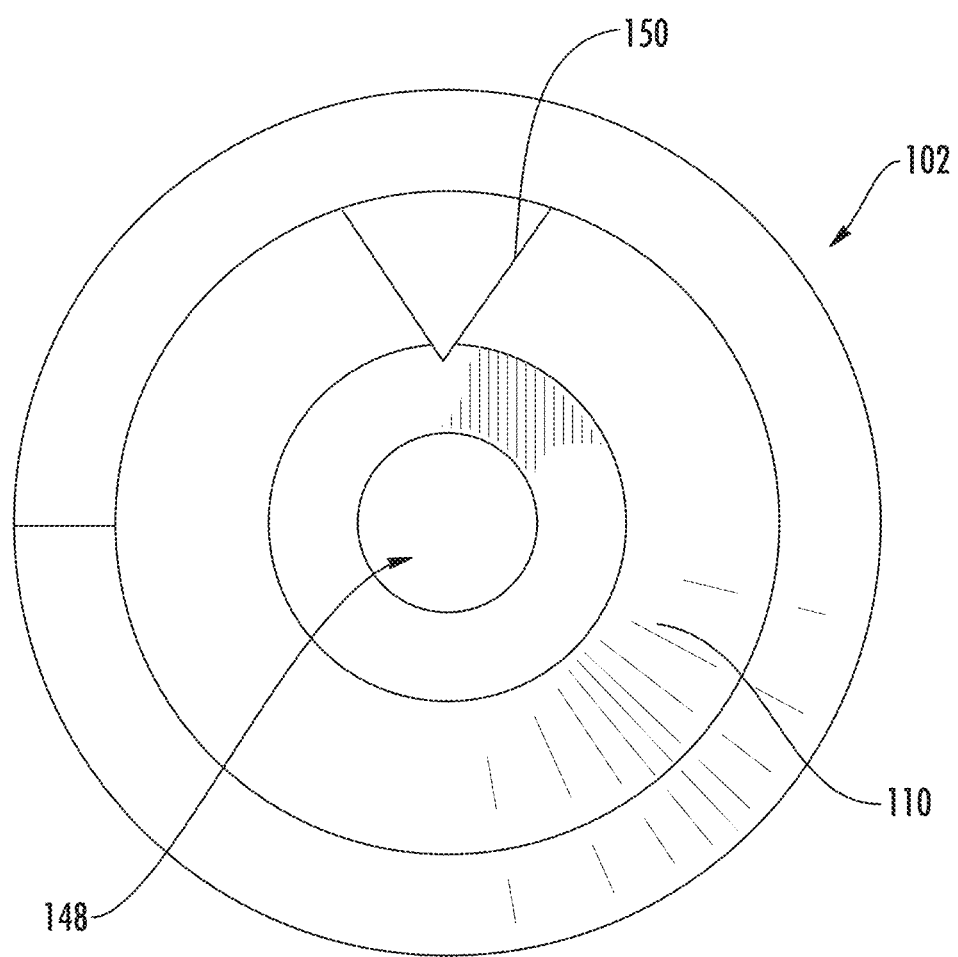
FIG. 11 is a plan view of the distal end of the example first screw.
Figure 12:
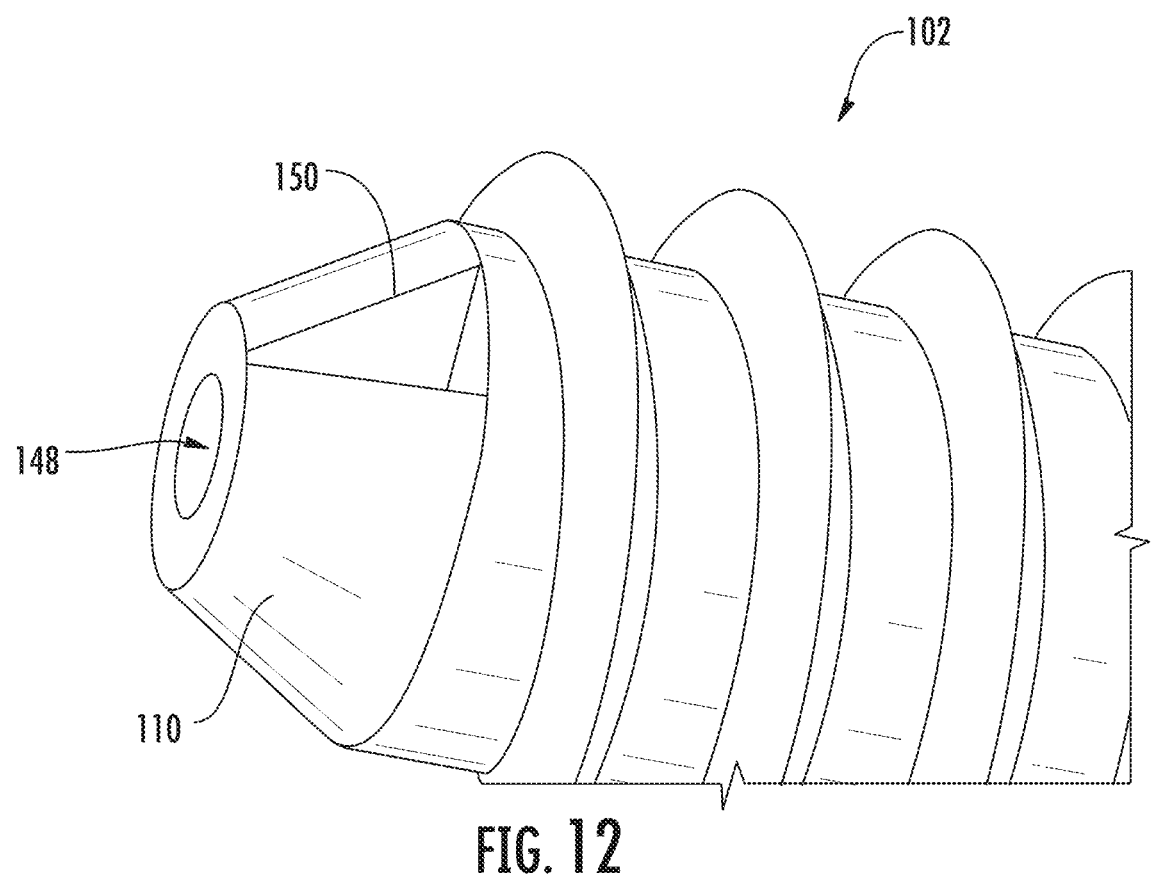
FIG. 12 is a partial perspective view of the distal end of the first screw of FIG. 11.

FIG. 11 provides a plan view of the distal end of the first screw 102. As illustrated in FIG. 11, the first screw 102 includes a central passage 148 extending through the first screw 102. The central passage 148 can be sized and configured to accommodate a guide wire and/or tool. FIG. 12 provides a perspective view of tip 110 located at the distal end of the first screw 102. The tip 110 can include a cutting edge 150. The cutting edge 150 can be configured to cut through vertebral bone and/or tissue as the first screw 102 is rotated and/or advanced within the patient's body.

Figure 13:
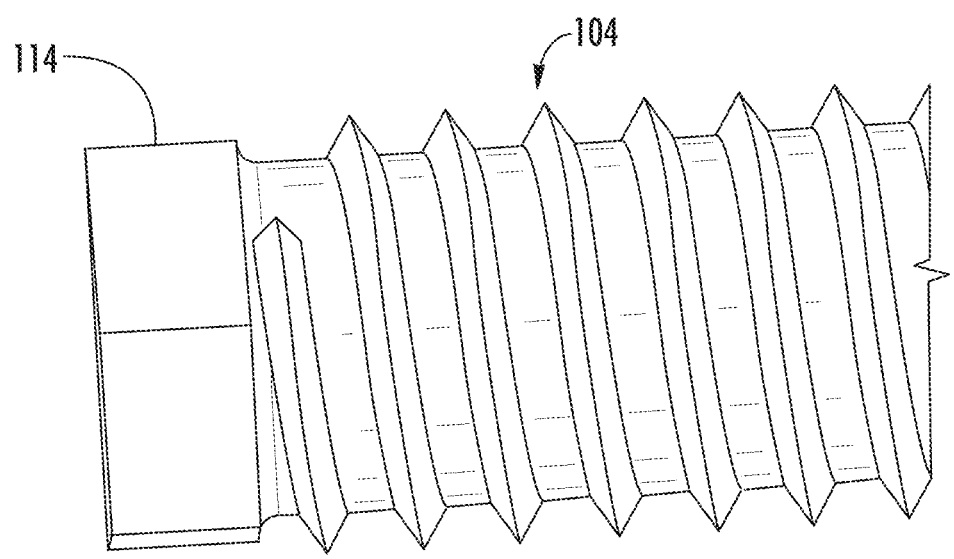
FIG. 13 is a plan view of the proximal end of an example second screw.

FIG. 13 provides a plan view of the proximal end of the second screw 104. As illustrated in FIG. 13, the second screw 104 can include a connector 114 sized and configured to engage with a corresponding driver. The connector 114 permits rotational torque of the corresponding driver to be transmitted into rotational movement of the second screw 104. As outlined above, the configuration of the joint base 130 within the central passage 142 of the second screw 104 permits rotation of the second screw 104 independent of rotation of the joint 118 and/or the first screw 102.

Figure 14:
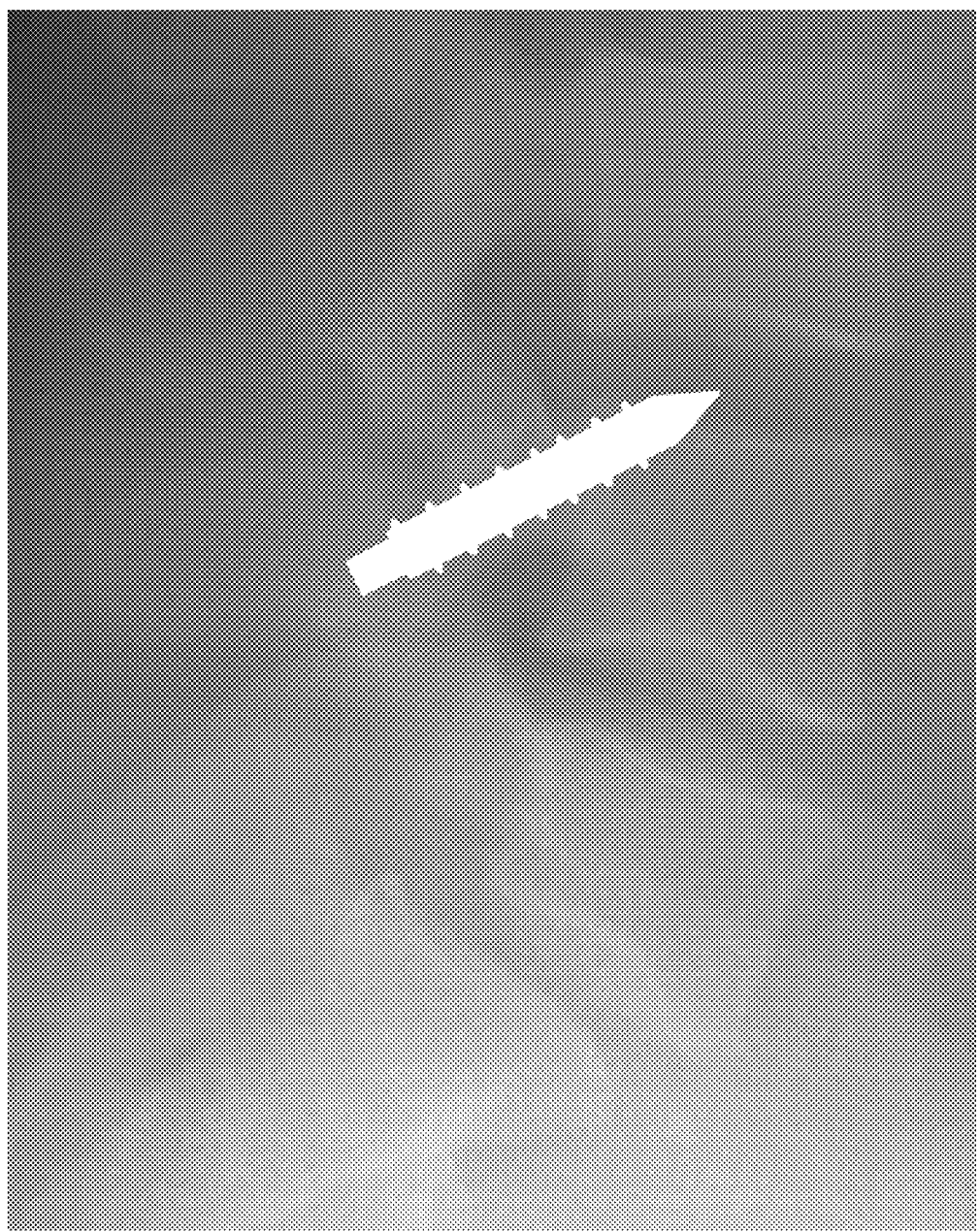
FIG. 14 illustrates a conventional single screw technique.
Figure 15:
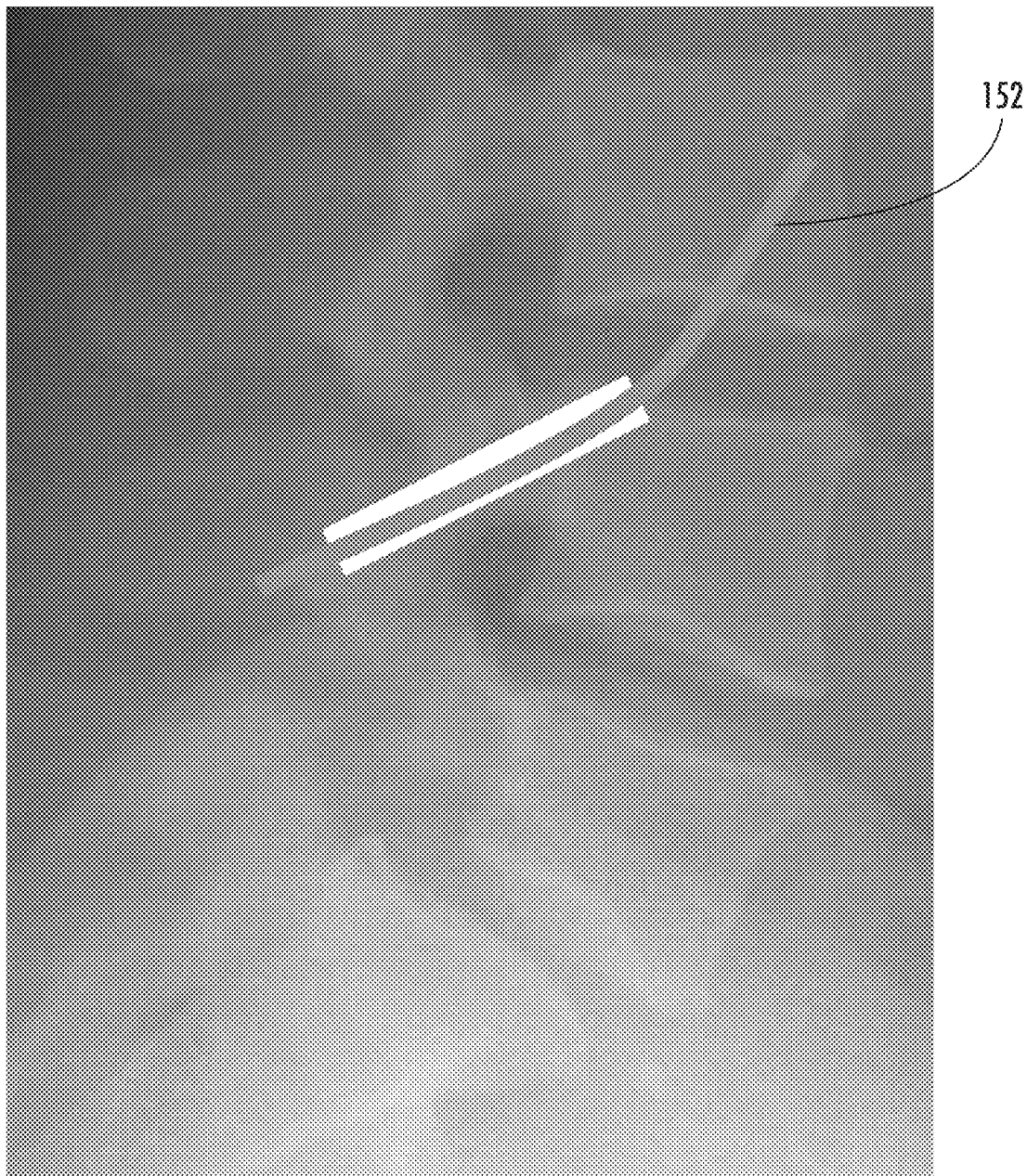
FIG. 15 illustrates an example desired path of a vertebral screw through multiple vertebral bodies.
Figure 16:
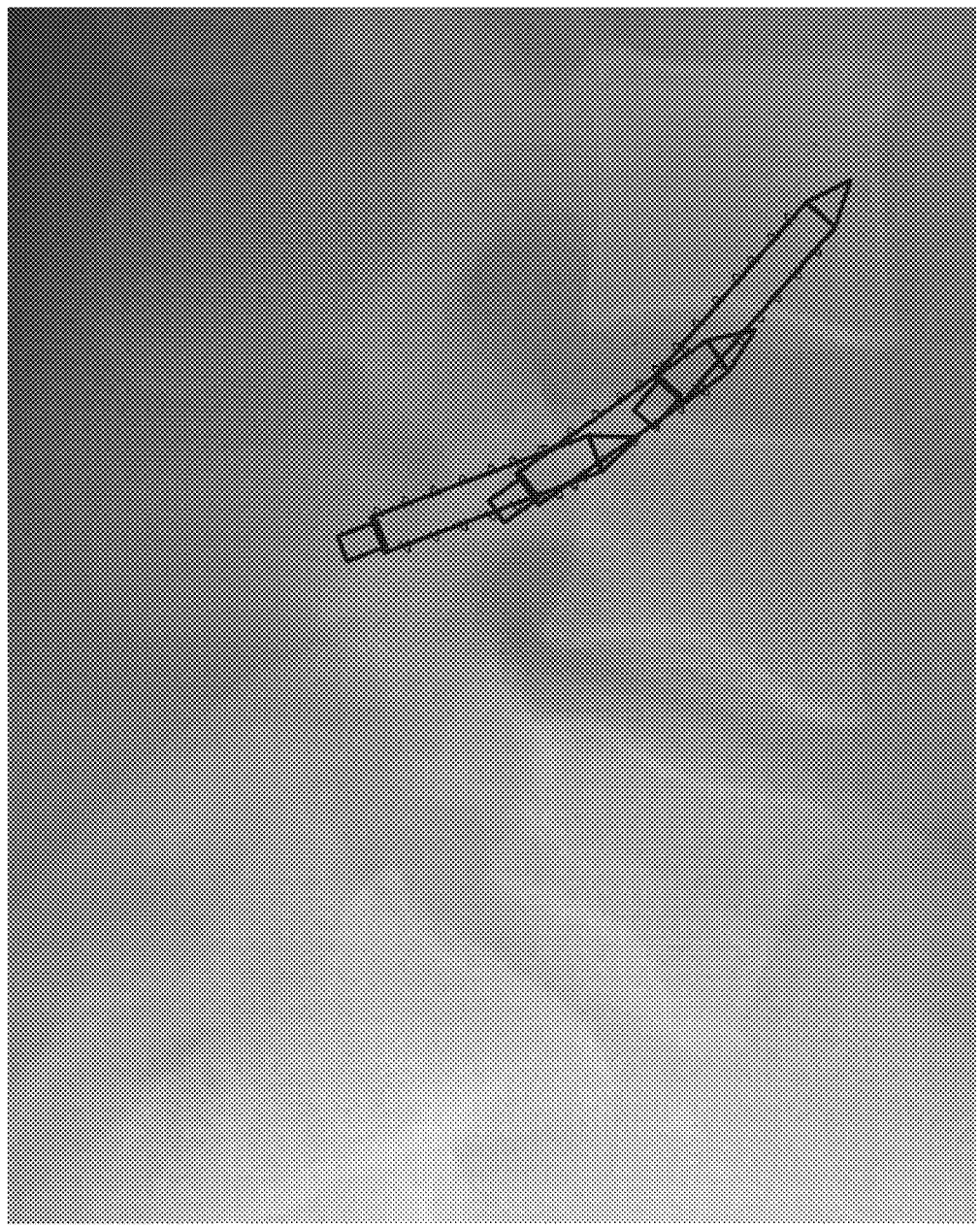
FIG. 16 illustrates the example desired path of a vertebral screw using a conventional single screw technique.

In contrast to current to single screw configurations, the screw assembly 100 can be advanced along a curved or angled path through multiple vertebral bodies. FIG. 14 provides an illustration of a conventional single screw technique. FIG. 15 provides an illustration of a desired path 152 of a vertebral screw through multiple vertebral bodies. As illustrated in FIG. 16, this desired path is not possible using conventional single screw models.

Figure 17:
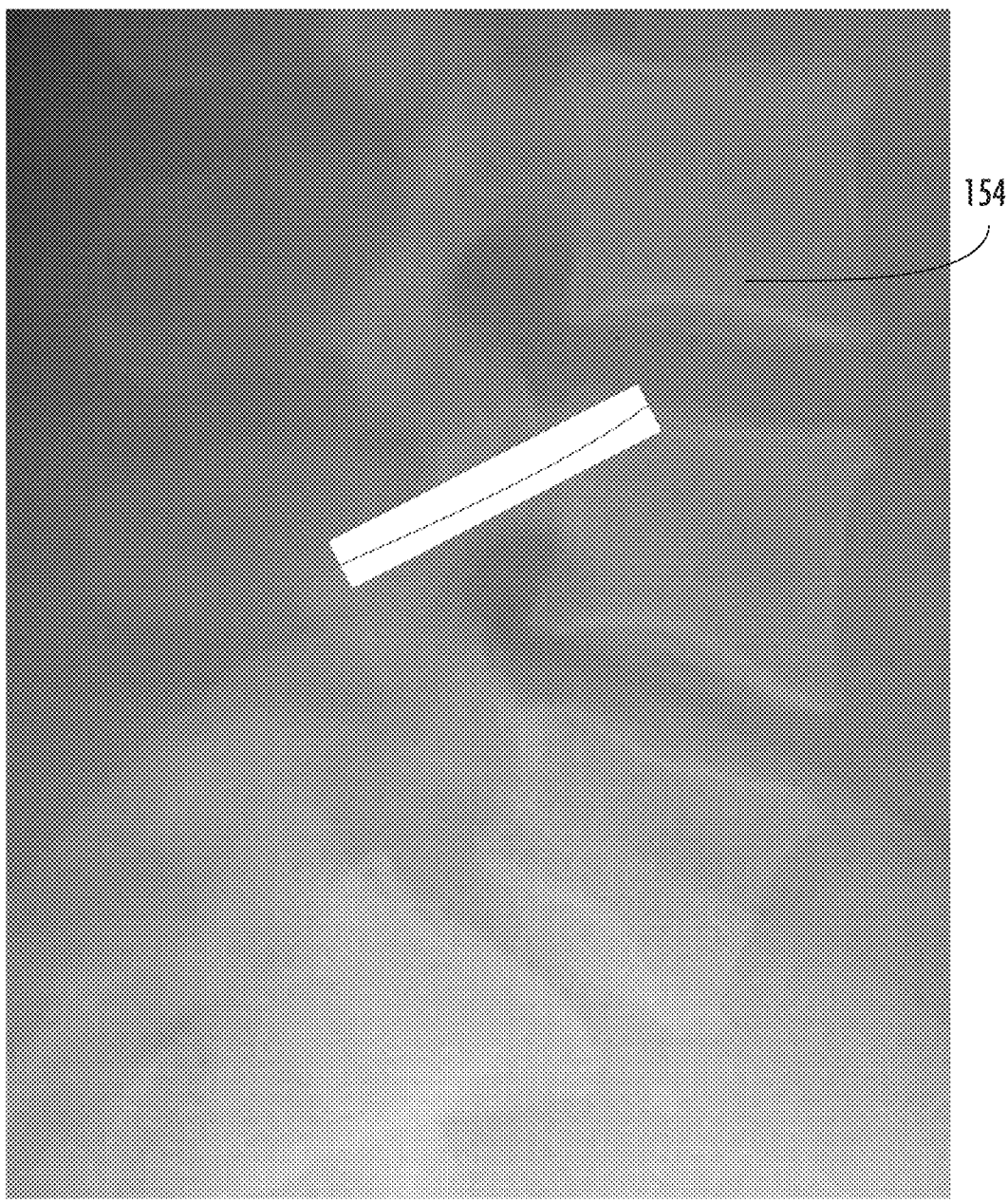
FIG. 17 illustrates a guide wire located along the example desired path.
Figure 18:
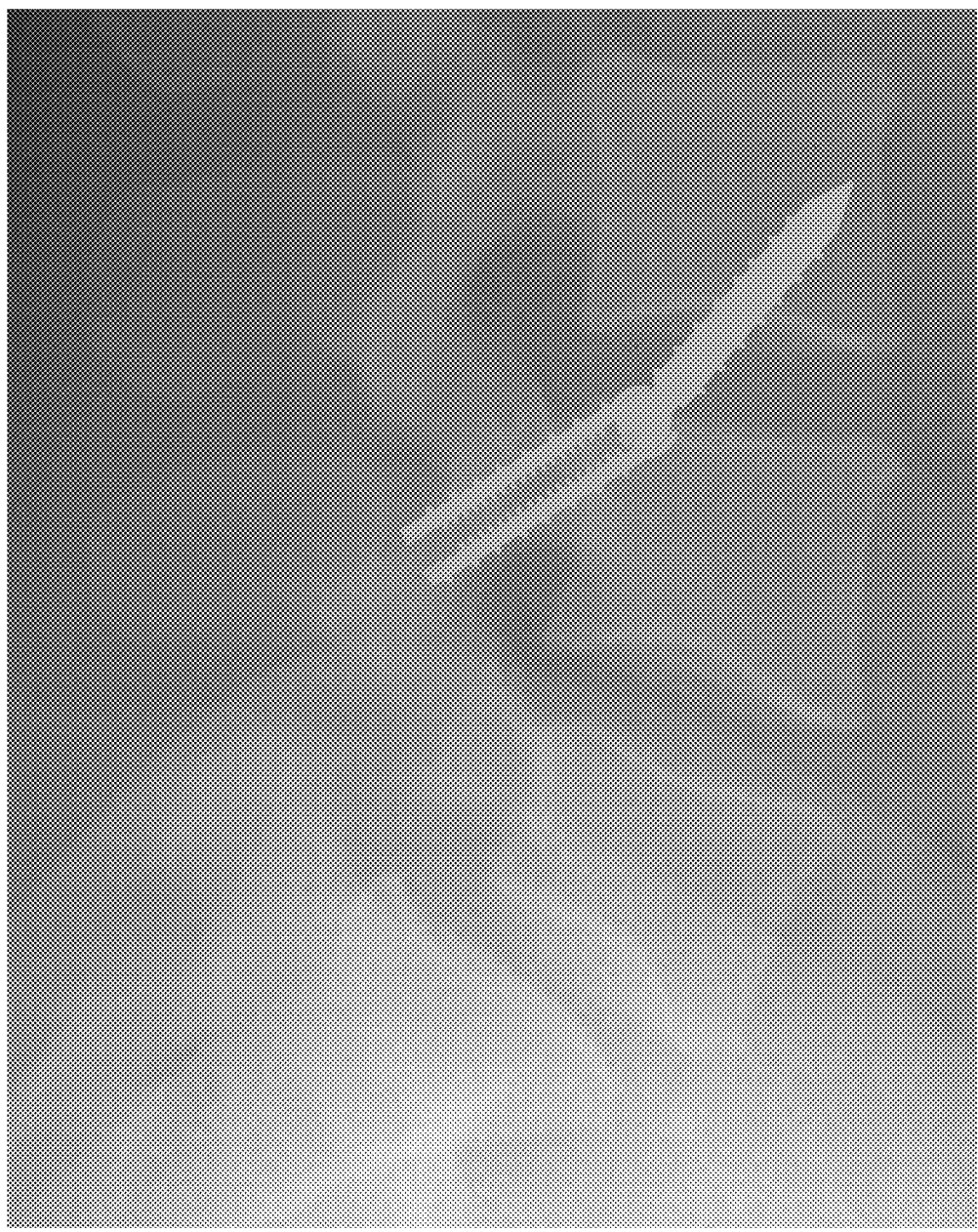
FIG. 18 illustrates an example screw assembly advanced along a guide wire of FIG. 17.

Using the present screw assembly 100, the transdiscal location of multiple vertebral screws can be achieved. FIG. 17 provides an illustration of a guide wire 154 located along a desired path within the patient. During operation, a medical professional can locate the guide wire 154 along a transdiscal or other desired path within the patient. The screw assembly 100 can be advanced along the guide wire 154 and the transdiscal path, as illustrated in FIG. 18.

Figure 19:
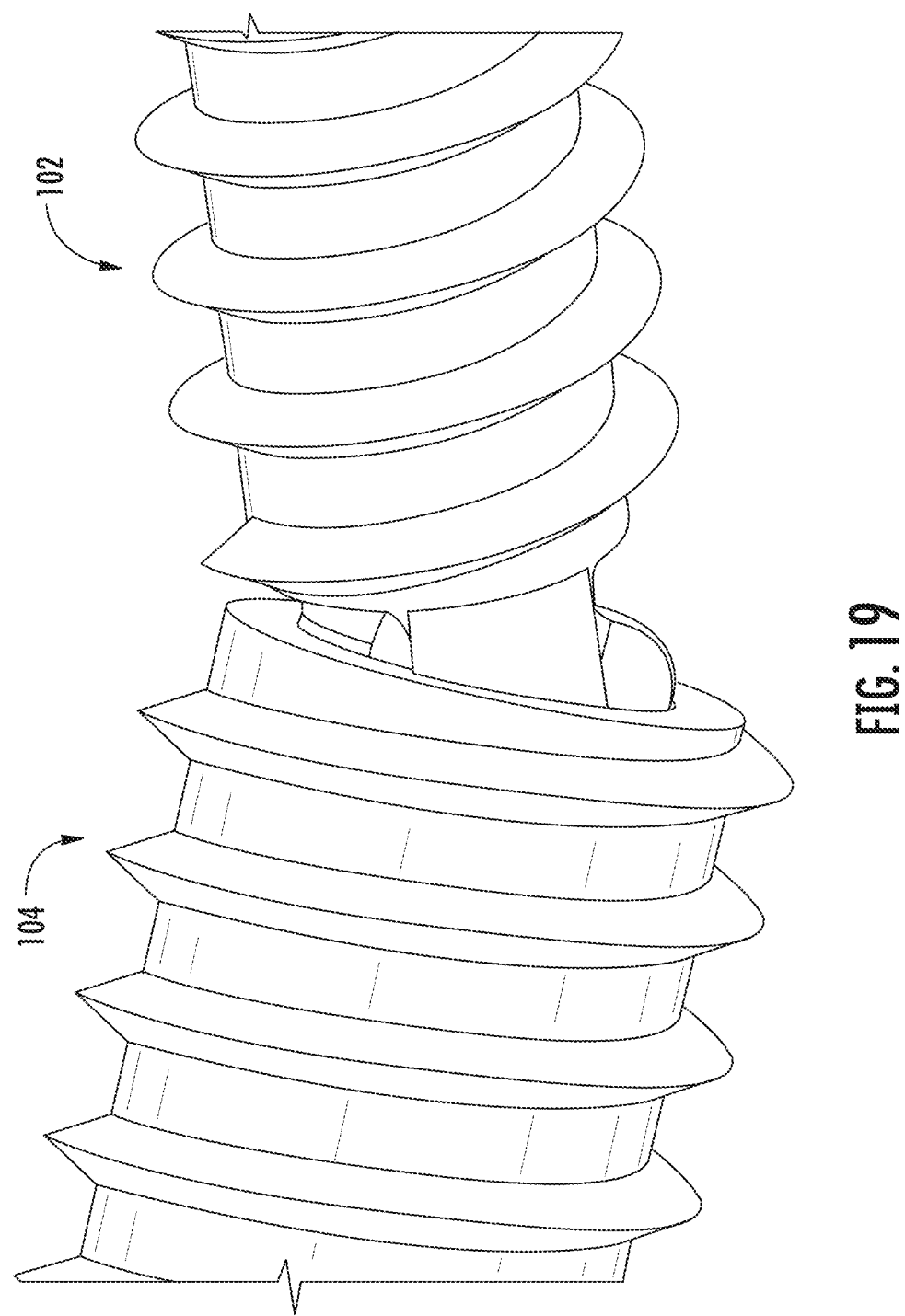
FIG. 19 is a partial perspective view of the example screw assembly of FIG. 1.

Once the screw assembly 100 is in the desired position, the central passage 142 second screw 104 is advanced over the arms 128 of the joint 118 as illustrated in FIG. 19. As the second screw 104 is advanced, the orientation and position of the first screw 102 with respect to the second screw 104 is fixed. In an example screw assembly 100, the second screw 104 can press or otherwise deform the arms 128 against the center element 122 and the wall of central passage 148 of the second screw 104.

In addition to securing and/or fusing adjacent vertebral bodies together, the screw assembly 100 can be used to modify the gap between the bodies before the screw assembly 100 is fixed in its final position. For example, the screw assembly 100 can be used to provide compression and/or decompression between vertebral bodies. Further disclosure of fusing/securing multiple vertebral bodies using one or more screws to enable compression and distraction to modify the gap between the bodies is provided in previously filed PCT Application Number PCT/US2012/058968, titled "Bone Fusion System" and corresponding U.S. Provisional Patent Application No. 61/543,482, titled "Bone Fusion System."

Figure 20:
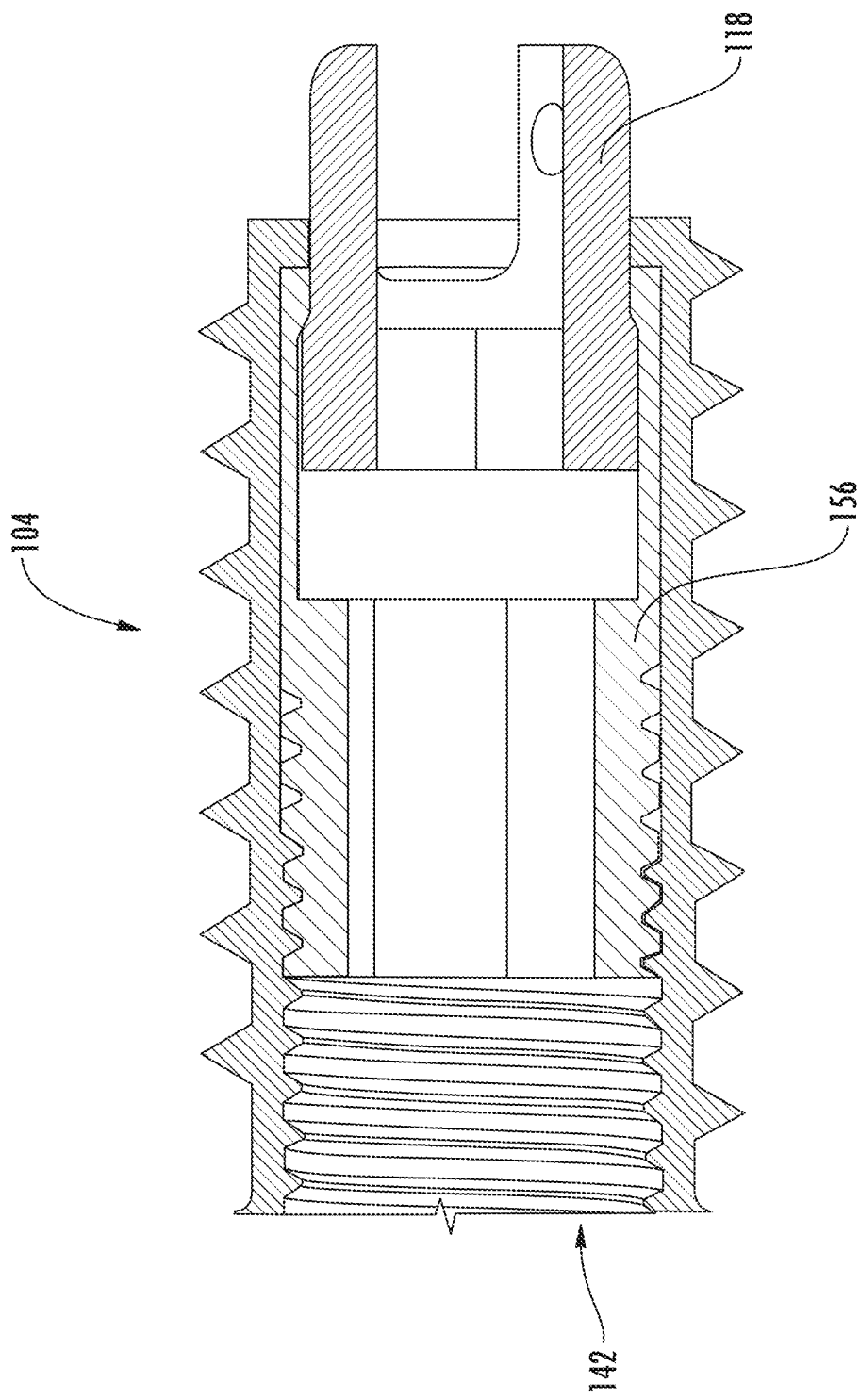
FIG. 20 is a cross-sectional view of the example second screw, joint and casing.
Figure 21:
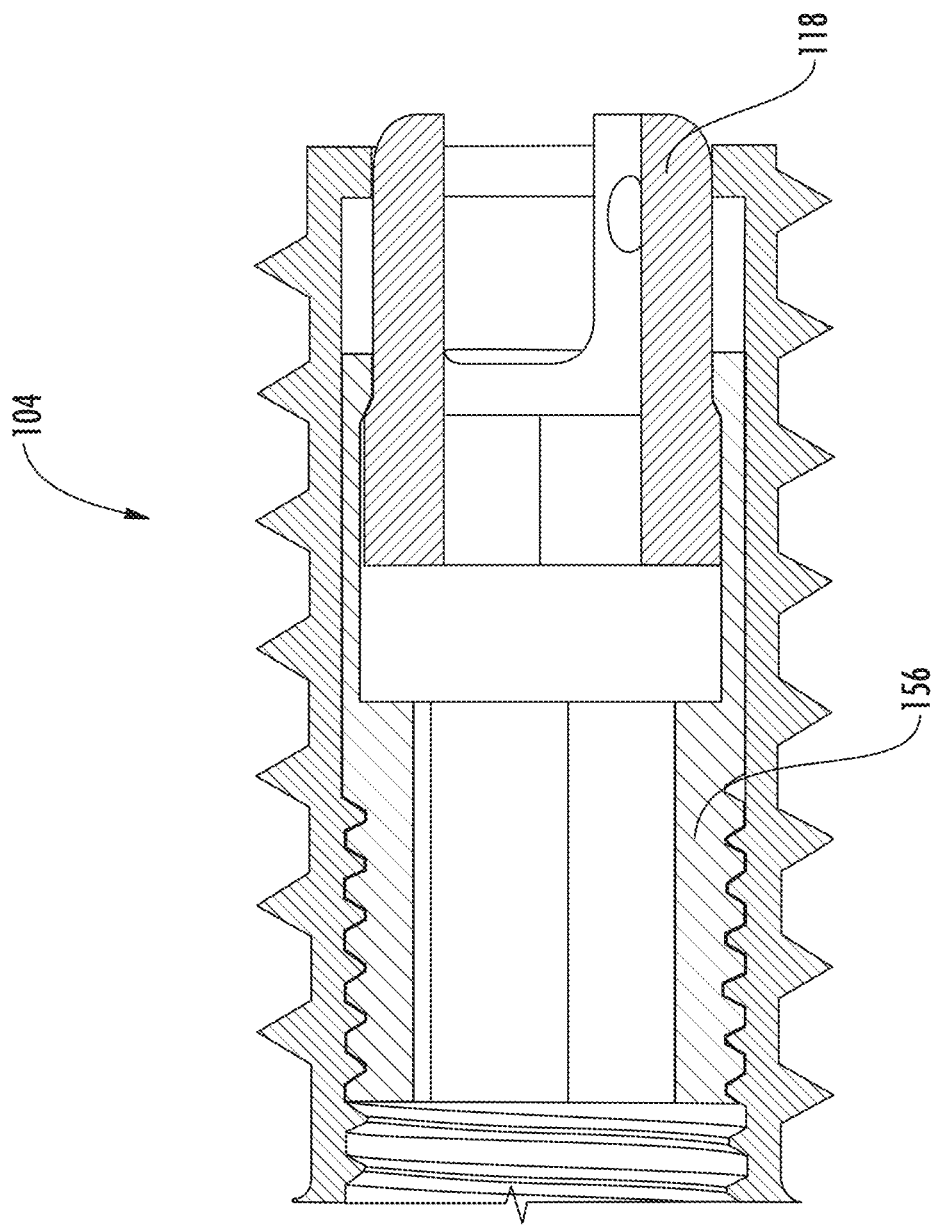
FIG. 21 is a cross-sectional view of the example second screw, joint and casing of FIG. 20.
Figure 22:
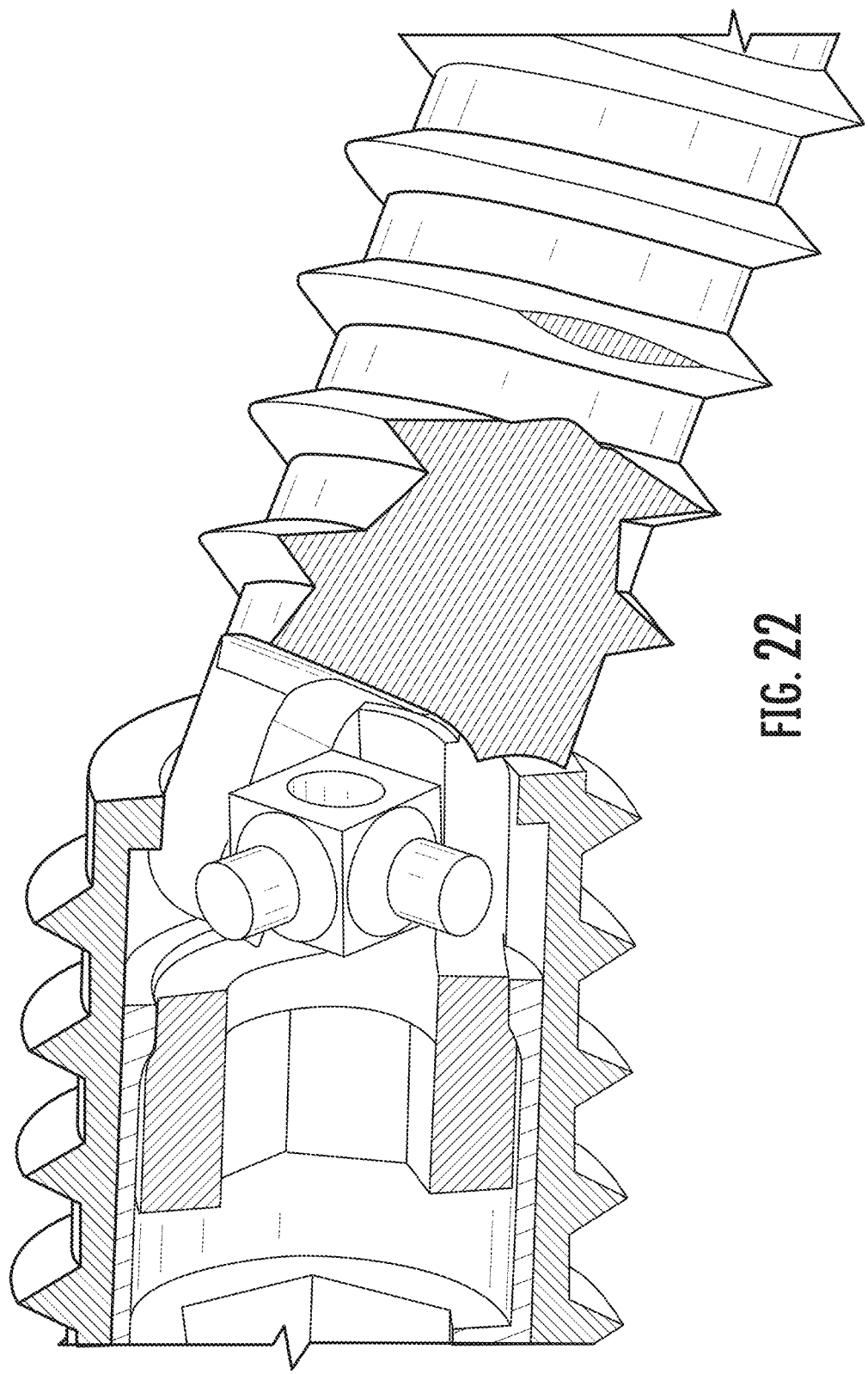
FIG. 22 is a partial cross-sectional view of the example second screw, joint and casing of FIG. 20.

To facilitate compression, a casing 156 can be provided within the central passage 142 of the second screw 104 to enable longitudinal movement of the first screw 102 with respect to the second screw 104. FIG. 20 illustrated a cross-sectional view of the second screw 104 including the joint 118 and the casing 156. The joint 118 is seated within the casing 156 in an unlocked position, that is, the joint 118 is free to move axially and rotate with respect to the casing 156. The casing 156 can be rotated, engaging threads on the central passage 142 of the second screw 104, thereby causing the casing 156 to move away from the joint 118 and towards the proximal end 116 of the assembly 100. As the casing 156 moves towards the proximal end 116 of the assembly, as illustrated in FIG. 21, the casing 156 engages the joint 118 and thereby pulls the joint 118 towards the proximal end 116. The joint 118, and thereby the first screw 102, can be moved in a direction towards the proximal end 116 of the assembly and, as a result, the two vertebras are moved together, i.e., compressed. In the compressed state, the second screw 102 can advanced over the arms 128 of the joint 118 and fix the location of the first screw 102 and the second screw 104 with respect to each other, as illustrated in FIG. 22.

Figure 23:
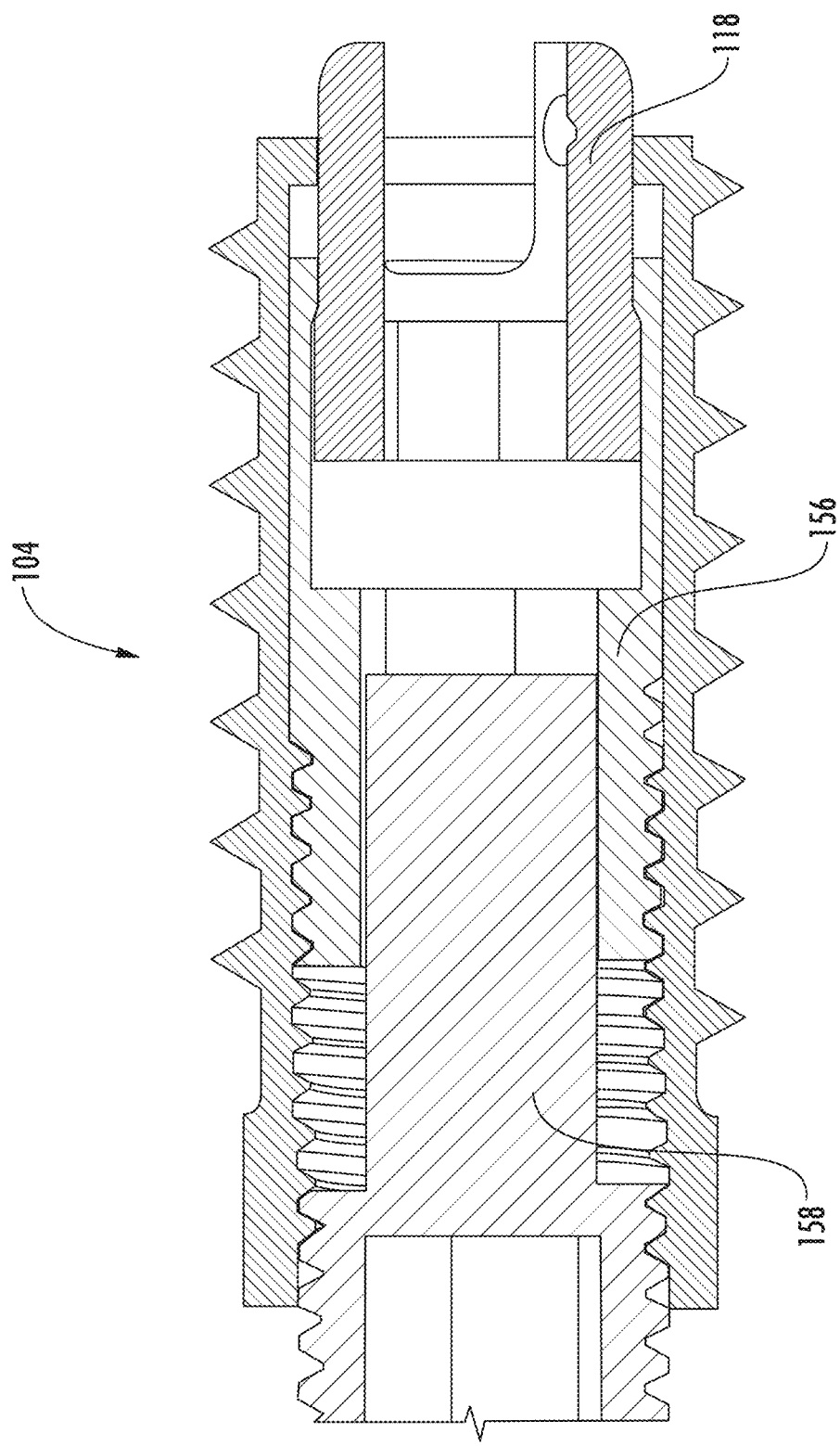
FIG. 23 is a partial cross-sectional view of the example second screw, joint, casing and lock of FIG. 20.
Figure 24:
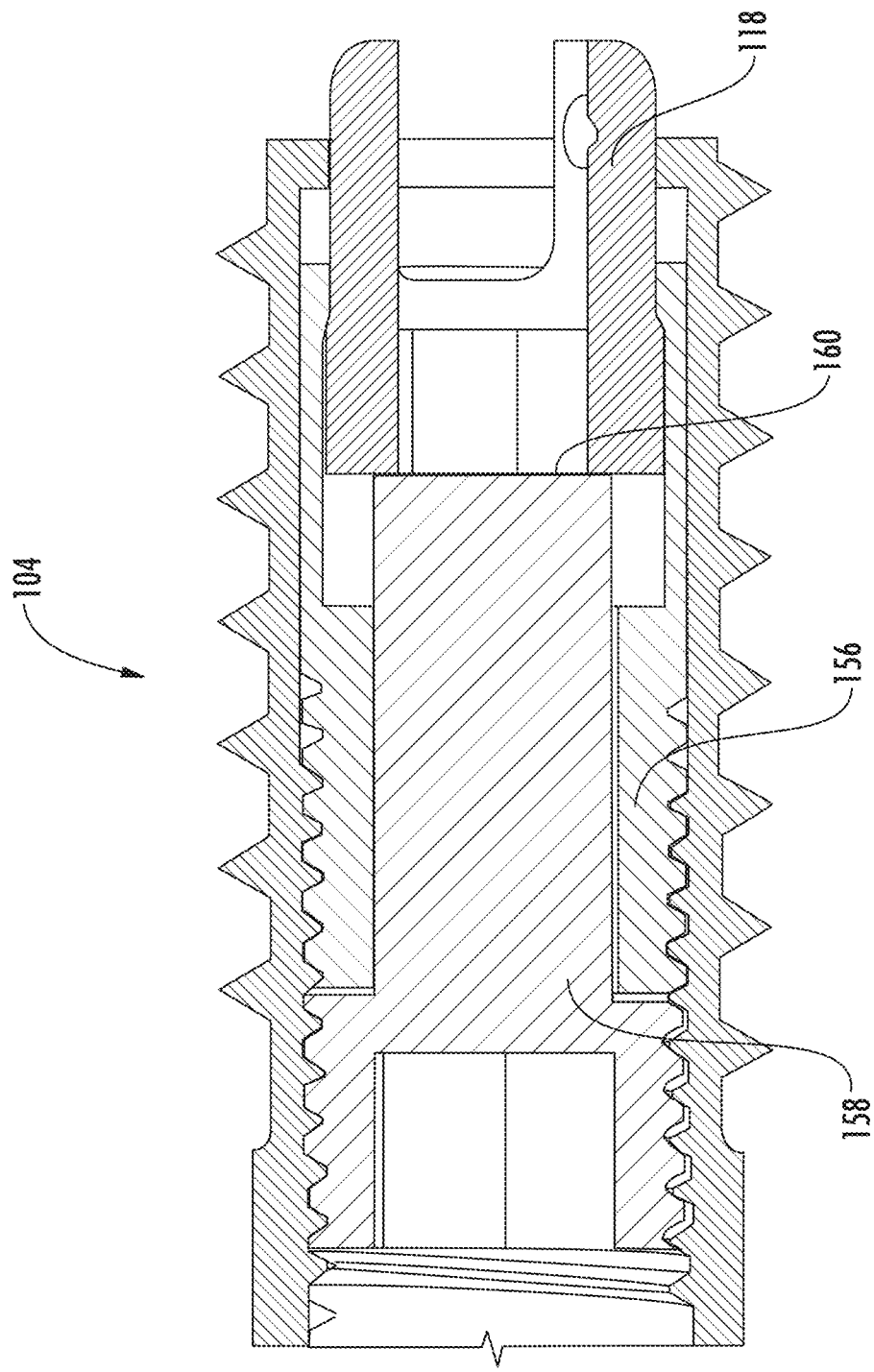
FIG. 24 is a partial cross-sectional view of the example second screw, joint, casing and lock of FIG. 20.

In an example assembly 100, a lock 158 can be inserted into the central passage 142 of the second screw 104 to engage the proximal surface of the joint 118. FIGS. 23 and 24 provide and illustrations of the lock 158 as it is advanced into the central passage 142. The lock 158 can be advanced until the distal surface 160 of the lock 158 engages and/or contacts the joint 118 to prevent further movement of the joint 118 towards the proximal end 116.

Figure 25:
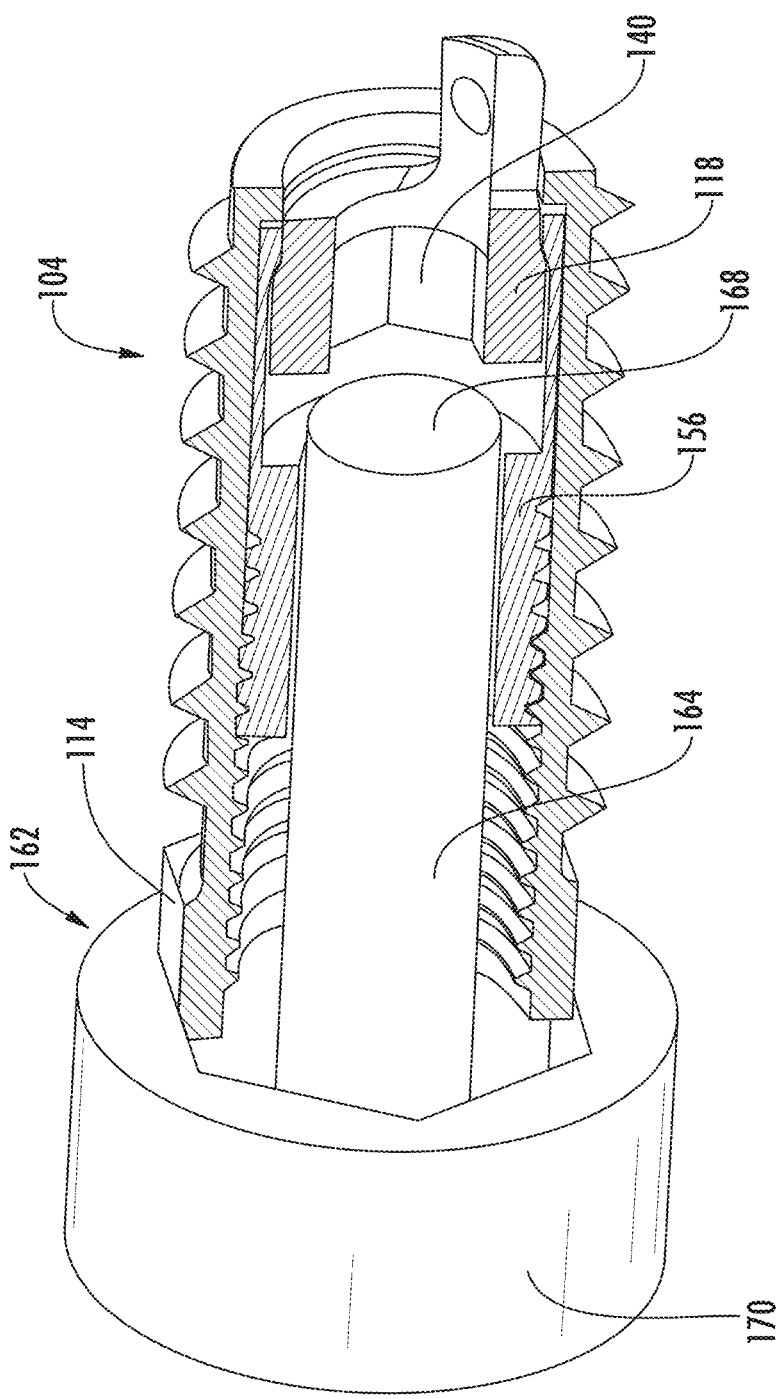
FIG. 25 is a partial cross-sectional view of the second screw including a driving tool.

To facilitate decompression, a driving tool 162 can be inserted into the central passage 142 of the second screw 104. Decompression can occur before the screw assembly 100 and/or the first screw 102 is fully seated into the vertebral body. FIG. 25 provides a cross-sectional view of the second screw 104 including the driving tool 162. The central shaft 164 of the driving tool 162 can be positioned inside the central passage 142 of the second screw 104 and the central passage of the casing 156. The distal tip 168 of the central shaft 164 can be sized and configured to engage the socket 140 of the joint 118. The driving tool 162 can include a head 170 sized and configured to engage the connector 114 of the second screw 104. In a further example, the head 170 can be sized and configured to engage the surface of the proximal end of the second screw 104.

Figure 26:
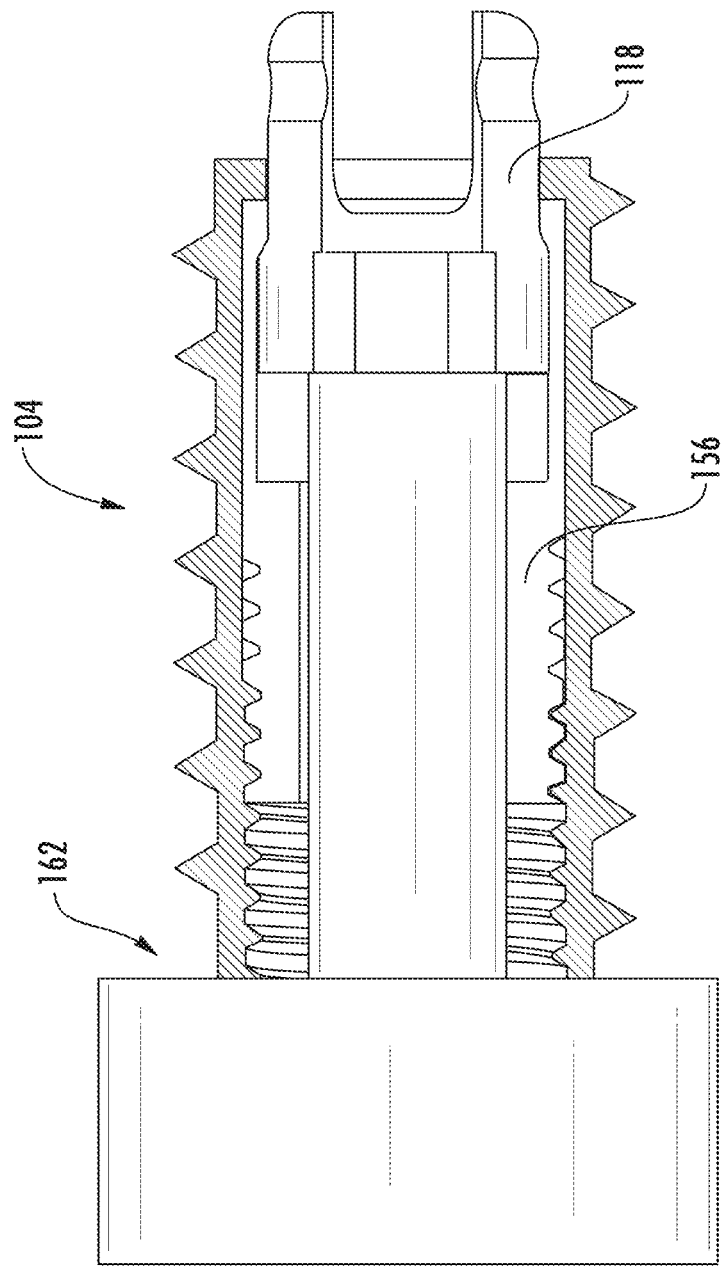
FIG. 26 is a partial cross-sectional view of the second screw including a driving tool.

Once the driving tool 162 is in position, as illustrated in FIG. 26, it can be advanced until the second screw 104 is fully seated at the head 170 and/or desired decompression has been achieved between the vertebral bodies. The driving tool 162 is designed to transfer torque to the first screw 102 (via socket 140) and not the second screw 104. Because the joint 118 is configured to rotate freely within the casing 156, the advancement of driving tool 162 will cause the first screw 102 to rotate (by engaging socket 140) while the joint 118 moves only in the direction towards the distal end 122 (not rotate). After the desired decompression has occurred, the driving tool 162 is removed and the second screw 104 can be locked onto the first screw 102 as described above.

Figure 27:
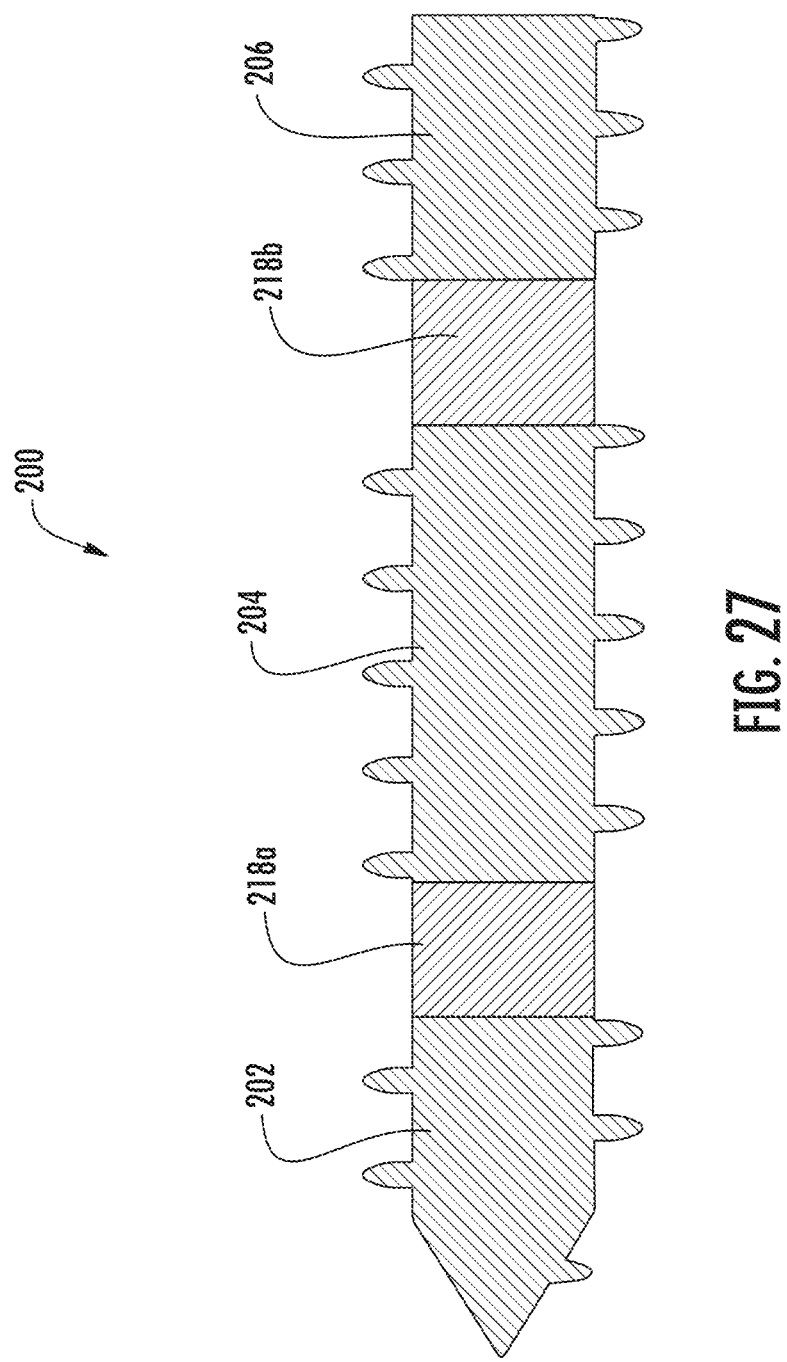
FIG. 27 is cross-sectional view of an example screw assembly.

In another example, the transdiscal screw assembly can include multiple joints coupling separate screw sections. For example, transdiscal screw assembly 200, as illustrated in FIG. 27 includes a first joint 218a coupling a first screw 202 with a second screw 204 and a second joint 218b coupling the second screw 204 with a third screw 206. Though not shown, it is contemplated that the screw assembly 200 can include any number of additional joints and screw sections.

Similar to joint 118, the first and second joints 218a and 218b provide an articulated coupling between the first screw 202, second screw 204 and third screw 206. The joint 218a can be configured to permit the first screw 202 and the second screw 204 to rotate independently of one another. Similarly, joint 218b can be configured to permit the second screw 204 to rotate independently of the third screw 206. As outlined above, independent rotation allows for better purchase (engagement) of the respective screws within the vertebral body/bodies. However, to decrease installation complexity joint 218a and 218b can be designed to not allow independent rotation so the first screw 202, second screw 204 and third screw 206 can follow a predetermined path.

Figure 28:
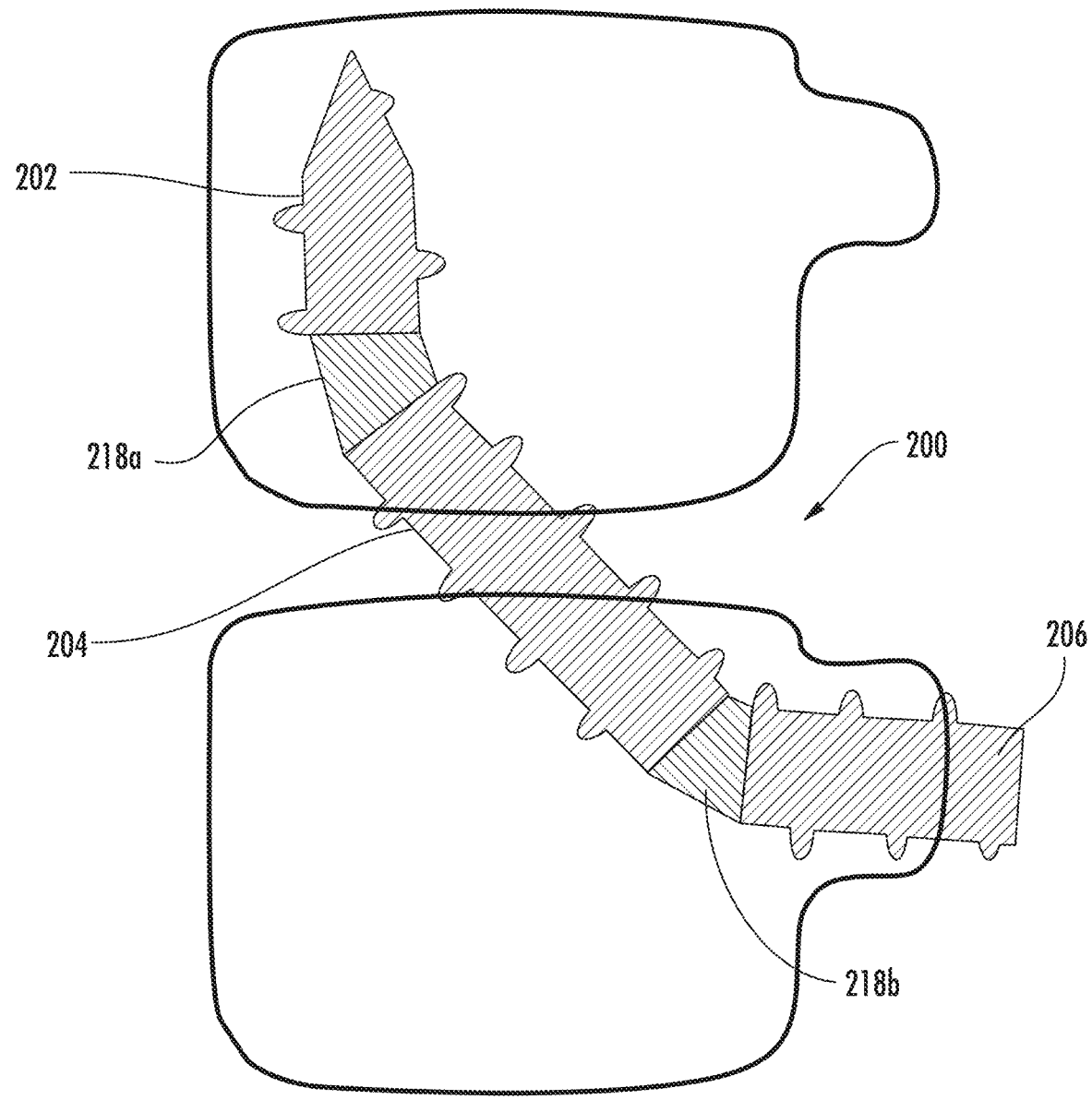
FIG. 28 illustrates the example screw assembly of FIG. 27 advanced along a desired path between two vertebral bodies.

Because joints 218a and 218b allow for bending capability as well as the ability to transfer rotational load along the screw assembly 200, the screw assembly 200 can be advanced along a curved or angled path through multiple vertebral bodies. FIG. 28 provides an illustration of the screw assembly 200 advanced along a curved path between an upper and lower vertebral body. It is contemplated that the joints 218a and 218b will be located within the vertebral bodies when the screw assembly 200 is located in its final placement. For example, as illustrated in FIG. 28, the first screw 202 can be engaged with the upper vertebral body; third screw 206 is engaged with the lower vertebral body; second screw 204 can be located such that it engages both the upper and lower vertebral bodies; and the first joint 218a and second joint 218b are located within the upper and lower vertebral bodies, respectively. As such, no flexible/rotational component of the screw assembly 200 (e.g., first joint 218a and second joint 218b) is located in the disc space where the physiological motion is present. Also, the second screw 204 can act to stabilize the mobile disc joint.

As illustrated in FIG. 28, in one configuration the first joint 218a and the second joint 218b can be located within the upper and lower vertebral bodies, respectively. However, the location of the joints within the either of the upper or lower vertebral bodies can vary based on the length of the first, second and third screws. For example (not shown), a longer or shorter first screw 202, in relation to the second and third screws 204 and 206, may result in the first joint 218a being located within the same vertebral body as the second joint 218b.

Figure 29:
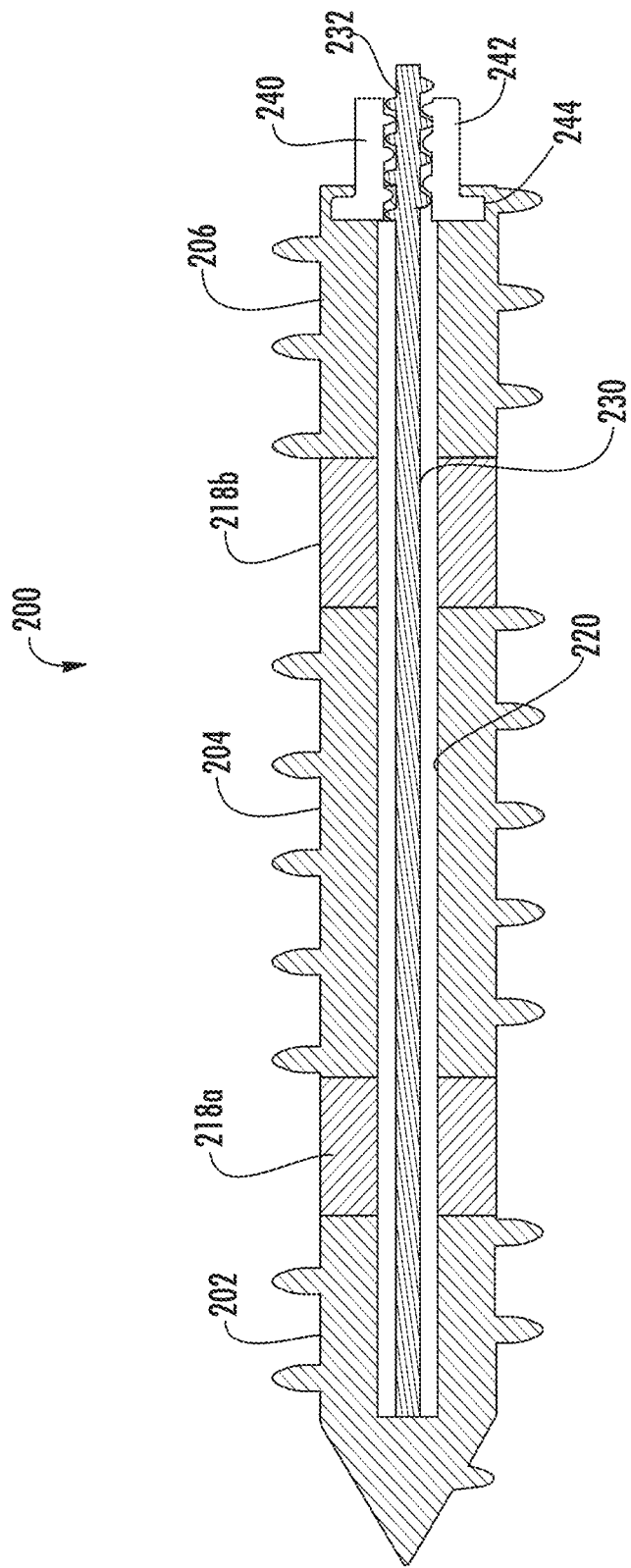
FIG. 29 is cross-sectional view of an example screw assembly.

As illustrated in FIG. 29, the screw assembly 200 can be cannulated and/or include a central passage 220 sized and configured to accommodate a control wire 230. The control wire 230) can be used to facilitate fixing the position and/or configuration of the screw assembly 200 with the vertebral bodies. For example the control wire 230 can be coupled between the proximal and distal end of the screw assembly 200. As illustrated in FIG. 29, the control wire 230 is coupled to the distal end of the screw assembly 200 at the first screw 202. Likewise the control wire 230 can be coupled to the proximal end of the screw assembly at the third screw 206. In an example assembly 200, the proximal end of the screw assembly 200 can include a locking nut 240 coupled to the third screw 206. The control wire 230 can be coupled between the first screw 202 and the locking nut 240.

In an example assembly 200, the locking nut 240 can be coupled to the proximal end of the screw assembly 200 (i.e., third screw 206) via an interlocking mechanism 244. The interlocking mechanism 244 can restrain the locking nut 240 within the screw assembly 200 (i.e., third screw 206) while permitting the locking nut 240 to rotate independent of the screw assembly 200. For example, the interlocking mechanism 244 can include an edge or surface of the locking nut 240 sized and configured to rotatably engage a corresponding surface/opening of the third screw 206.

The locking nut 240 can include an internal threaded portion 242 for coupling with a corresponding threaded portion 232 included on the control wire 230. As the locking nut 240) is rotated with respect to the screw assembly 200, the threaded portion 232 of the control wire 230 is tightened with respect to the threaded portion 242 of the locking nut 240. As a result, the tension on the control wire 230 increases and the configuration/shape of the various screw assembly 200 components are fixed/locked into place with respect to each other.

Figure 30:
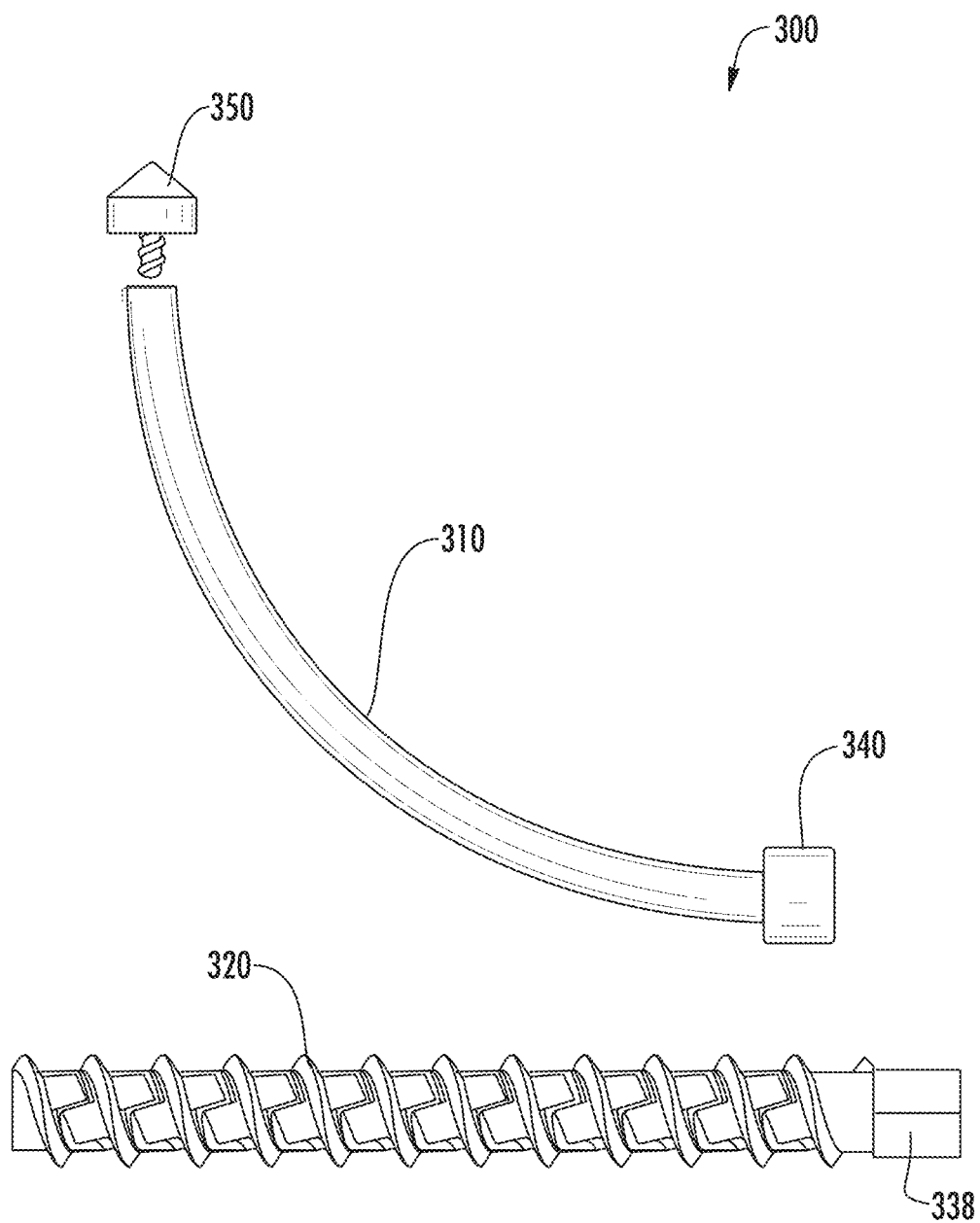
FIG. 30 is a plan view of an example screw assembly.

Another example screw assembly can include a transdiscal screw having a flexible screw shank. For example, a flexible transdiscal screw assembly 300, as illustrated in FIG. 30, can include a threaded flexible sleeve 320 and a core 310. When assembled, the core 310 extends within a central passage 328 of the flexible sleeve 320 thereby defining the final shape of the flexible sleeve 320 and providing stability and strength to the screw assembly 300. The core 310 can define a curved trajectory thereby increasing the pull-out resistance of the screw assembly 300. As will be described in more detail below, the screw assembly 300 can also include a locking mechanism 340 coupled at the proximal end and a cap 350) at the distal end. The locking mechanism 340 can be used to fix the core 310 within the flexible sleeve 320. The cap 350 can be used the prevent extension of the flexible sleeve 320 beyond the distal end of the core 310.

Figure 32:
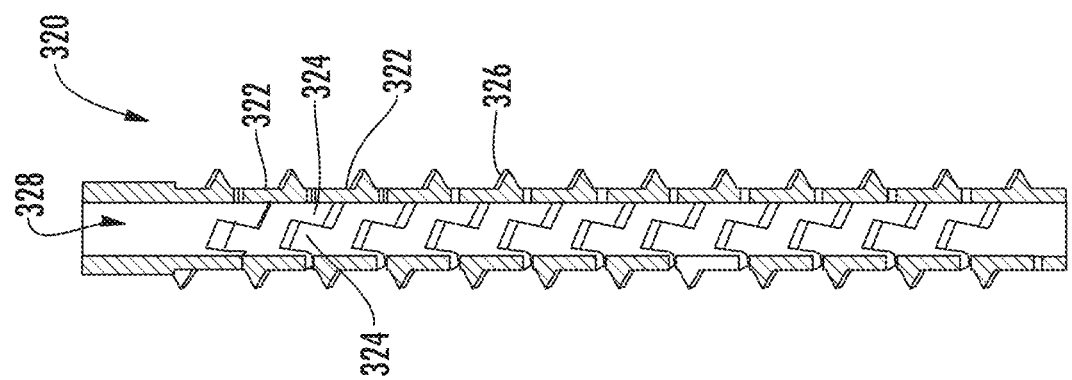
FIG. 32 is a cross-sectional view of the example flexible sleeve of FIG. 31.
Figure 31:
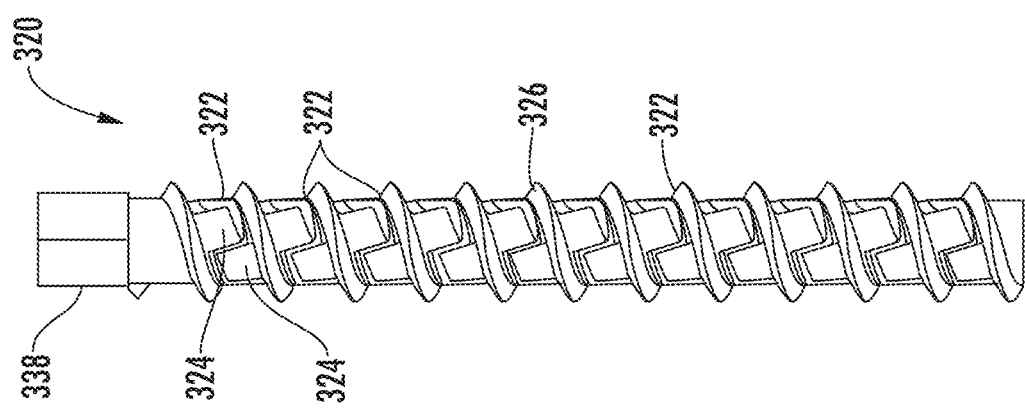
FIG. 31 is a plan view of an example flexible sleeve.
Figure 34:
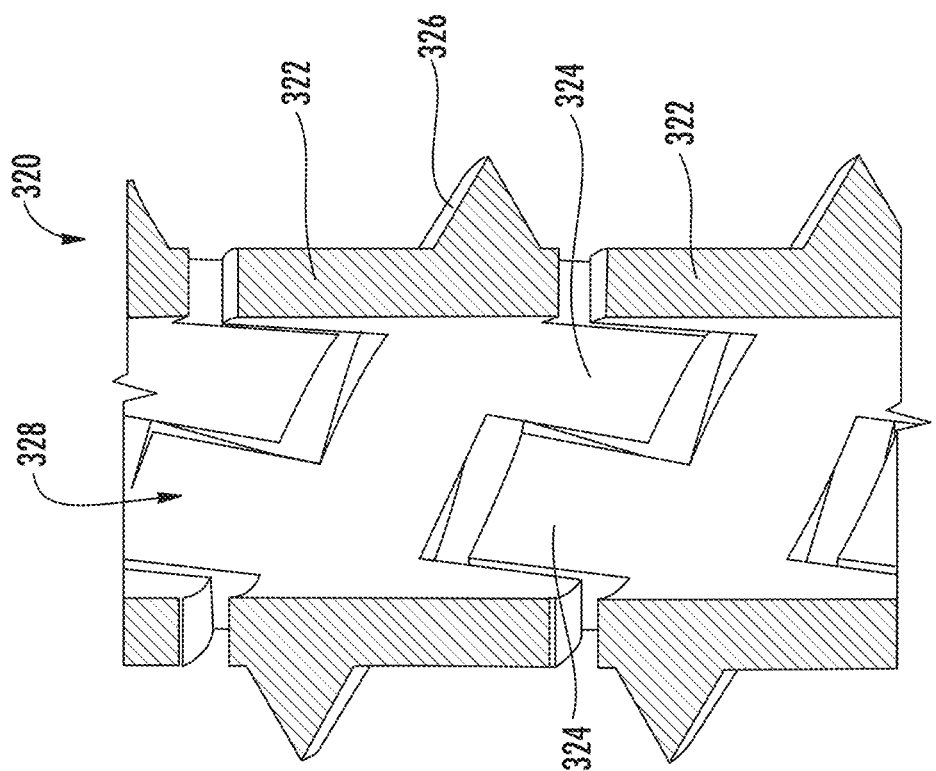
FIG. 34 is a partial cross-sectional view of the example flexible sleeve of FIG. 31.
Figure 33:
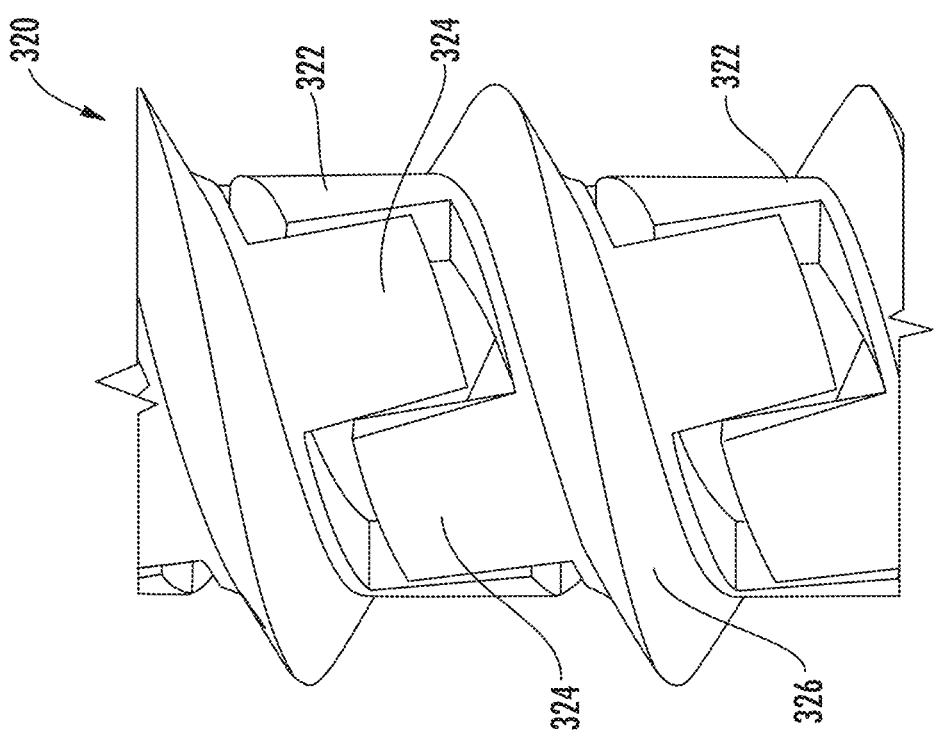
FIG. 33 is a partial plan view of the example flexible sleeve of FIG. 31.
Figure 35:
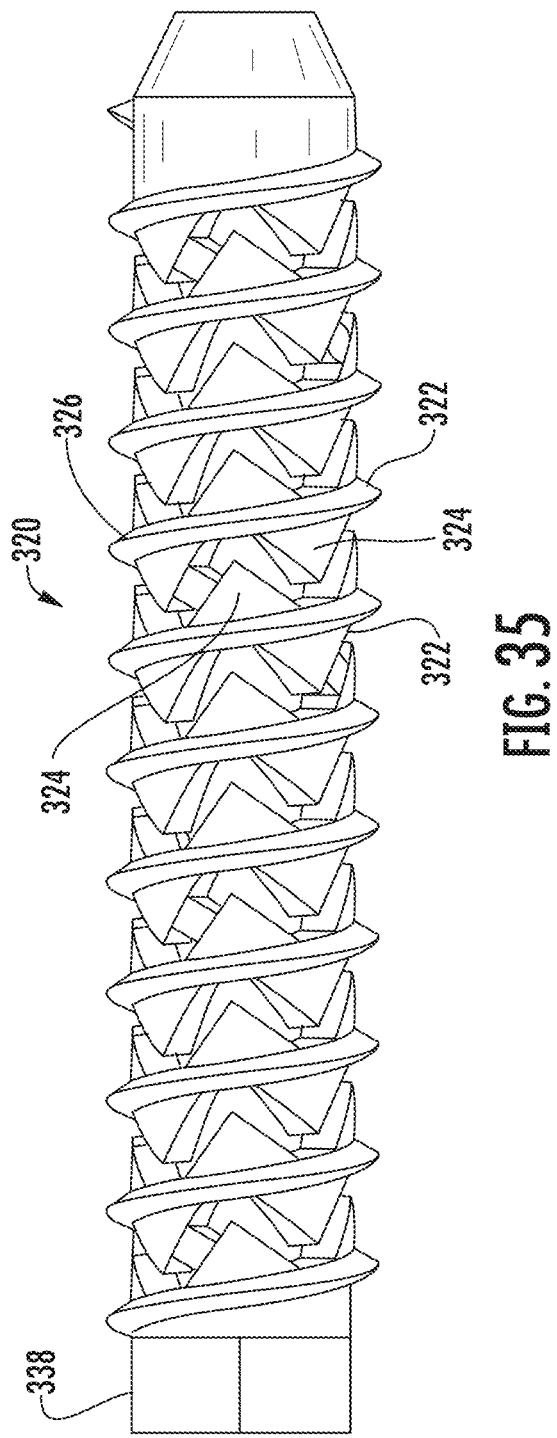
FIG. 35 is a plan view of an example flexible sleeve.
Figure 36:
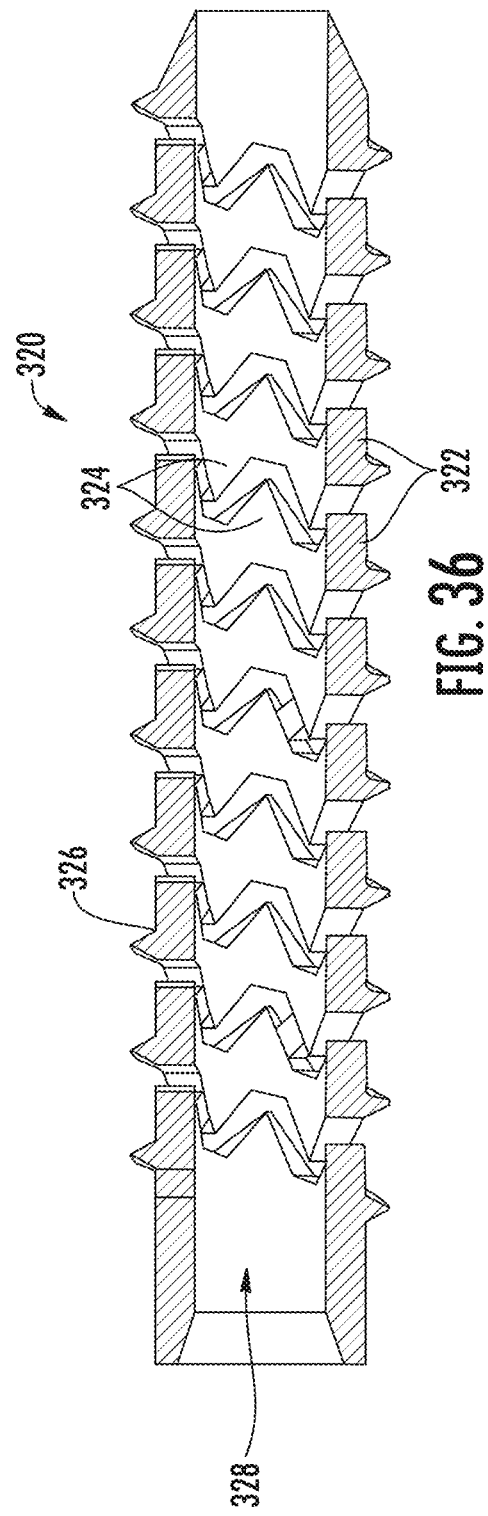
FIG. 36 is a cross-sectional view of the example flexible sleeve of FIG. 35.
Figure 37:
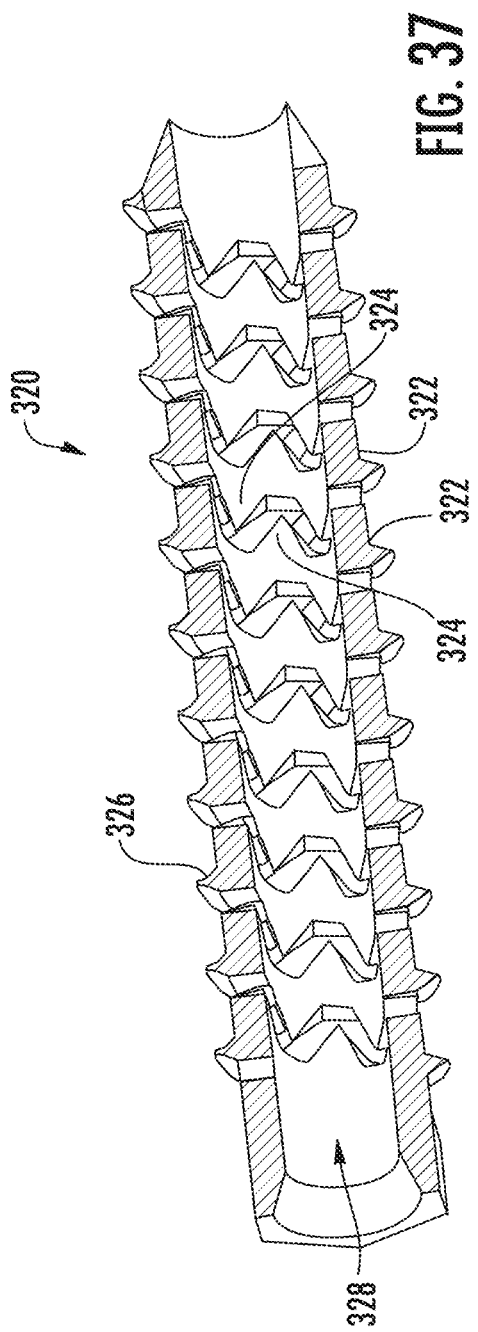
FIG. 37 is a cross-sectional view of the example flexible sleeve of FIG. 35.
Figure 38:
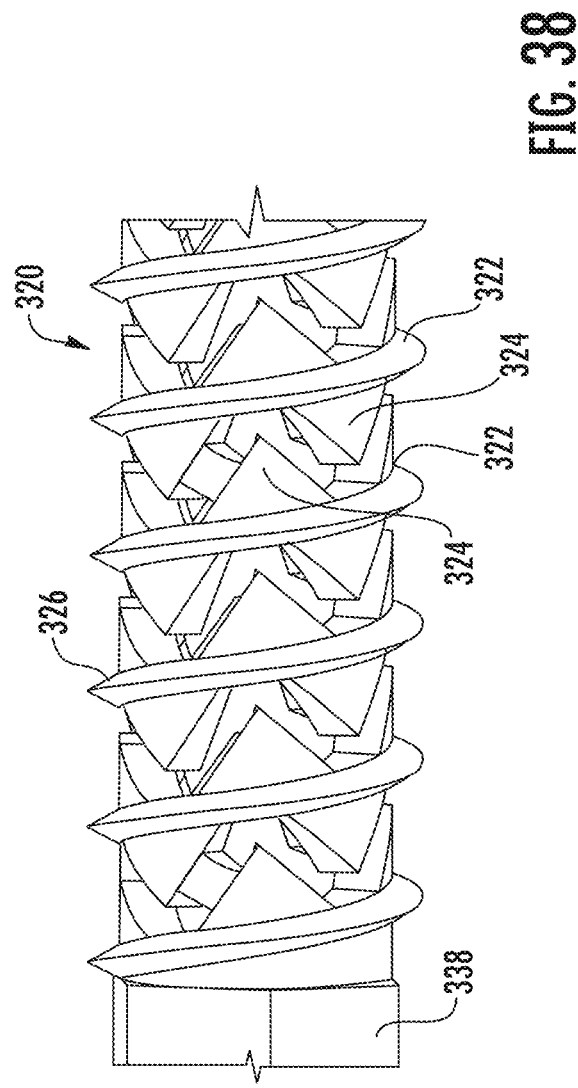
FIG. 38 is a partial plan view of the example flexible sleeve of FIG. 35.

FIG. 31 illustrates an example flexible sleeve 320. FIG. 32 provides a cross-section view of the example sleeve 320 illustrated in FIG. 31. The flexible sleeve 320 can define a hollow cylindrical body including a plurality of sleeve elements 322. The sleeve element 322 can include teeth 324 for engaging/interlocking the corresponding teeth 324 of an adjacent element 322. Engagement between the interlocking teeth 324 provides for flexibility of the sleeve 320) in a direction orthogonal to the longitudinal axis. In an example sleeve 320, the interlocking teeth 324 can follow a helical path around the perimeter of the sleeve 320 allowing for degrees of freedom in all directions. Engagement between the interlocking teeth 324 can further facilitate transmitting torque and axial translation resulting from rotation of the sleeve 320. As a result, the flexible sleeve 320 can follow a curved and/or straight trajectory.

Figure 39:
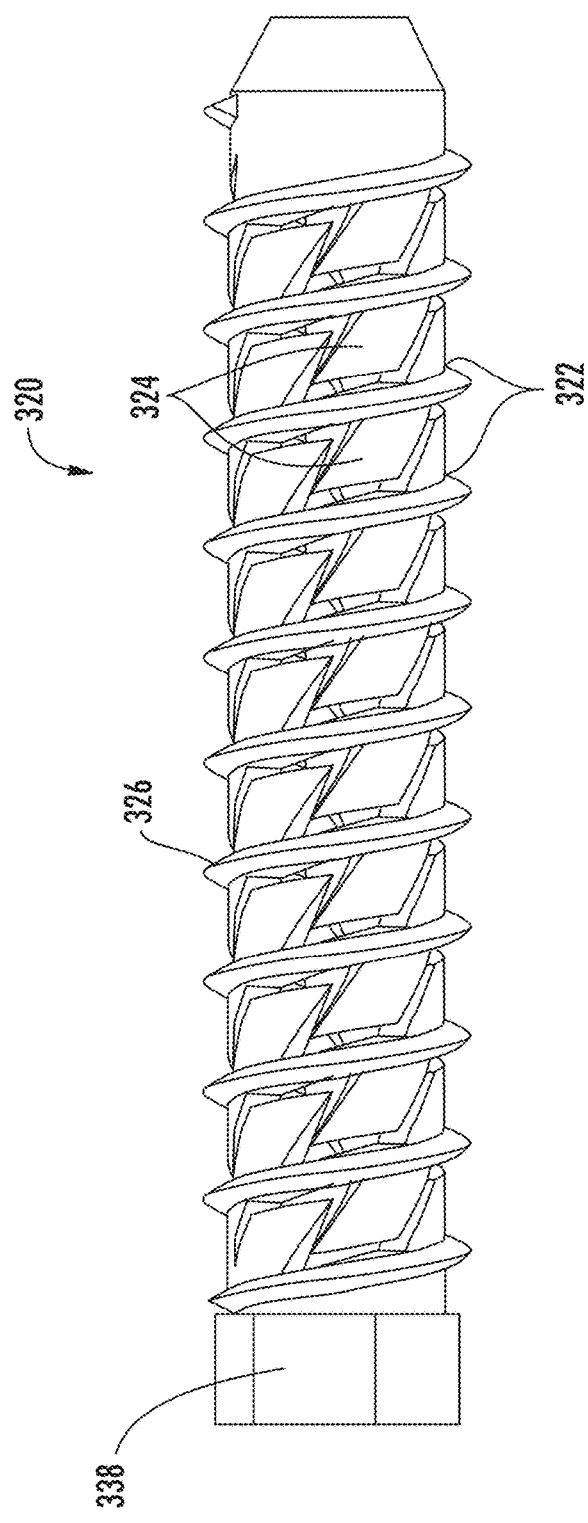
FIG. 39 is a plan view of an example flexible sleeve.
Figure 40:
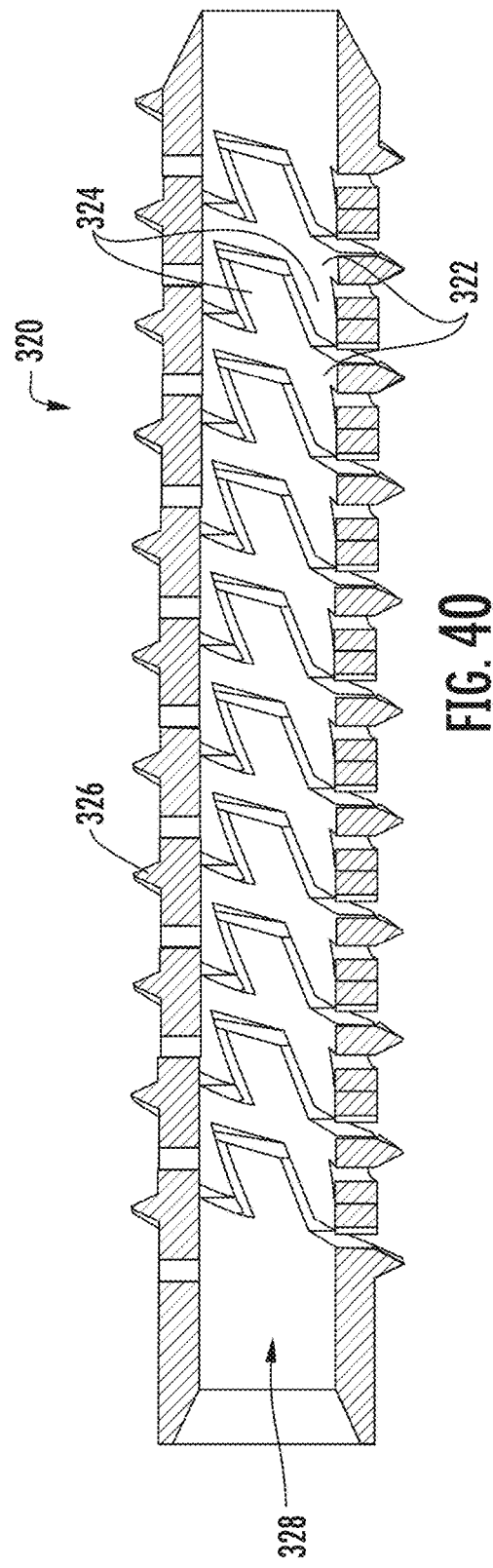
FIG. 40 is a cross-sectional view of the example flexible sleeve of FIG. 39.
Figure 43:
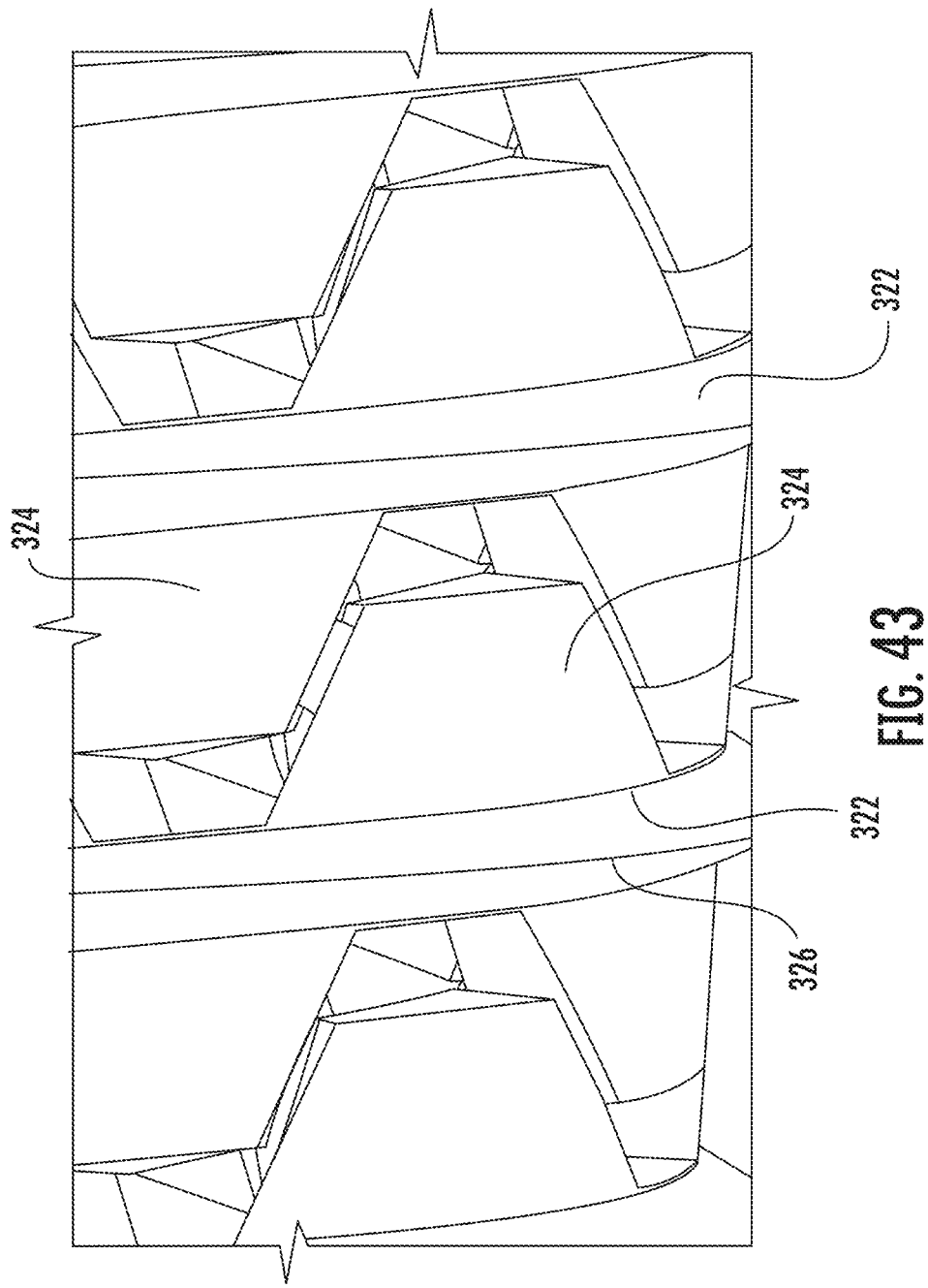
FIG. 43 is a partial plan view of the example flexible sleeve of FIG. 41.
Figure 44:
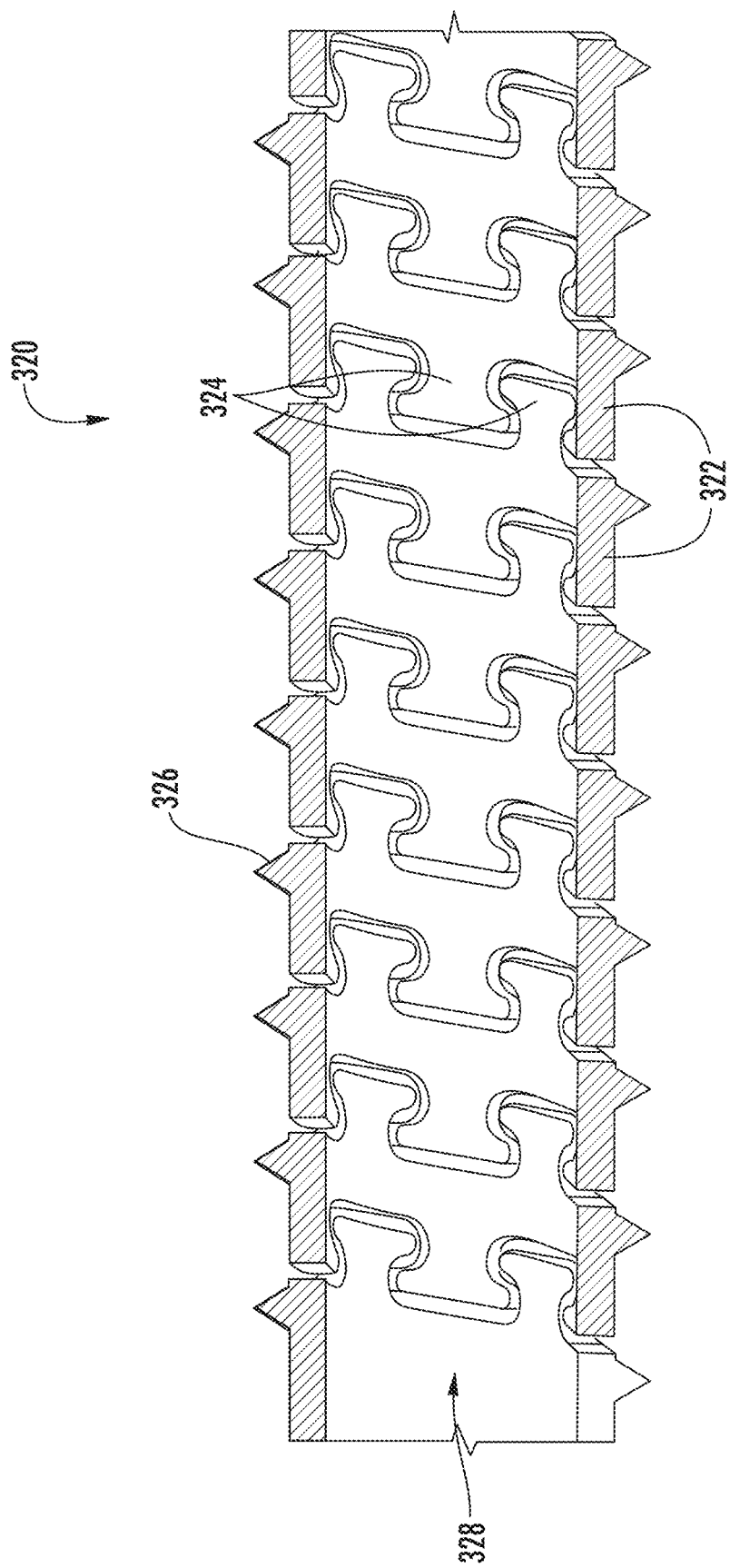
FIG. 44 is a partial cross-sectional view of an example flexible sleeve.
Figure 45:
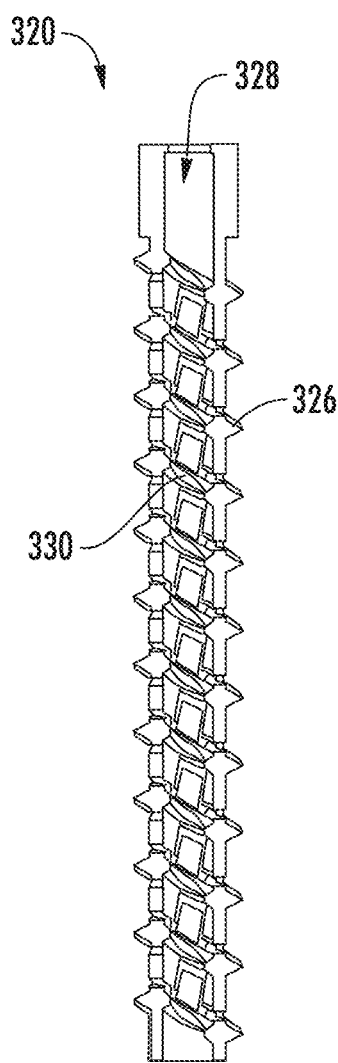
FIG. 45 is a cross-sectional view of an example flexible sleeve.
Figure 46:
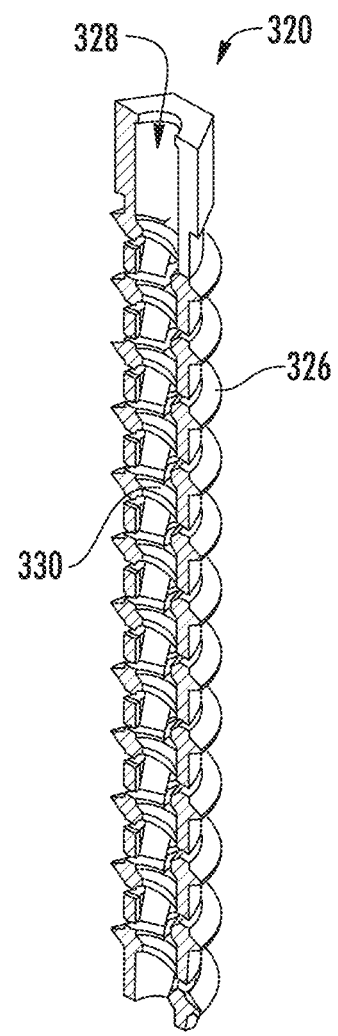
FIG. 46 is a perspective cross-sectional view of the example flexible screw of FIG. 45.
Figure 48:
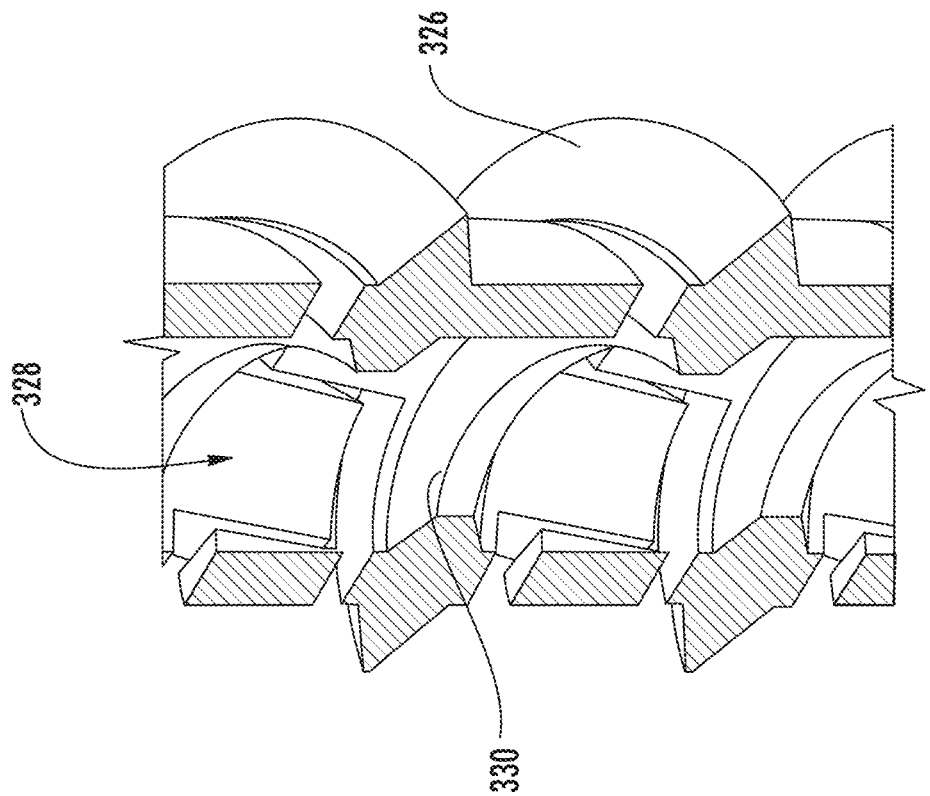
FIG. 48 is a partial perspective cross-sectional view of the example flexible screw of FIG. 45.
Figure 47:
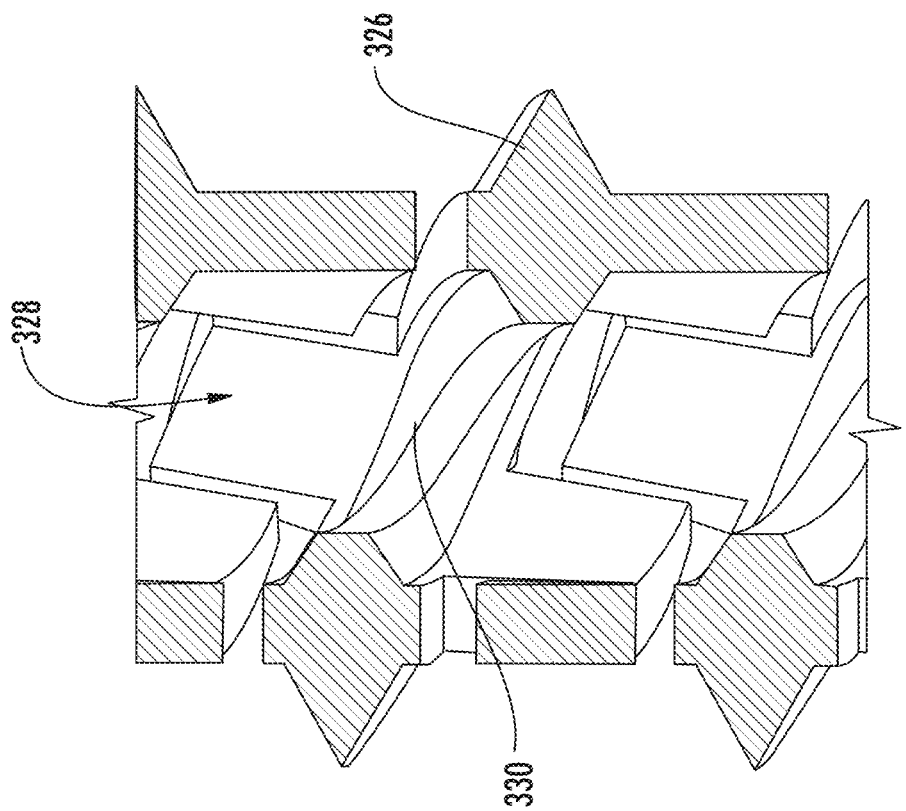
FIG. 47 is a partial plan cross-sectional view of the example flexible screw of FIG. 45.

In one example, illustrated in FIGS. 31-34, the interlocking teeth 324 can define a square-shaped pattern. The square pattern can be used to provide a flexible sleeve 320 that has an increased rotational stability and strength. The square pattern can be used to provide a flexible sleeve 320 and can provide increased bending when compared to locked/self-locking patterns (e.g., dumb-bell/dog bone, dovetail). In another example, illustrated in FIGS. 35-38, the square pattern can be rotated at an angle with respect to the edge of the sleeve element 322 to provide for a triangle/diamond-shaped pattern. The interlocking teeth 324 can also define a rhombus or parallelogram-shaped pattern as provided in FIGS. 39 and 40. The negative angle of the interlocking teeth 324 can allow for larger allowable torque because the uncoiling effect typically caused by advancement is replaced by the tightening effect during advancement. In a further example, illustrated in FIGS. 41-43, the interlocking teeth 324 can define a hexagon-shaped pattern. In yet another example, the interlocking teeth 324 can define a dumb-bell/ dog bone pattern as provided in FIG. 44. The dumb-bell/dog bone pattern can be used to provide a flexible sleeve 320 that allows torque transmission and limits axial translation of the flexible sleeve 320. Moreover, the dumb-bell/dog bone pattern can be used to provide a flexible sleeve 320 that limits excess bending/the maximum curvature of the flexible sleeve 320. It is contemplated that any other style/shape of interlocking tooth pattern known in the art may be used with respect to the interlocking teeth 324. Different style/shapes of interlocking tooth patterns can be utilized to reduce the "uncoiling" and "tightening" effects caused by the applied torque to the interlocking teeth 324 (applied advancement torque can induce an "uncoiling" effect due to the positive angle of the gears and winding pattern of the screw, while retraction torque can cause "tightening" effect).

As illustrated in FIGS. 30-48, the flexible sleeve 320 can also include an external thread 326 for engaging a vertebral body. As provided above, the sleeve 320 can define a hollow cylindrical body including a central passage 328 sized and configured to receive the core 310. In an example assembly 300, the central passage 328 of the flexible sleeve 320 can include internal threads 330, illustrated in the example flexible sleeve 320 depicted in FIGS. 45-48. The internal threads 330 can be sized and configured to engage corresponding threads (external threads 314) of the core 310, as will be described in more detail below. Inner threads 330) can also be utilized to reduce the "uncoiling" and "tightening" effects that can be caused by applied torque to the interlocking teeth 324.

Figure 49:
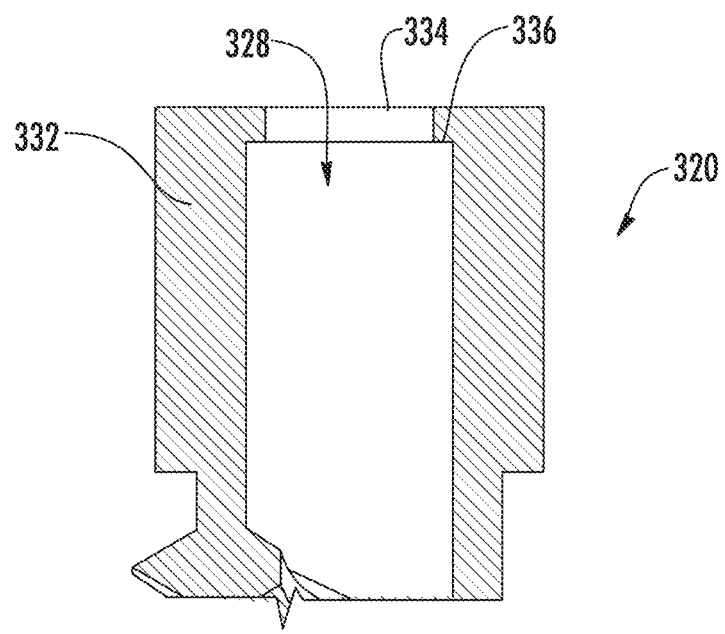
FIG. 49 is a partial cross-sectional view of the distal end of an example screw.
Figure 50:
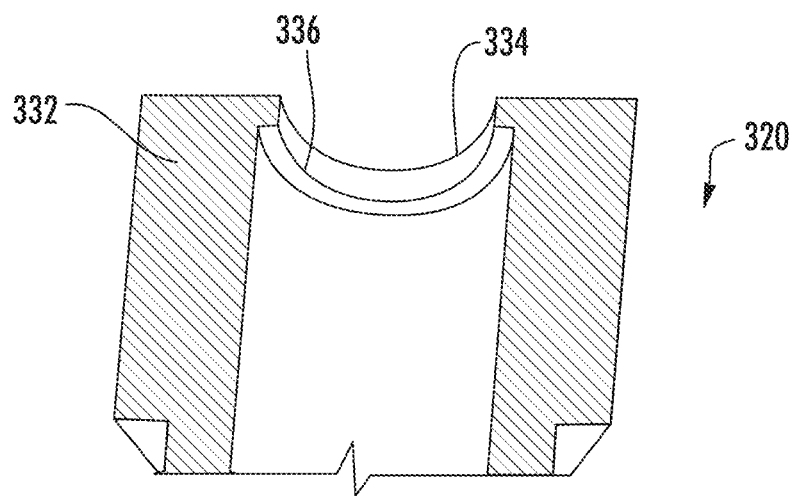
FIG. 50 is a perspective cross-sectional view of the distal end of the example screw of FIG. 49.

As illustrated in FIGS. 49 and 50, the distal end of the flexible sleeve 320 can include a head 332. The head 332 can include an opening 334 in communication with the central passage 328 of the flexible sleeve 320. The opening 334 can be sized and configured to receive a portion of the cap 350. The head 332 can also include an engagement surface 326. The engagement surface 326 can include an edge or lip proximate the opening 334 that impacts the core 310 when the flexible sleeve 320 is provided over the core 310. The engagement surface 326 prevents the flexible sleeve 320 from extending beyond the distal end core 310.

The proximal end of the flexible sleeve 320 can include a drive surface 338 for receiving a corresponding drive tool for delivering rotational torque to the flexible sleeve 320. As illustrated in FIGS. 30, 31, 35, 38 and 39, the drive surface 338 can include a flattened surface provided on the flexible sleeve 320 for engaging a corresponding female adaptor/ drive tool.

As described above, the flexible screw assembly 300 can include a core 310 that extends within the central passage 328 of the flexible sleeve 320. The core 310 can be constructed from a rigid/stiff material such providing the flexible sleeve 320 over the core 310 provides stability and strength to the screw assembly 300. The core 310 can also define a straight or curved trajectory that ultimately provides the final shape of the flexible sleeve 320 when the screw assembly 300 is inserted and positioned at its final location.

Figure 52:
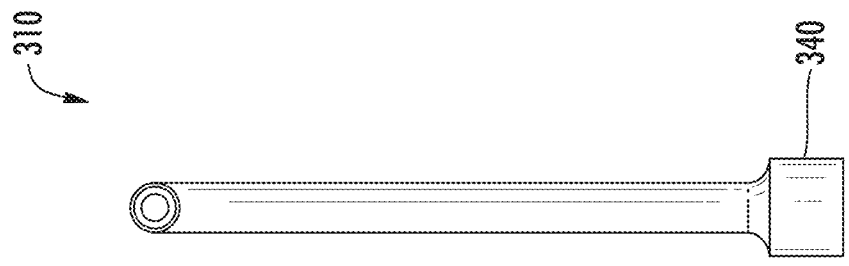
FIG. 52 is a front view of the example curved core of FIG. 51.
Figure 51:
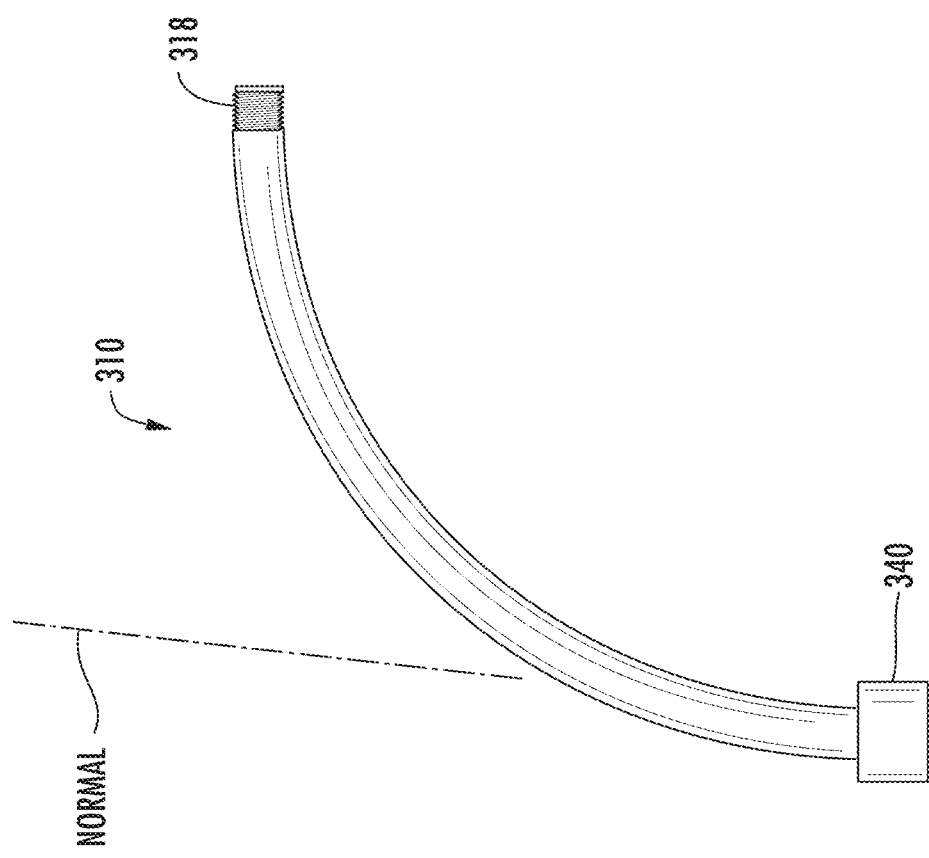
FIG. 51 is a side view of an example curved core.
Figure 53:
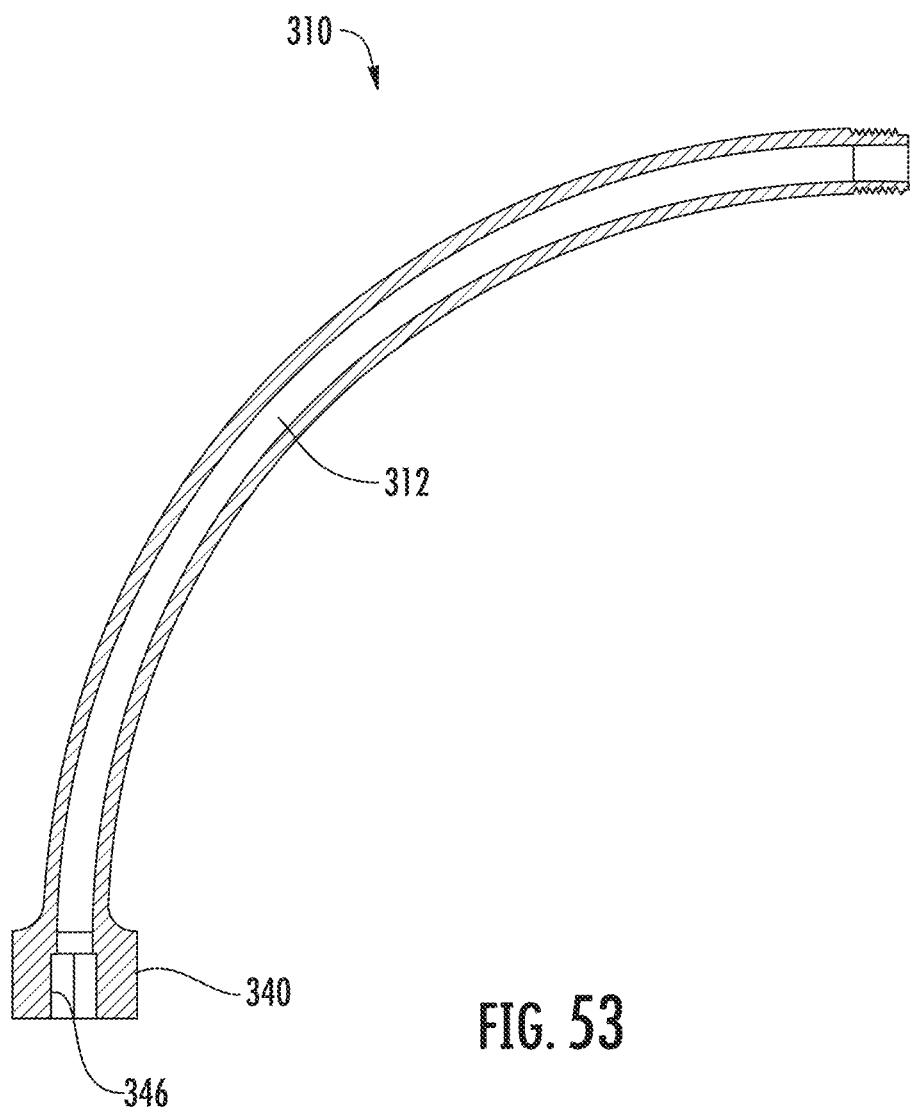
FIG. 53 is a cross-sectional view of the example curved core of FIG. 51.

An example curved core 310 is illustrated in FIGS. 51-53. The example core 310 can deflect in a direction away from the normal axis of the core 310. It is also contemplated that the curved core 310 can deflect in more than one direction away from the normal axis of the core 310. For example, the core 310 can be defined with respect to a traditional geometric axis system (X, Y, Z) where the Z-axis represents the axis extending vertically from the plane defined by the X and Y axis. The Z-axis represents the normal axis of the core 310. It is contemplated that the core 310 will extend vertically along the Z-axis and can be deflected in any direction relative to the X and/or Y-axis along its trajectory. It is also contemplated that the core 310 can define a sector of an arc/curve with or without a constant radius.

As illustrated in FIG. 53, providing a cross-sectional view of an example core 310, the core 310 can define a hollow cylindrical body having a central passage 312. In another example (not shown), the core 310 can be a solid cylindrical body. While the exterior surface of the core 310 is described as cylindrical, it is contemplated that the core 310 can define any geometry sized and configured to be accommodated by the central passage 328 of the flexible sleeve 320. For example, the core 310 can define an elongated elliptical, square, rectangular, hexagon, or any other regular or irregular shape. The core 310 can also have a varying transverse area along the longitudinal axis of the core. For example, the core 310 can define a conical transverse area along the longitudinal axis.

As provided in FIGS. 51-53, the outer surface of the core 310 can have an even or smooth surface. In another example, illustrated in FIGS. 54-56, the core 310 can include external threads/grooves 314 for rotatably engaging corresponding internal threads 330 provided in the central passage 328 of the flexible sleeve 320.

Figure 57:
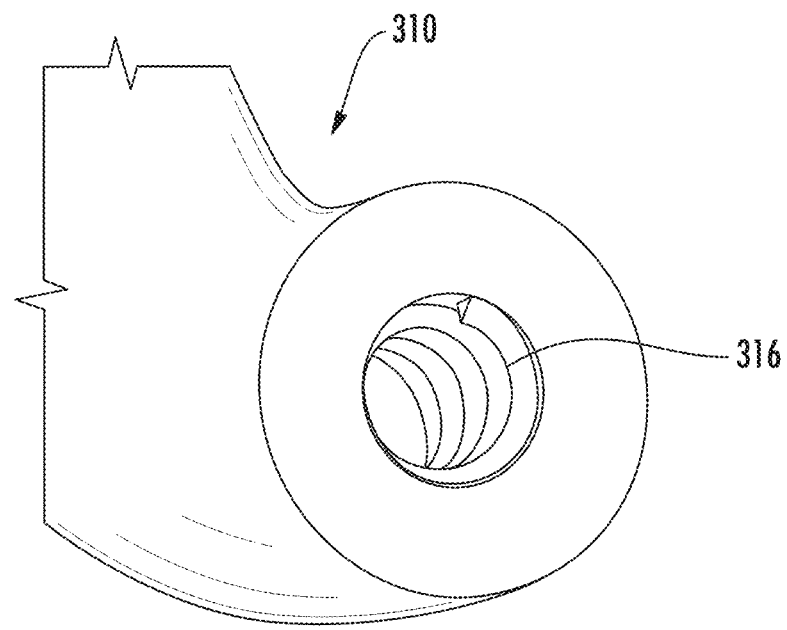
FIG. 57 is a partial plan view of the proximal end of an example core.
Figure 59:
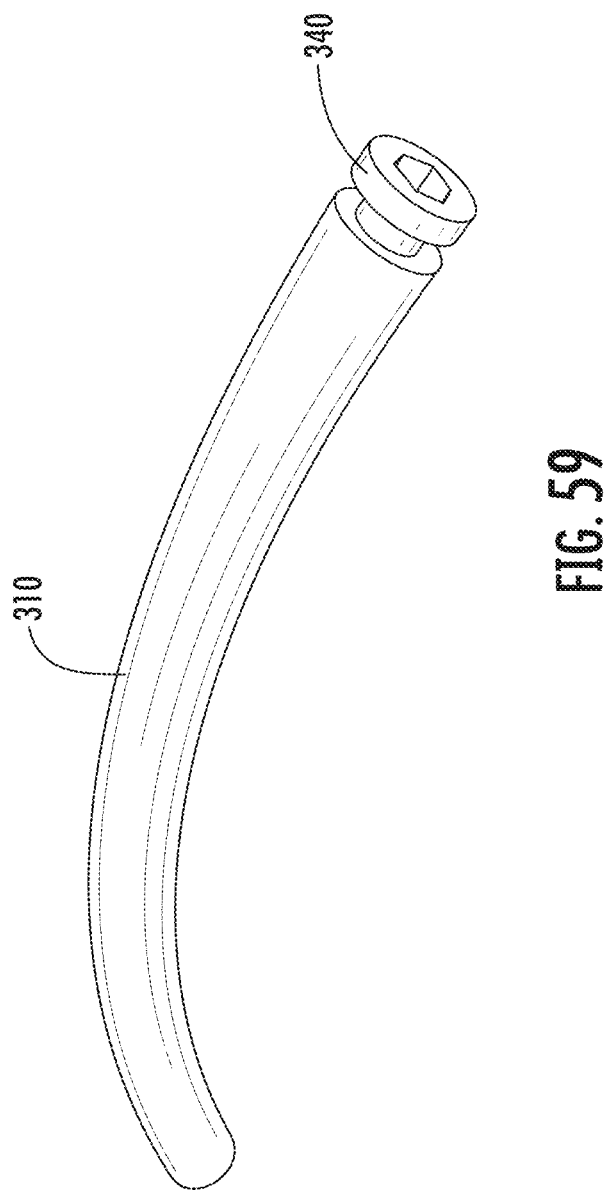
FIG. 59 is a perspective view of an example core and locking mechanism.

The screw assembly 300 can also include a locking mechanism 340 coupled at the proximal end of the core 310. The locking mechanism 340 can be used to fix the position of the core 310 with respect to the flexible sleeve 320. The locking mechanism 340 prevents the flexible sleeve 320 from advancing within the vertebral body and can hold the flexible sleeve 320 in place while allowing rotation of the flexible sleeve 320 with respect to the core 310. As illustrated in FIGS. 51-53, the locking mechanism 340 can be integral to the core 310 defining a diameter greater than the outer diameter of the core 310. In another example, the locking mechanism 340 is removably and/or fixedly coupled to the core 310. For example, the proximal end of the core 310 can include an engagement feature 316 for matingly engaging a corresponding engagement feature 342 of the locking mechanism 340. As illustrated in FIG. 57, the core engagement feature 316 can include internal threads for engaging a corresponding threaded projection 316 provided on the locking mechanism 340. FIG. 59 illustrates a core 310 coupled to an example locking mechanism 340.

Figure 55:
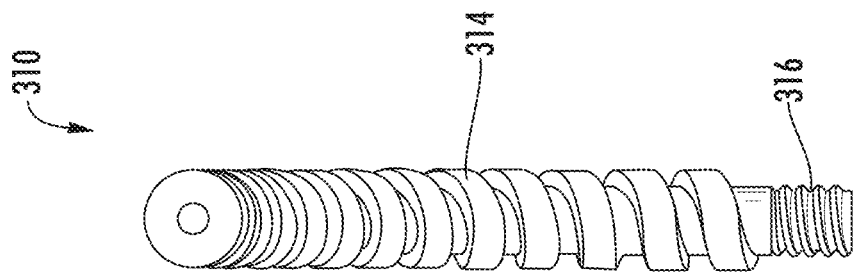
FIG. 55 is a front view of the example curved core of FIG. 54.
Figure 54:
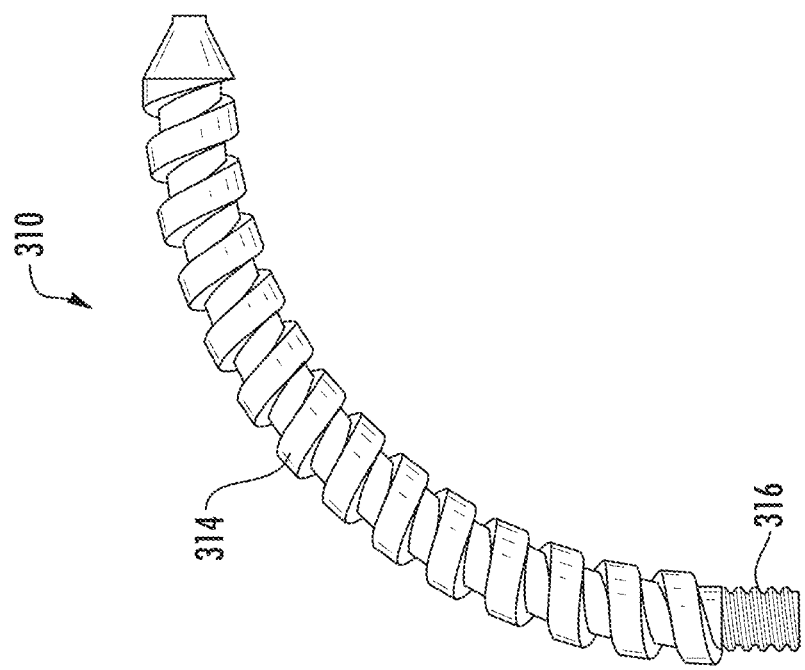
FIG. 54 is a side view of an example curved core.
Figure 56:
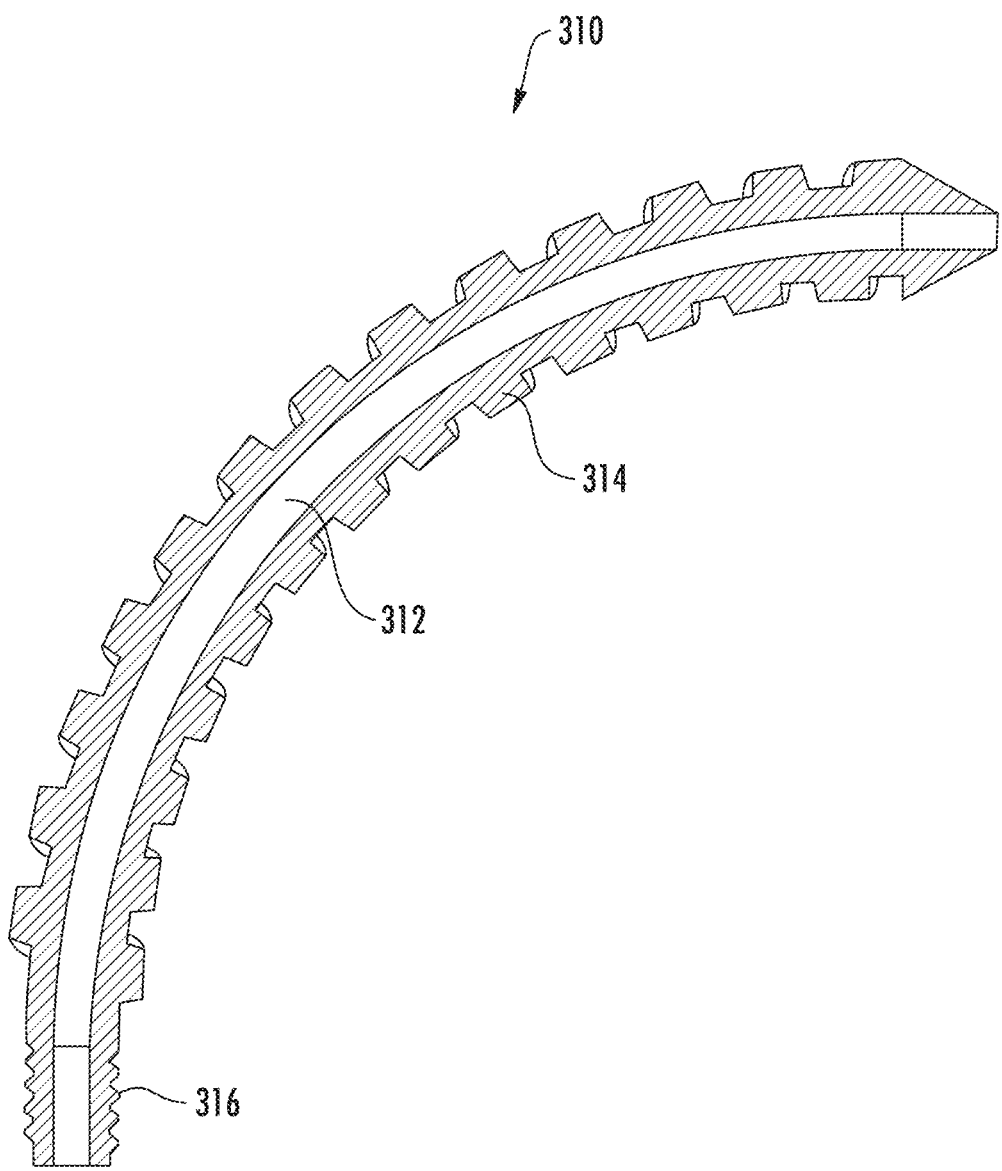
FIG. 56 is a cross-sectional view of the example curved core of FIG. 54.
Figure 60:
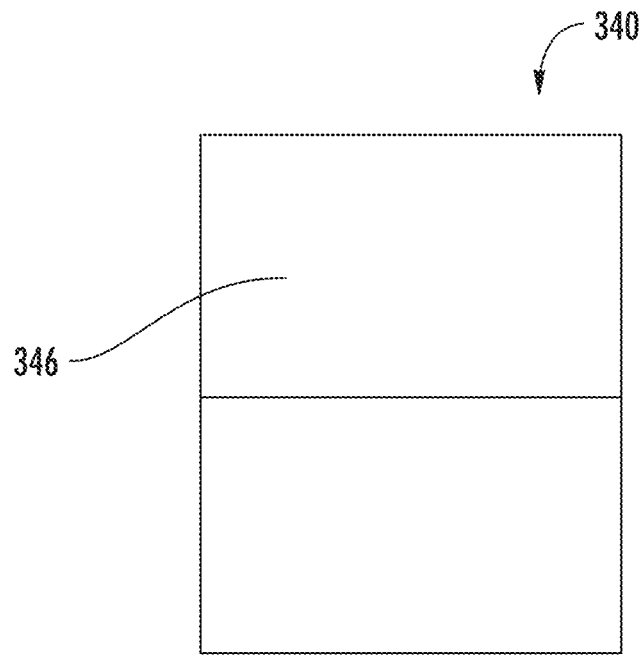
FIG. 60 is a side view of an example locking mechanism.
Figure 61:
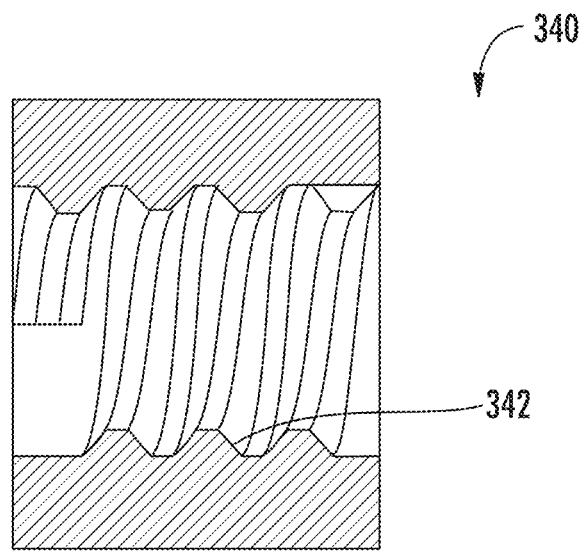
FIG. 61 is a side cross-sectional view of an example locking mechanism.

In another example, illustrated in FIGS. 54-56, the engagement feature 316 of the core 310 can include external threads for engaging a corresponding threaded feature of the locking mechanism 340. An example corresponding locking mechanism 340 can include a nut-type element as provided in FIGS. 60 and 61. As illustrated in FIG. 61, providing a cross-sectional view of the example nut-type locking mechanism 340, the locking mechanism 340) can include internal threads 342 for engaging the corresponding external threads 316 of the core 310.

Figure 58:
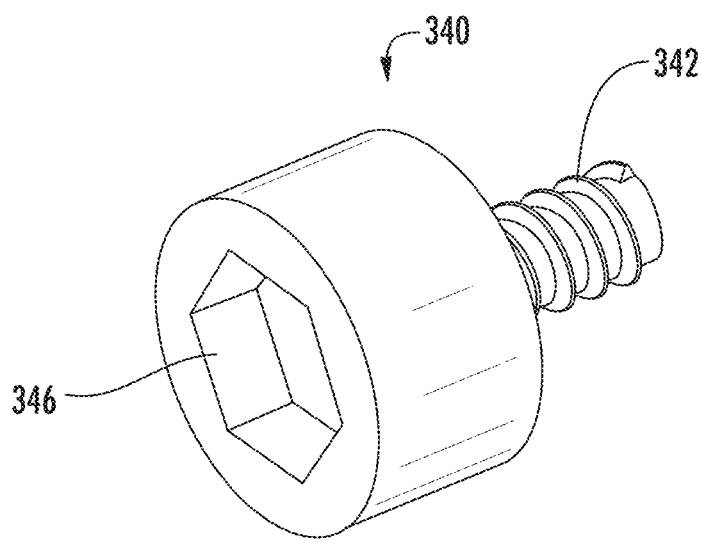
FIG. 58 is a perspective view of an example locking mechanism.

The locking mechanism 340 can include a drive surface 342 for receiving a corresponding end of a drive tool, such as a screw driver, for transmitting rotational torque of the drive tool to the locking mechanism 340. The drive surface 342 may have any form including, but not limited to, an external hexagon, a star drive pattern, a Phillips head pattern, a slot for a screw driver, a threading for a correspondingly threaded post, etc. As illustrated in FIG. 58, an example drive surface 342 can include a hexagon pattern. As illustrated in FIG. 60, the drive surface 342 can include a flat surface provided on the exterior of the locking mechanism 340 for engaging a corresponding female adaptor/drive tool.

Figure 62:
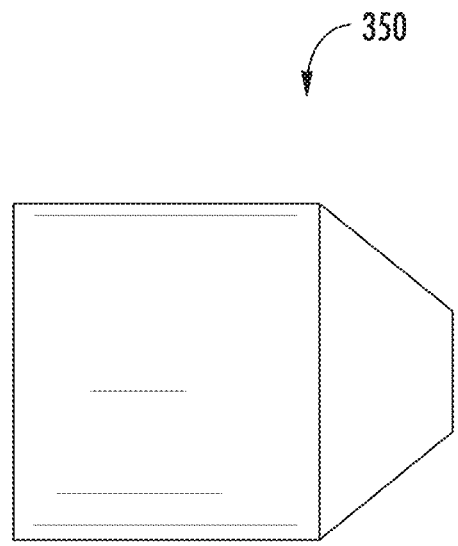
FIG. 62 is a side view of an example cap.
Figure 63:
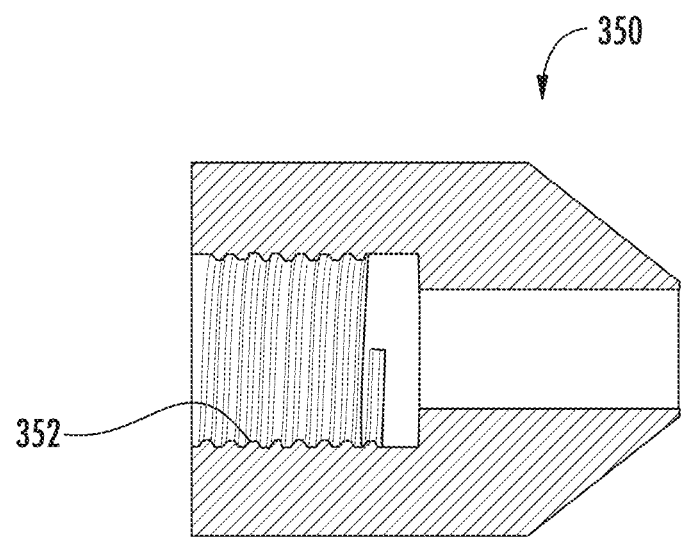
FIG. 63 is a side cross-sectional view of an example cap.
Figure 64:
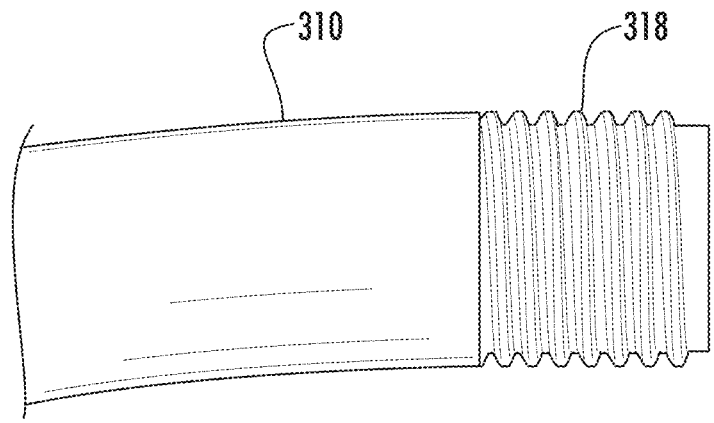
FIG. 64 is a partial side view of the distal end of an example core.
Figure 65:
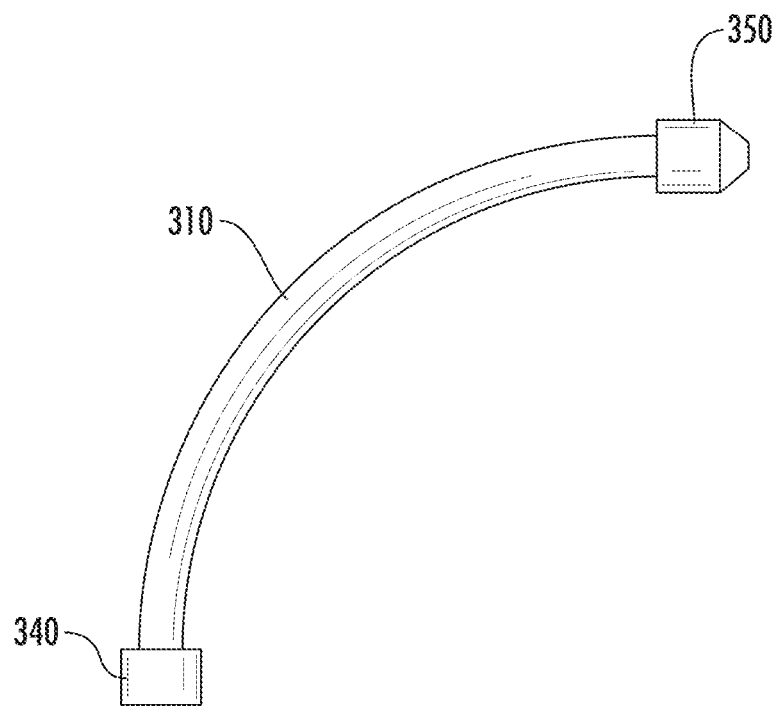
FIG. 65 is a side view of an example core and cap.
Figure 69:
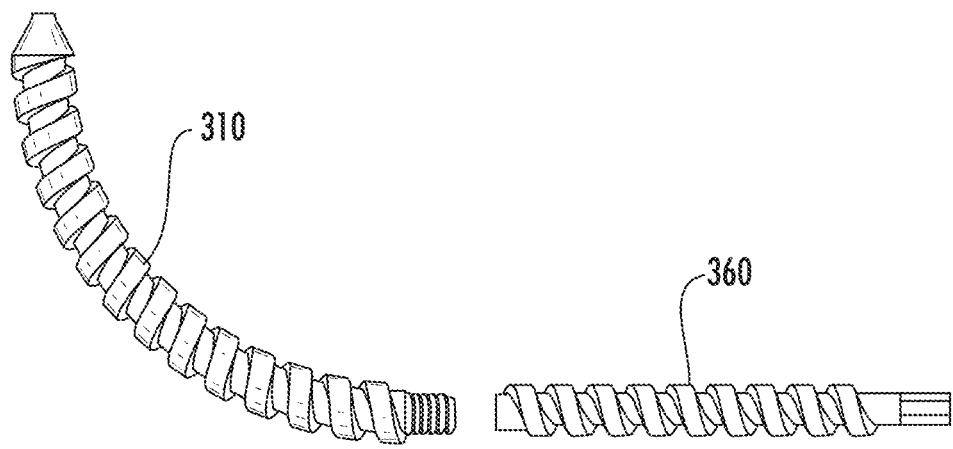
FIG. 69 is a side view of an example core and core extension.
Figure 70:
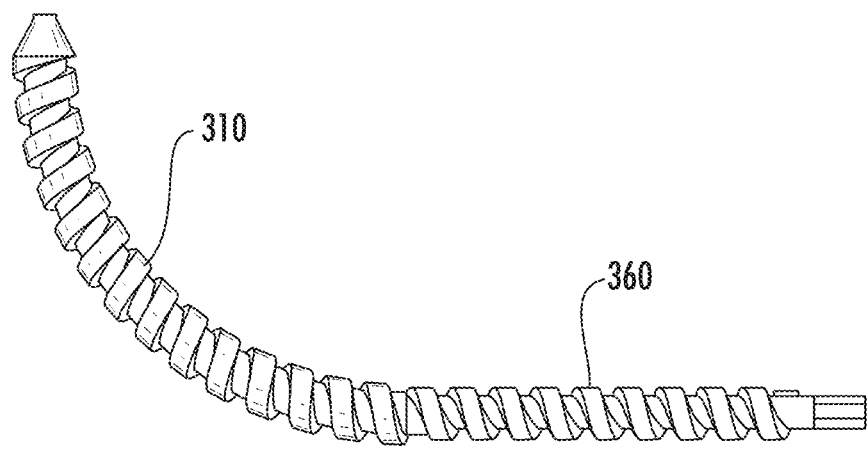
FIG. 70 is a side view of an example core and core extension.

The screw assembly 300 can also include a cap 350 coupled to the distal end of the core 310. The cap 350 can be used the prevent extension of flexible sleeve 320 beyond the distal end of the core 310. For example, the cap 350 can provide a surface having a diameter greater than the outer diameter of the core 310 such that when the flexible sleeve 320 is inserted over the core 310, an impact surface of the cap 350 prevent the flexible sleeve 320 from extending beyond the end of the core 310. In one example, the cap 350 can be formed integral to the core 310 and or fixed permanently thereto. In another example, the cap 350 is removably coupled to the core 310. An example cap 350 is illustrated in FIGS. 62 and 63. The cap 350 can include an engagement feature 352 (e.g., internal threads) for engaging a corresponding engagement feature 318 (e.g., external threads) provided on an outer surface of the core 310 (FIG. 64). FIG. 65 illustrates a core 310 coupled to an example locking mechanism 340 and cap 350. It is contemplated that the cap 350 can include a cutting surface configured to aid in the removal of bone material and/or body tissue during insertion of the core 310 within the patient.

The screw assembly 300 can also include core extensions 360, illustrated in FIGS. 66-70. The core extension 360 provides structure and function similar to the core 310. For example, core extension 360 can define a straight or curved trajectory, can be sized and configured to extend within the central passage 328 of the flexible sleeve 320 and can be constructed from a rigid/stiff material providing the flexible sleeve 320 over the core extension 360 provides stability and strength to the screw assembly 300. Similar to the core 310, the core extension 360 can include a central passage 362, external threads 364 for engaging corresponding threads 330 provided in the flexible sleeve 320, and proximal and distal end engagement features 366 and 368. The core extension 360 can be used when additional travel/length of the screw assembly 300 is required. The distal end engagement feature 368 can be sized and configured to engage the proximal end engagement feature 316 of the core 310. And similar to the core 310, the proximal engagement feature 366 can be sized and configured to engage a corresponding engagement feature 342 of the locking mechanism 340).

Figure 71:
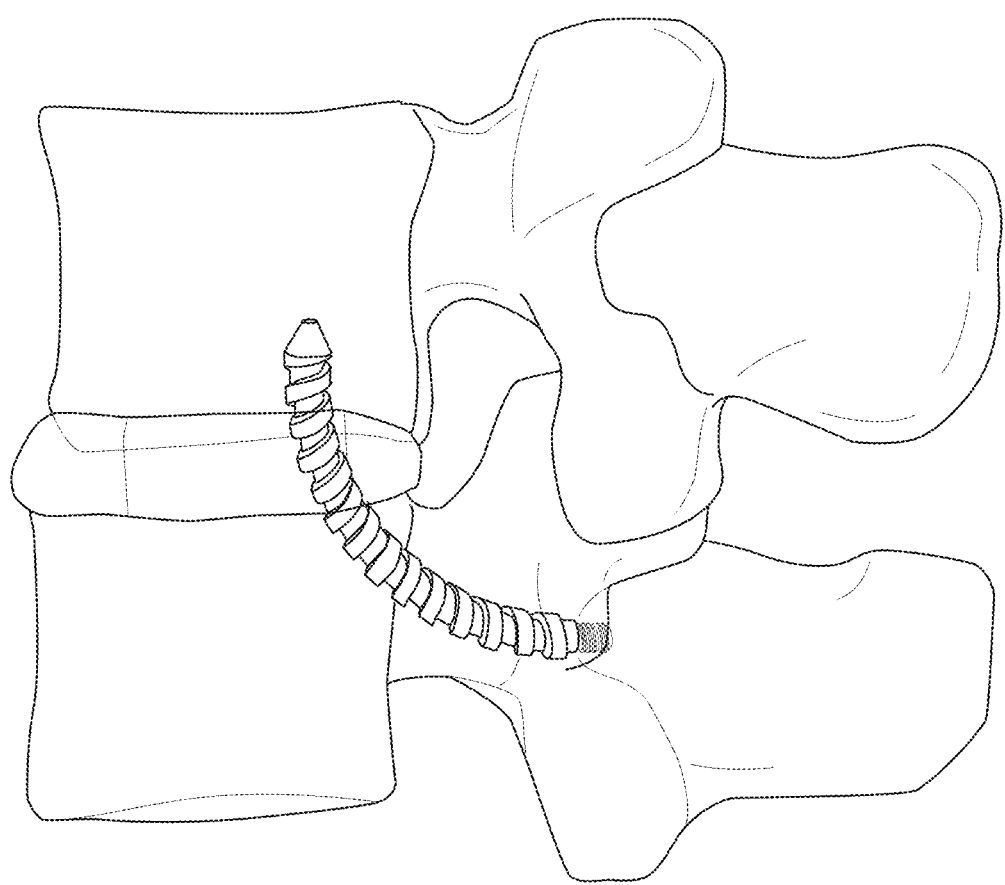
FIG. 71 is a lateral view of an example trajectory of a screw assembly.
Figure 72:
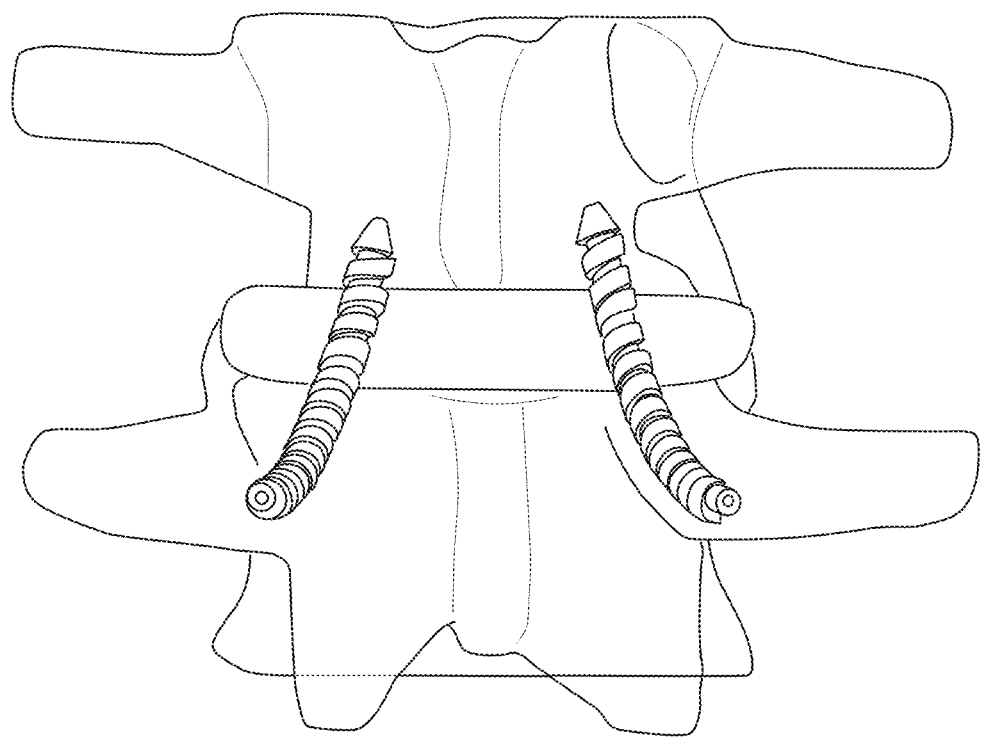
FIG. 72 is a posterior view of an example trajectory of a screw assembly.
Figure 73:
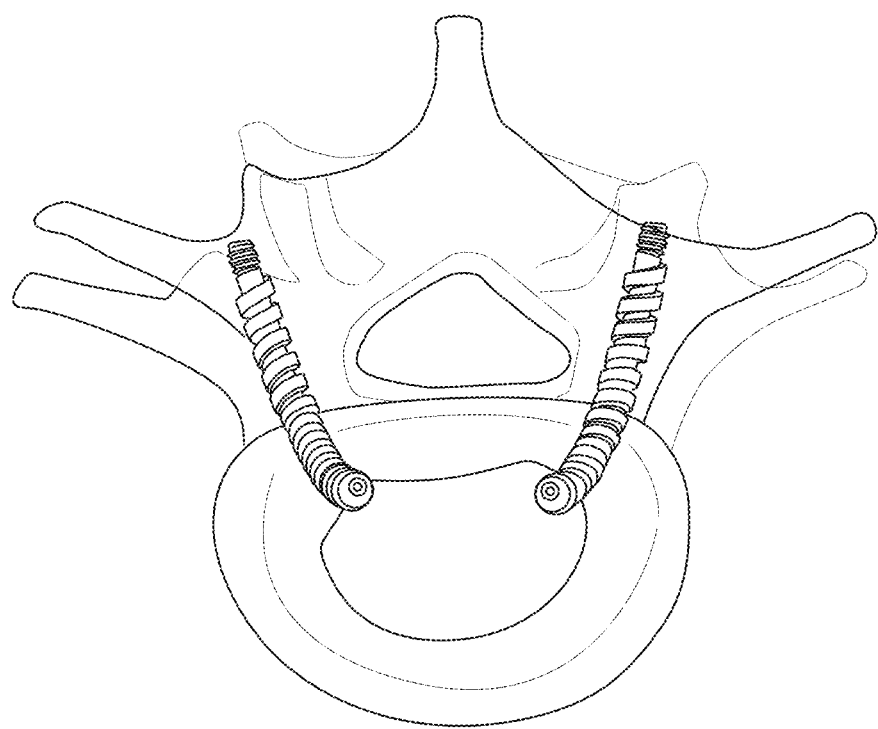
FIG. 73 is a superior view of an example trajectory of a screw assembly.

Using the flexible screw assembly 300, the transdiscal location of multiple flexible vertebral screws can be achieved. FIG. 71 provides a lateral view of an example trajectory of the screw assembly 300. FIG. 72 provides a posterior view of an example trajectory of the screw assembly 300. FIG. 73 provides a superior view of an example trajectory of the screw assembly 300. During insertion, the desired path/location of the screw assembly 300 is identified and a guide hole is drilled into the targeted vertebral bodies. The guide hole can be drilled/tapped using a jamshidi needle or any similar surgical tool capable of providing a straight and/or curved guide hole. The cap 350 can be coupled to the distal end of the core 310 and the core 310 inserted into the guide hole. The flexible sleeve 320 is provided over the core 310. Rotational torque can be provided to the flexible sleeve 320 by engaging a drive tool with the drive surface 338 included at the proximal end of the sleeve 320. As the flexible sleeve 320 is rotated, the external threads 326 assist in drawing the sleeve 320 to its desired location. Additionally, the interlocking teeth 324 allow the flexible sleeve 320 to conform to the (curved and/or straight) shape of the core 310 as the sleeve 320 moves axially along the core 310. If included, engagement between the external threads 314 provided on the core 310 and the internal threads 330 provided in the flexible sleeve 320 also assist in advancing the sleeve 320 towards the distal end of the core 310. Once the flexible sleeve had reached its desired final position and/or the distal end of the sleeve 320 has contacted the cap 350 and can no longer advance along the core 310, the locking mechanism 340 is applied to the proximal end of the core 310 and the position of the screw assembly 300 fixed. If core extensions 360 are used, the engagement feature 368 at the distal end of the core extension 360 is coupled to the engagement feature 316 of the core 310 in lieu of the locking mechanism 340. The locking mechanism 340 is instead coupled to the proximal end engagement feature 366 of the core extension 360. While the screw assembly 300 is described as being assembled in situ, it is contemplated that the screw assembly 300 can be inserted into the patient fully assembled (e.g., flexible sleeve 320) provided around core 310 and cap 350 and locking mechanism 340 coupled to the core 310). It is further contemplated that the various components of the screw assembly can be cannulated and inserted into their desired position using a guide wire.

Figure 74:
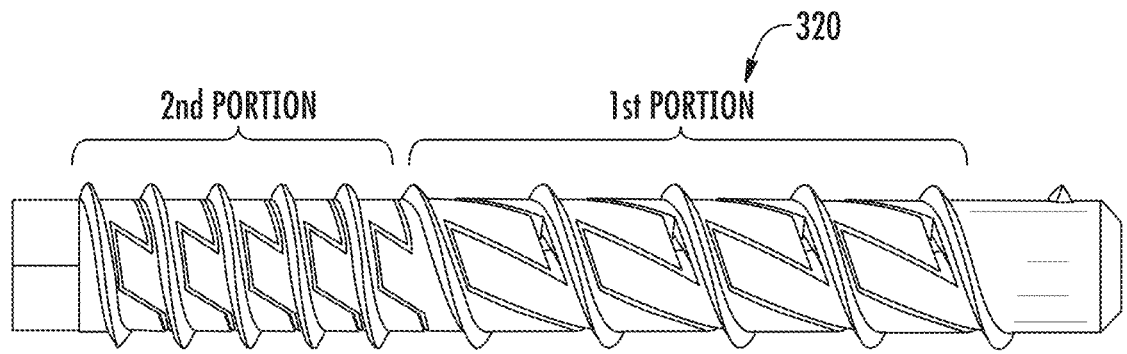
FIG. 74 is a plan view of an example flexible sleeve.
Figure 75:
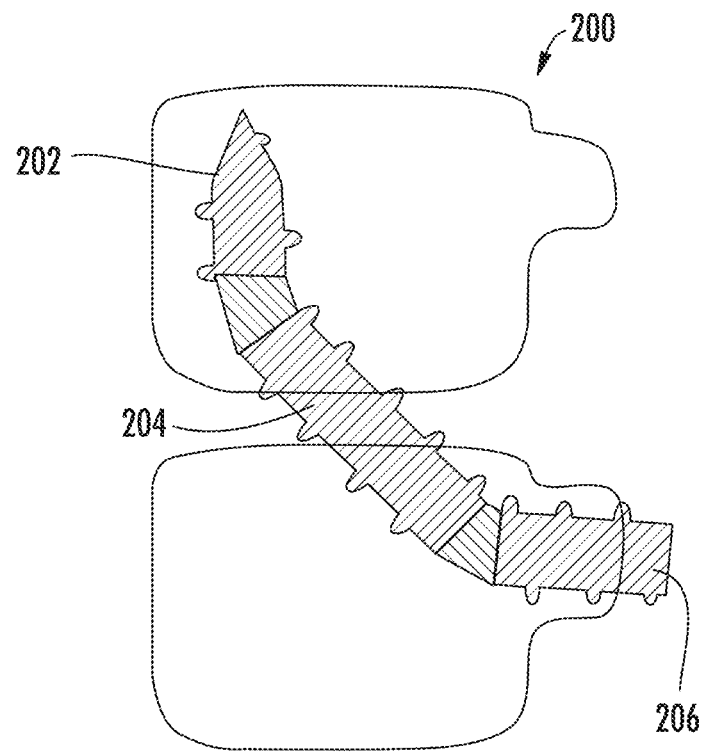
FIG. 75 is a side view of an example screw assembly.
Figure 76:
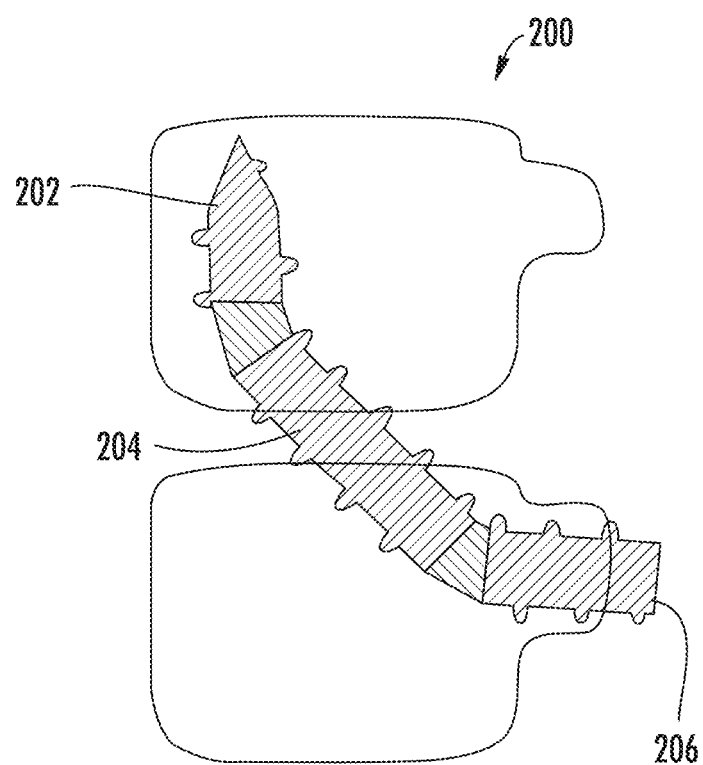
FIG. 76 is a side view of an example screw assembly.

As outlined above, each of the described of the screw assemblies 100, 200 and 300 can be used to couple adjacent vertebral bodies. It is contemplated that the external threads provided on each of the screw assemblies 100, 200 and 300 (e.g., threads 106, threads 108, threads 326) can include a uniform pitch along the length of their respective screws to aid in insertion of the assemblies into the respective vertebral bodies. In another example, the external threads provided on each of the assemblies can be used to provide a compression or decompression effect along the length of the screw. This compression/decompression effect can be provided by a variable pitch along the length of the screw. In particular, compression/decompression effect can be provided by including, for example, a change in pitch between the two portions, a change in pitch separated by a section of unthreaded screw, a constant increase in pitch per turn (e.g., $P=2x$), and/or a nonlinear increase in pitch per turn (e.g., $P=1.2x^2$). FIG. 74 provides an example flexible sleeve 320 including a varying pitch along the length of the sleeve 320. The first portion has a larger pitch with respect to the second portion and increases with a single step as opposed to a smooth transition. Compression, between the vertebral bodies or bone fragments, occurs when the first portion of the screw has a larger pitch than the second and decompression occurs when the second portion of the screw has a larger pitch (opposite to FIG. 74). Varying pitch can also be used with the polyaxial screws described with respect to assemblies 100 and 200 to induce a compression or decompression between adjacent vertebrae. For example, FIG. 75 provides an example polyaxial screw of assembly 200 including different pitches. In particular, third screw 206 can have a first pitch (Pitch 1) and first screw 202 and second screw 204 can include a second pitch (Pitch 2). Depending on the respective pitch values (i.e., Pitch 1 to Pitch 2 ratio), this configuration can create either a compression or decompression between the vertebras. FIG. 76 provides another example polyaxial screw of assembly 200 including different pitches. Alternating the pitches as illustrated creates a compression on the first joint 218a and the second joint 218b. The configuration can be used to increase the stability of the first joint 218a and the second joint 218b or to engage a compression lock utilized with the joints thereby preventing motion of the joints.

Figure 79:
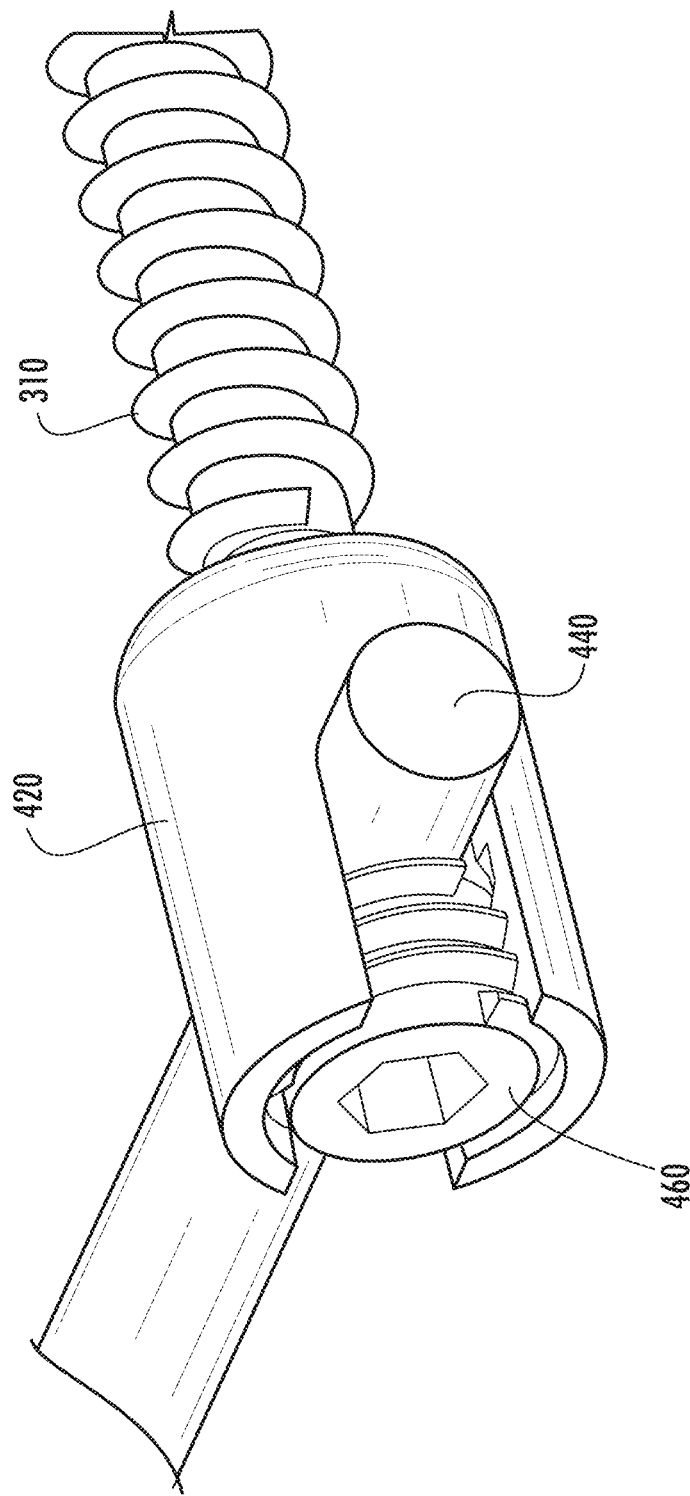
FIG. 79 is a partial perspective view of an example core coupled to a polyaxial pedicle screw.
Figure 80:
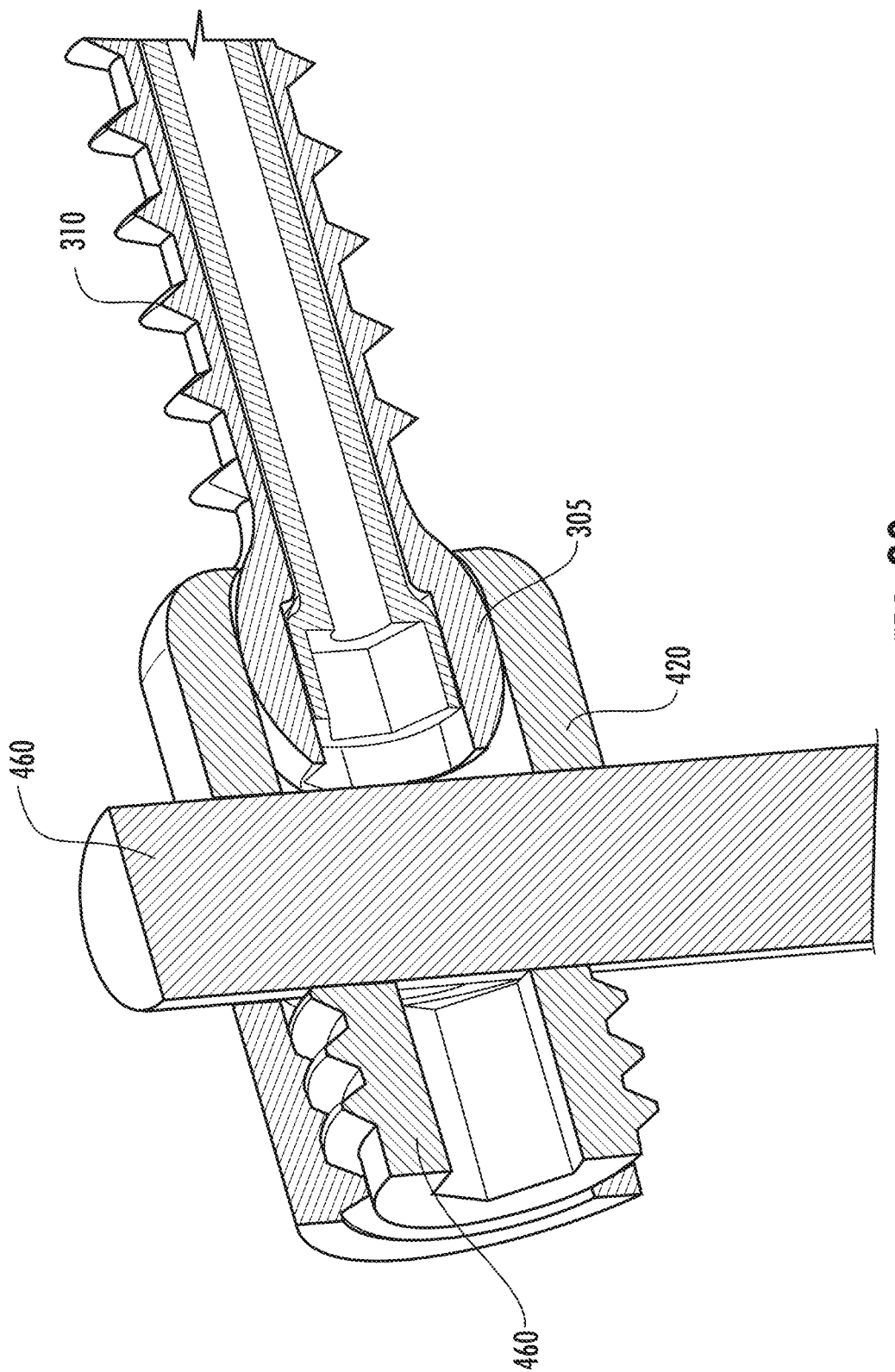
FIG. 80 is a partial perspective cross-sectional view of the example core and polyaxial pedicle screw of FIG. 79.

While the above screw assemblies are described with respect to transdiscal fixation of vertebral bodies, it is contemplated that the disclosed screw assemblies, 100, 200, and 300, can be utilized similar to pedicle screws to provide for the use of spinal rods to connect and stabilize adjacent vertebrae. In particular the heads of the second screw 104, third screw 206 and core 310 (and/or core extension 360) can be sized and configured to engage a polyaxial pedicle screw-type connector. For example, FIGS. 77 and 78 provide an example core 310 including a rounded/ball-shaped head 305 configured to engage a polyaxial pedicle screw-type connector. FIGS. 79 and 80 illustrate an example core 310 head 305 coupled to a polyaxial pedicle screw-type connector 420. A spinal rod 440 can be received within a rod opening provided in the connector 420 and a locking cap 460 can be utilized to fix the spinal rod 440 within the connector 420. In another example (not shown), the screw assemblies 100, 200 and 300 can be utilized within a single object (i.e., a single vertebral body) where the non-linear trajectory would be used to increase the pull-out resistance of the screw or construct.

What is claimed is:

1. A screw assembly for transdiscal fixation of vertebral bodies including:
 a first screw;
 a second screw defining a central passage; and
 a poly-axial joint at least partially coupling the second screw to the first screw, the poly-axial joint at least partially disposed within the central passage of the second screw;
 wherein the first screw and the second screw rotate independently of each other;
 wherein the second screw is configured to advance axially over at least a portion of the poly-axial joint to fix an orientation of the first screw with respect to the second screw in at least one direction.

2. The screw assembly of claim 1, wherein the poly-axial joint comprises a base and an articulated coupling, and wherein the portion of the poly-axial joint is the base.

3. The screw assembly of claim 2, wherein the base defines a connector sized and configured to receive a corresponding driver.

4. The screw assembly of claim 1, wherein the second screw comprises a connector sized and configured to receive a corresponding driver, the connector disposed at a proximal end of the second screw.

5. The screw assembly of claim 1, wherein the first screw defines a first outer diameter and the second screw defines a second outer diameter.

6. The screw assembly of claim 5, wherein the first outer diameter is equal to the second outer diameter.

7. The screw assembly of claim 5, wherein the first outer diameter is less than the second outer diameter.

8. The screw assembly of claim 2, wherein the articulated coupling is a universal joint.

9. The screw assembly of claim 1, wherein an external thread of the first screw has a pitch less than a pitch of an external thread of the second screw.

10. The screw assembly of claim 1, wherein the first screw includes a central passage sized and configured to receive a guide wire.

11. The screw assembly of claim 2, further comprising a casing disposed within the central passage of the second screw, the casing defining a set of external threads that engage with a corresponding set of internal threads in the central passage of the second screw such that rotational movement of the casing with respect to the central passage of the second screw translates into axial movement of the casing within the central passage and a corresponding axial movement of the first screw with relative to the second screw.

12. The screw assembly of claim 11, wherein the casing defines a cavity sized and configured for receiving the base of the poly-axial joint.

13. The screw assembly of claim 11, wherein, as the casing is moved axially in a proximal direction, a proximal end of the first screw is translated towards a proximal end of the second screw.

14. The screw assembly of claim 12, wherein a distal end of the cavity comprises a protrusion extending radially towards a longitudinal axis of the casing, where interference between the protrusion and an outer surface of the base limits distal axial motion of the base.

15. The screw assembly of claim 14, wherein the casing is moveable axially between a first condition wherein the base of the poly-axial joint is free to rotate and move axially within the cavity and a second condition wherein at least one degree of axial motion or rotation of the base of the poly-axial joint is constrained.

16. The screw assembly of claim 12, wherein a proximal end of the cavity comprises an opening, the opening having a diameter less than a diameter of the cavity, wherein the opening defines a central passage extending through a proximal end of the casing.

17. The screw assembly of claim 16, further comprising a lock sized and configured to be received within the central passage of the casing, wherein the lock is movable axially in the central passage in a distal direction such that, when a distal end of the lock engages the base of the poly-axial joint, axial movement of the base of the poly-axial joint in a proximal direction is restricted.

18. The screw assembly of claim 17, wherein a proximal portion of the lock comprises external threads that engage with the internal threads in the central passage of the second screw.

* * * * *